US008217060B2

(12) United States Patent
Calvo et al.

(10) Patent No.: US 8,217,060 B2
(45) Date of Patent: Jul. 10, 2012

(54) BENZIMIDAZOLE DERIVATIVES USEFUL AS TRP M8 RECEPTOR MODULATORS

(75) Inventors: Raul R. Calvo, Royersford, PA (US); Sanath K. Meegalla, Boothwyn, PA (US); Mark R. Player, Phoenixville, PA (US)

(73) Assignee: Janssen Pharmaceutica, NV, Beerse (BE)

( * ) Notice: Subject to any disclaimer, the term of this patent is extended or adjusted under 35 U.S.C. 154(b) by 95 days.

(21) Appl. No.: 12/773,083

(22) Filed: May 4, 2010

(65) Prior Publication Data

US 2010/0292276 A1 Nov. 18, 2010

Related U.S. Application Data

(60) Provisional application No. 61/178,596, filed on May 15, 2009.

(51) Int. Cl.
*A61K 31/41* (2006.01)
*A61K 31/415* (2006.01)
(52) U.S. Cl. ...................................... 514/338; 514/394
(58) Field of Classification Search .................. None
See application file for complete search history.

(56) References Cited

FOREIGN PATENT DOCUMENTS

| WO | WO 2005/101989 A2 | 11/2005 |
|---|---|---|
| WO | WO 2005/101989 A3 | 11/2005 |
| WO | WO 2006/001752 A1 | 1/2006 |
| WO | WO 2007/130780 A2 | 11/2007 |
| WO | WO 2008/076752 A1 | 6/2008 |

OTHER PUBLICATIONS

Abe, J., et al. "Ca2+-dependent PKC activation mediates menthol-induced desensitization of transient receptor potential M8", *Neurosci Lett*, 2006, pp. 140-144, vol. 397(1-2).
Barnett, A.G., et al. "Cold periods and coronary events: an analysis of populations worldwide", *J Epidemiol Community Heath*, 2005, pp. 551-557, vol. 59.
Behrendt, H-J., et al., "Characterization of the mouse cold menthol receptor TRPM8 and vaniloid receptor type-1 VR1 using a fluormetric imaging plate reader (FLIPR) assay", *Brit J Pharmacol*, 2004, pp. 737-745, vol. 141(4).
Bennett, G.J. et al., "A Peripheral Mononeuropathy in Rat that Produces Disorders of Pain Sensation Like Those Seen in Man", *Pain*, 1988, pp. 87-107, vol. 33(1).
Bhatnagar, S., et al. "Tramadol for Postoperative Shivering: A Double Blind Comparison with Pethidine", *Anaesth Intensive Care*, 2001, pp. 149-154, vol. 29(2).
Bolser, D.C. et al., "Pharmacological studies of allergic cough in the guinea pig", *Eur J Pharmacol*, 1995, pp. 159-164, vol. 277(2-3).
Braga, P.C. "Dextrorphan and Dextromethorphan: comparative antitussive effects on guinea pigs", *Drugs Exper Clin Res*, 1994, pp. 199-203, vol. 20.
Braw, et al. "Anxiety-like behaviors in pre-pubertal rats of the Flinders Sensitive Line (FSL) and Wistar-Kyoto (WKY) animal models of depression", *Behav Brain Res*, 2006, pp. 261-269, vol 167.
Butler, S.H., et al, "A limited arthritic model for chronic pain studies in the rat", *Pain*, 1992, pp. 73-81, vol. 48.
Collier, H.O., et al. "The Abdominal Constriction Response and Its Suppression by Analgesic Drugs in the Mouse", *Br J Pharmacol Chemother*, 1968, pp. 295-310, vol. 32(2).
Cryan, J.F., et al., "Model organisms: the ascent of mouse: advances in modeling human depression and anxiety", *Nat. Rev. Drug Discov.*, 2005, 99 775-790, vol. 4(9).
Defrin, R., et al., "Characterization of chronic pain and somatosensory function in spinal cord injury subjects", *Pain*, 2001, pp. 253-263, vol. 89(2-3).
Defrin, R., et al. "Sensory Determinants of Thermal Pain", *Brain*, 2002, pp. 501-510, vol. 125(Pt 3).
Desmeules, J.A., et al., "Neurophysiologic Evidence for a Central Sensitization in Patients With Fibromyalgia", *Arthritis Rheum*, 2003, pp. 1420-1429, vol. 48(5).
Eccles, R. "Menthol: Effects on Nasal Sensation of Airflow and the Drive to Breathe", *Curr Allergy Asthma Rep*, 2003, pp. 210-214, vol. 3(3).
EL Mouedden, M. et al., "Evaluation of pain-related behavior, bone destruction and effectiveness of fentanyl, sufentanil, and morphine in a murine model of cancer pain", *Pharmacol Biochem Behav*, 2005, pp. 109-119, vol. 82(1).
Erichsen, et al., "Comparative actions of the opioid analgesics morphine, methadone and codeine in rat models of peripheral and central neuropathic pain", *Pain*, 2005, pp. 347-358, vol. 116.
Finnerup, N. B., et al., "Intravenous Lidocaine Relieves Spinal Cord Injury Pain: A Randomized Controlled Trial", *Anesthesiology*, 2005, pp. 1023-1030, vol. 102(5).
Fox, A., et al., "Critical evaluation of the streptozotocin model of painful diabetic neuropathy in the rat", *Pain*, 1999, pp. 307-316, vol. 81.
Ghilardi, J.R., et al., "Selective Blockade of the Capsaicin Receptor TRPV1 Attenuates Bone Cancer Pain" *J Neurosci*, 2005, pp. 3126-3131, vol. 25(12).
Grahn, D.A., et al. "Appropriate thermal manipulations eliminate tremors in rats recovering from halothane anesthesia", *J Applied Physiology*, 1996, pp. 2547-2554, vol. 81.
Greenspan, J.D., et al., "Allodynia in patients with post-stroke central pain (CPSP) studied by statistical quantitative sensory testing within individuals", *Pain*, 2004, pp. 357-366, vol. 109(3).
Hall, et al., "Time-course of infection and responses in a coughing rat model of pertussis", *J Med Microbiol*, 1999, pp. 95-98, vol 48.
Hallas, B. et al., "Establishment of behavioral parameters for the evaluation of osteopathic treatment principles in a rat model of arthritis", *J Am Osteopath Assoc*, 1997, pp. 207-214, vol. 97(4).
Hirayama, Y., et al., "Effect of FK3657, a non-peptide bradykinin B2 receptor antagonist,on allergic airway disease models", *Eur J Pharmacol*, 2003, pp. 197-203, vol. 467(1-3).
Hunter, J.C., et al.,"The effect of novel anti-epileptic drugs in rat experimental models of acute and chronic pain" *Eur J Pharmacol* 1997, pp. 153-160, vol. 324.

(Continued)

*Primary Examiner* — Craig Ricci
(74) *Attorney, Agent, or Firm* — Thomas J. Dodd

(57) ABSTRACT

The present invention is directed to benzimidazole derivatives, pharmaceutical compositions containing them and their use in the treatment of disorders and conditions modulated by TRP M8 (transient receptor potential M8 channel). More particularly, the compounds of the present invention are useful in the treatment of inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold, anxiety and depression.

12 Claims, No Drawings

OTHER PUBLICATIONS

Iyengar, S., et al., "Efficacy of Duloxetine, a Potent and Balanced Serotonin-Norepinephrine Reuptake Inhibitor in Persistent Pain Models in Rats", *JPET*, 2004, pp. 576-584, vol. 311.

Jorum, E., et al., "Cold allodynoa and hyperalgesia in neuropathic pain: the effect of N-methyl-D-aspartate (NMDA) receptor antagonist etamine—a doulble-blind, cross-over comparison with alfentanil and placebo", *Pain*, 2003, pp. 229-235, vol. 101.

Kobayashi, K., et al. "Distinct expression of TRPM8, TRPA1 and TRPV1 mRNAs in rat primary afferent neurons with a c-fibers and colocalization with Trk receptors" *J Comp Neurol*, 2005, pp. 596-606, vol. 493(4), 596-606.

Koltzenberg, M., et al., "Differential sensitivity of three experimental pain models in detecting the analgesic effects of transdermal fentanyl and buprenorphine", *Pain*, 2006, pp. 165-174, vol. 126 (1-3).

Kozak, W. et al., "Non-Prostaglandin Eicosanoids in Fever and Anapyrexia", *Front Biosci*, 2004, pp. 3339-3355, vol. 9.

Kydonieus, A., et al., "Elimination of Transdermal Drug-Induced Hypersensitivity by Topical Delivery of Ion Channel Modulating Agents", *Proceedings of the International Symposium on Controlled Release of Bioactive Materials*, 1997, 24th, pp. 23-24.

Laude, E. A., et al."The Antitussive Effects of Menthol, Camphor, and Cineole in Conscious Guinea Pigs", *Pulm Pharmacol*, 1994, pp. 179-184, vol. 7(3).

Lee, S., et al. "Behavioral Characteristics of a mouse model of cancer pain", *Yonsei Med J*, 2005, pp. 252-259, vol. 46(2).

Luger, N.M., et al., "Efficacy of systemic morphine suggest a fundamental difference in the mechanisms that generate bone cancers vs. inflammatory pain", *Pain*, pp. 397-406, vol. 99(3).

Magyar, T., et al., "Evauation of vaccines for atrophic rhinitis—a comparison of three challenge models", Vaccine, 2002, pp. 1797-1802, vol. 20(13-14).

McKemy, D.D., et al "Identification of a cold receptor reveals a general role for TRP channels inthermosensation", *Nature*, pp. 52-58, vol. 416 (6876).

McMurray, G., et al., "Animal models in urological disease and sexual dysfunction", *Br J Pharmacol*, 2006,: S62-79, vol. 147, Suppl 2.

Morice, A.H., et al. "Effect of inhaled menthol on citric acid induced cough in normal subjects", *Thorax*, 1994, pp. 1024-1026, vol. 49(10).

Morin, C., et al., "Disruption of Thermal Perception in a Multiple Sclerosis Patient With Central Pain", *Clin J Pain*, 2002, pp. 191-195, vol. 18(3).

Motta, A.F., et al., "The antinociceptive effect of iontophoretic direct application of diclofenac to arthritic knee-joints of rats", *Life Sci*, 2003, pp. 1995-2004, vol. 73 (15).

Mukerji, G. et al. "Pain during ice water test distinguishes clinical bladder hypersensitivity from overactivity disorders" BMC Urology, 2006, p. 6, vol. 6.

Nagakura, Y., "Allodynia and Hyperalgesia in Adjuvant-Induced Arthritic Rats:Time Course of Progression and Efficacy of Analgesics", *J Pharmacol Exp Ther*, 2003, pp. 490-497, vol. 306(2).

Nikki, P., et al., "Halothane-Induced Heat Loss and Shivering in Rats", *Acta Anaesthesiol Scand*,1968, pp. 125-134, vol. 12(3).

Pomonis, J.D., et al., "N—(4-Tertiarybutylpheny1)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain", *JPET*, 2003, pp. 387-393, vol. 306.

Premkumar, L.S., et al. "Downregulation of Transient Receptor Potential Melastatin 8 by Protein Kinase C-Mediated Dephosphorylation", *J. Neurosci*, 2005, pp. 11322-11329, vol. 25(49).

Ribeiro, R.A., et al., "Involvement of resident macrophages and mast cells in the writhing nociceptive response induced by zymosan and acetic acid in mice", *Eur J Pharmacol*, 2000, pp. 111-118, vol. 387(1).

Roza, C. et al., "Cold sensitivity in axotomized fibers of experimental neuromas in mice", *Pain*, 2006, pp. 24-36, vol. 120(1-2).

Rupniak, N.M.J., et al., "Effects of the bradykinin $B_1$ receptor des-Arg$^9$ [Leu$^8$]bradykinin and genetic disruption of the $B_2$ receptor on nociception in rats and mice", *Pain*, 1997, pp. 89-97, vol. 71.

Sabino, M.A., et al., "Simultaneous Reduction in Cancer Pain, Bone Destruction, and Tumor Growth by Selective Inhibition of Cyclooxygenase-2", *Cancer Res*, 2002, pp. 7343734-9, vol. 62 (24).

Saint-Mezard, P., et al. "Allergic contact dermatitis" *Eur J Dermatol*, 2004, pp. 284-295, vol. 14 (5).

Sluka, K.A., et al., "Behavioral and immunohistochemical changes in an experimental arthritis model in rats", *Pain*, 1993, pp. 367-377, vol. 55 (3).

Soulard, C., et al., "Pharmacological Evaluation of JO 1870: Relation to the Potential Treatment of Urinary Bladder Incontinence", *J Pharmacol Exp Ther*, 1992, pp. 1152-1158, vol. 260 (3).

Stein, R.J., et al., "Cool (TRPM8) and hot (TRPV1) receptors in the bladder and male genital tract", *J Urol*, 2004,): pp. 1175-1178, vol. 172(3).

Suzuki, R., et al., "The effectiveness of spinal and systemic morphine on rat dorsal horn neuronal responses in the spinal nerve ligation model of neuropathic pain", *Pain*, 1999, pp. 215-228, vol. 80.

Svendsen, K.B., et al. "Sensory function and quality of life in patients with multiple sclerosis and pain", *Pain*, 2005, pp. 473-481, vol. 114(3).

Tanaka, M., et al., "Mechanisms of Capsaicin- and Citric-Acid-Induced Cough Reflexes in Guinea Pigs", *J Pharmacol. Sci*, 2005, pp. 77-82, vol. 99(1).

Thomsen, J.S., et al. "The effect of topically applied salicylic compounds on serotonin-induced scratching behavior in hairless rats", *J Exp Dermatol*, 2002, pp. 370-375, vol. 11(4).

Tiniakov, R.L., et al. "Canine model of nasal congestion and allergic rhinitis", *J Appl Physiol*, 2003, pp. 1821-1828, vol. 94(5).

Tomazetti, J. et al., "Baker yeast-induced fever in young rats: Characterization and validation of an animal model for antipyretics screening", *J Neurosci Methods*, 2005, pp. 29-35, vol. 147(1).

Trevisani, M., et al., "Antitussive activity of iodo-resiniferatoxin in guinea pigs" *Thorax*, 2004, pp. 769-772, vol. 59(9).

Tsai, Y.C., etal., "A Comparison of Tramadol, Amitriptyline, and Meperidine for Postepidural Anesthetic Shivering in Parturients", *Anesth Analg*, 2001, pp. 1288-1292, vol. 93(5).

Tsukimi, Y., et al. "Cold response of the bladder in guinea pig: involvement of transient receptor potential channel, TRPM8", *Urology*, 2005, pp. 406-410, vol. 65(2).

Van Miert, A.S, et al., "The Antipyretic Effect of Flurbiprofen", *Eur J Pharmacol*, 1977, pp. 197-204, vol. 44(3).

Wei, E.T., et al., "AG-3-5: a chemical producing sensations of cold", *J Pharm Pharmacol.*, 1983, pp. 110-112, vol. 35.

Weisshaar, E, et al. "Effect of topical capsaicin on the cutaneous reactions and itching to histamine in atopic eczema compared to healthy skin", *Arch Dermatol Res*, 1998, pp. 306-311, vol. 290(6).

Weisshaar, E., et al., "Systemic Drugs with Antipruritic Potency", *Skin Therapy Lett*, 2000, pp. 1-25, vol. 5(5).

Wille, J.J., et al. "cis -Urocanic Acid Induces Mast Cell Degranulation and Release of Preformed TNF-•: A Possible Mechanism Linking UVB and cis-Urocanic Acid to Immunosuppression of Contact Hypersensitivity", *Skin Pharmacol Appl Skin Physiol*, 1999, pp. 18-27, vol. 12(1-2).

Woods, M. et al., Efficacy of the 3-adrenergic receptor agonist CL-316243 on experimental bladder hyperreflexia and detrusor instability (J Urol, 2001).

Xing, H., et al., "Chemical and Cold Sensitivity of Two Distinct populations of TRPM8-Expressing Somatosensory Neurons", *J Neurophysiol*, 2006, pp. 1221-1230, vol. 95(2).

Yaksh, T.L., et al., "Vincristine-induced allodynia in the rat", *Pain*, 2001, pp. 69-76, vol. 93.

Young, S. T. et al., "Synthetic Studies in the Fumagillin Series", *J. Org. Chem.*, 1963, pp. 928-932, vol. 28.

BENZIMIDAZOLE DERIVATIVES USEFUL AS TRP M8 RECEPTOR MODULATORS

CROSS-REFERENCE TO RELATED APPLICATIONS

The present application claims the benefits of the filing of U.S. Provisional Application No. 61/178,596, filed May 15, 2009. The complete disclosures of the aforementioned related patent applications are hereby incorporated herein by reference for all purposes.

FIELD OF THE INVENTION

The present invention is directed to novel benzimidazole derivatives, pharmaceutical compositions containing them and their use in the treatment of disorders and conditions modulated by TRP M8 (transient receptor potential M8 channel). More particularly, the compounds of the present invention are useful in the treatment of inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold, anxiety and depression.

BACKGROUND OF THE INVENTION

Transient receptor potential (TRP) channels are non-selective cation channels that are activated by a variety of stimuli. Numerous members of the ion channel family have been identified to date, including the cold-menthol receptor, also called TRP M8 (MCKEMY, D. D., et al "Identification of a cold receptor reveals a general role for TRP channels in thermosensation", *Nature*, pp 52-58, Vol. 416 (6876)). Collectively, the TRP channels and related TRP-like receptors connote sensory responsivity to the entire continuum of thermal exposure, selectively responding to threshold temperatures ranging from noxious hot through noxious cold as well as to certain chemicals that mimic these sensations. Specifically, TRP M8 is known to be stimulated by cool to cold temperatures as well as by chemical agents such as menthol and icilin, which may be responsible for the therapeutic cooling sensation that these agents provoke.

TRP M8 is located on primary nociceptive neurons (A-delta and C-fibers) and is also modulated by inflammation-mediated second messenger signals (ABE, J., et al. "Ca2+-dependent PKC activation mediates menthol-induced desensitization of transient receptor potential M8", *Neurosci Lett*, 2006, pp 140-144, Vol. 397(1-2); PREMKUMAR, L. S., et al. "Downregulation of Transient Receptor Potential Melastatin 8 by Protein Kinase C-Mediated Dephosphorylation", *J. Neurosci*, 2005, pp 11322-11329, Vol. 25(49)). The localization of TRPM8 on both A-delta and C-fibers may provide a basis for abnormal cold sensitivity in pathologic conditions wherein these neurons are altered, resulting in pain, often of a burning nature (KOBAYASHI, K., et al. "Distinct expression of TRPM8, TRPA1 and TRPV1 mRNAs in rat primary afferent neurons with a c-fibers and colocalization with Trk receptors" *J Comp Neurol*, 2005, pp 596-606, Vol. 493(4), 596-606; ROZA, C. et al., "Cold sensitivity in axotomized fibers of experimental neuromas in mice", *Pain*, 2006, pp 24-36, Vol 120(1-2); XING, H., et al., "Chemical and Cold Sensitivity of Two Distinct populations of TRPM8-Expressing Somatosensory Neurons", J Neurophysiol, 2006, pp 1221-1230, Vol. 95(2)). Cold intolerance and paradoxical burning sensations induced by chemical or thermal cooling closely parallel symptoms seen in a wide range of clinical disorders and thus provide a strong rationale for the development of TRP M8 modulators as novel antihyperalgesic or antiallodynic agents. TRP M8 is also known to be expressed in the brain, lung, bladder, gastrointestinal tract, blood vessels, prostate and immune cells, thereby providing the possibility for therapeutic modulation in a wide range of maladies.

There remains a need in the art for TRPM8 antagonists that can be used to treat a disease or condition in a mammal in which the disease or condition is affected by the modulation of TRPM8 receptors, such as chronic or acute pain, or the diseases that lead to such pain, and pulmonary or vascular dysfunction.

SUMMARY OF THE INVENTION

The present invention is directed to compounds of formula (I)

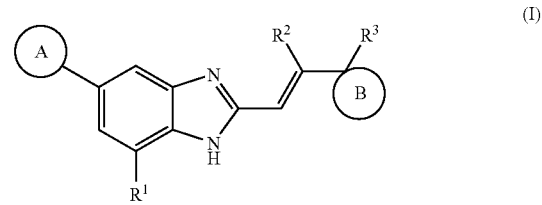

wherein
$R^1$ is selected from the group consisting of hydrogen, halogen, lower alkyl and halogenated lower alkyl;

is selected from the group consisting of phenyl, pyridyl and thienyl; wherein the phenyl, pyridyl or thienyl is optionally substituted with one or more substituents independently selected from the group consisting of halogen, hydroxy, lower alkyl, hydroxy substituted lower alkyl, halogenated lower alkyl, lower alkoxy, halogenated lower alkoxy, cyano, —C(O)-(lower alkyl) and 2-(2-methyl-[1,3]dioxolanyl);

$R^2$ is selected from the group consisting of hydrogen and methyl;

$R^3$ is selected from the group consisting of hydrogen and methyl;

is a ring structure selected from the group consisting of

wherein X is selected from the group consisting of $CR^5R^6$, O and S; and wherein $R^5$ and $R^6$ are each independently selected from the group consisting of hydrogen, halogen and lower alkyl;

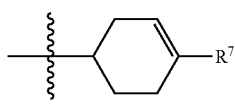
(b)

wherein R⁷ is selected from the group consisting of hydrogen, halogen and lower alkyl;

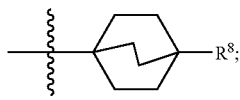
(c)

wherein R⁸ is selected from the group consisting of hydrogen, halogen and lower alkyl; and

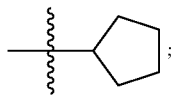
(d)

and solvates, hydrates, tautomers and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by TRP M8 (selected from the group consisting of inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold, anxiety and depression) in a subject in need thereof comprising administering to the subject a therapeutically effective amount of any of the compounds or pharmaceutical compositions described above.

Another example of the invention is the use of any of the compounds described herein in the preparation of a medicament for treating: (a) inflammatory pain, (b) inflammatory hyperalgesia, (c) inflammatory hypersensitivity condition, (d) neuropathic pain, (e) neuropathic cold allodynia, (f) inflammatory somatic hyperalgesia, (g) inflammatory visceral hyperalgesia, (h) cardiovascular disease aggravated by cold, (i) anxiety and (j) depression, in a subject in need thereof.

DETAILED DESCRIPTION OF THE INVENTION

The present invention is directed to compounds of formula (I)

(I)

wherein $R^1$, $R^2$, $R^3$,

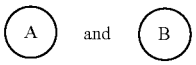

are as herein defined, and solvates, hydrates, tautomers and pharmaceutically acceptable salts thereof. The compounds of the present invention are useful as in the treatment of disorder mediated by TRP M8, including inflammatory pain, inflammatory hyperalgesia, inflammatory hypersensitivity condition, neuropathic pain, neuropathic cold allodynia, inflammatory somatic hyperalgesia, inflammatory visceral hyperalgesia, cardiovascular disease aggravated by cold, anxiety and depression.

In an embodiment of the present invention, $R^1$ is selected from the group consisting of hydrogen, lower alkyl and fluorinated lower alkyl. In another embodiment of the present invention, $R^1$ is selected from the group consisting of hydrogen, C-2alkyl and fluorinated $C_{1-2}$alkyl. In another embodiment of the present invention, $R^1$ is selected from the group consisting of hydrogen, methyl and trifluoromethyl. In another embodiment of the present invention, $R^1$ is hydrogen.

In an embodiment of the present invention, $R^2$ is selected from the group consisting of hydrogen and methyl. In another embodiment of the present invention, $R^2$ is hydrogen.

In an embodiment of the present invention, $R^3$ is selected from the group consisting of hydrogen and methyl. In another embodiment of the present invention, $R^3$ is hydrogen.

In an embodiment of the present invention,

is selected from the group consisting of phenyl, pyridyl and thienyl; wherein the phenyl, pyridyl or thienyl is optionally substituted with one to two substituents independently selected from the group consisting of halogen, hydroxy, lower alkyl, hydroxy substituted lower alkyl, fluorinated lower alkyl, lower alkoxy, fluorinated lower alkoxy, cyano, —C(O)-(lower alkyl) and 2-(2-methyl-[1,3]dioxolanyl).

In another embodiment of the present invention,

is selected from the group consisting phenyl, pyridyl and thienyl; wherein the phenyl, pyridyl or thienyl is optionally substituted with one to two substituents independently selected from the group consisting of halogen, hydroxy, cyano, $C_{1-2}$alkyl, $C_{1-2}$alkoxy, fluorinated $C_{1-2}$alkyl, fluorinated $C_{1-2}$alkoxy, hydroxy substituted $C_{1-2}$alkyl, —C(O)—$C_{1-2}$alkyl and 2-methyl-[1,3]dioxanyl.

In another embodiment of the present invention,

Ⓐ is selected from the group consisting phenyl, 2-fluorophenyl, 2-chlorophenyl, 3-hydroxyphenyl, 2-hydroxymethyl-phenyl, 2-methylphenyl, 2-(2,2,2-trifluoroethoxy)-phenyl, 2-trifluoromethoxyphenyl, 2-trifluoromethylphenyl, 2-cyanophenyl, 2,5-dichlorophenyl, 2,5-difluorophenyl, 2,6-difluorophenyl, 2,6-dimethyphenyl, 2,4-dimethoxyphenyl, 2,6-dimethoxyphenyl, 2-trifluoromethoxy-5-fluoro-phenyl, 2-trifluoromethoxy-6-fluoro-phenyl, 2-methoxy-4-fluoro-phenyl, 2-chloro-5-fluoro-phenyl, 2-chloro-6-fluoro-phenyl, 2-chloro-5-methoxy-phenyl, 3-chloro-6-methoxy-phenyl, 3-fluoro-6-methoxy-phenyl, 2-fluoro-6-methoxy-phenyl, 2-fluoro-6-trifluoromethyl-phenyl, 2-fluoro-6-trifluoromethoxy-phenyl, 2,6-di(trifluoromethyl)phenyl, 2-methylcarbonyl-phenyl, 2-(2-methyl-[1,3]dioxanyl)-phenyl, 2-(3-methyl-thienyl), 4-(3-trifluoromethyl-pyridyl), 3-(2-trifluoromethyl-pyridyl), 2-(3-trifluoromethyl-pyridyl) and 2-(6-trifluoromethyl-pyridyl).

In another embodiment of the present invention,

Ⓐ is selected from the group consisting 2-fluorophenyl, 2-chlorophenyl, 2-hydroxymethyl-phenyl, 2-methylphenyl, 2-(2,2,2-trifluoroethoxy)phenyl, 2-trifluoromethoxyphenyl, 2-trifluoromethylphenyl, 2,6-dimethyphenyl, 2,6-dimethoxyphenyl, 2-trifluoromethoxy-5-fluoro-phenyl, 2-chloro-5-fluoro-phenyl, 2-chloro-6-fluoro-phenyl, 3-fluoro-6-methoxy-phenyl, 2-fluoro-6-methoxy-phenyl, 2-fluoro-6-trifluoromethyl-phenyl, 2-fluoro-6-trifluoromethoxy-phenyl, 2,6-di(trifluoromethyl)phenyl, 2-(3-methyl-thienyl), 3-(2-trifluoromethyl-pyridyl) and 2-(3-trifluoromethyl-pyridyl).

In another embodiment of the present invention,

Ⓐ is selected from the group consisting 2-fluorophenyl, 2-chlorophenyl, 2-methylphenyl, 2-(2,2,2-trifluoroethoxy)-phenyl, 2-trifluoromethoxyphenyl, 2-trifluoromethylphenyl, 2,6-dimethyphenyl, 2,6-dimethoxyphenyl, 2-trifluoromethoxy-5-fluoro-phenyl, 2-chloro-6-fluoro-phenyl, 3-fluoro-6-methoxy-phenyl, 2-fluoro-6-methoxy-phenyl, 2-fluoro-6-trifluoromethyl-phenyl and 2-fluoro-6-trifluoromethoxy-phenyl. In another embodiment of the present invention,

Ⓐ is selected from the group consisting of 2-trifluoromethylphenyl, 2,6-di(trifluoromethyl)-phenyl and 2-fluoro-6-trifluoromethyl-phenyl.

In an embodiment of the present invention,

Ⓑ is a ring structure selected from the group consisting of

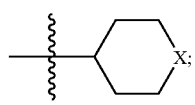

(a)

wherein X is selected from the group consisting of $CR^5R^6$, O and S; and wherein $R^5$ and $R^6$ are each independently selected from the group consisting of hydrogen, halogen and lower alkyl;

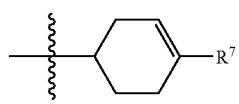

(b)

wherein $R^7$ is selected from the group consisting of hydrogen and halogen;

(c)

wherein $R^8$ is selected from the group consisting of hydrogen and halogen; and

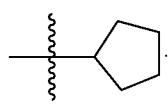

(d)

In another embodiment of the present invention,

Ⓑ is a ring structure selected from the group consisting of

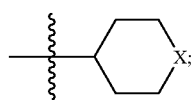

(a)

wherein X is selected from the group consisting of $CR^5R^6$, O and S; and wherein $R^5$ and $R^6$ are each independently selected from the group consisting of hydrogen, halogen and $C_{1-2}$alkyl;

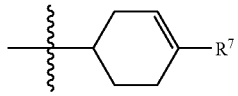
(b)

wherein $R^7$ is selected from the group consisting of hydrogen and halogen;

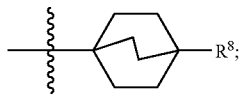
(c)

wherein $R^8$ is selected from the group consisting of hydrogen and halogen; and

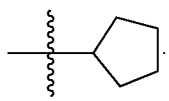
(d)

In another embodiment of the present invention,

is a selected from the group consisting of cyclopentyl, cyclohexyl, 1-(4,4-difluoro-cyclohexyl), 1-(4,4-dimethyl-cyclohexyl), 4-(1-fluoro-cyclohexenyl), 4-tetrahydropyranyl, 4-tetrahydrothiopyranyl and 4-(1-bromo-bicyclo[2.2.]octanyl). In another embodiment of the present invention,

is a selected from the group consisting of cyclopentyl, cyclohexyl, 1-(4,4-difluoro-cyclohexyl), 1-(4,4-dimethyl-cyclohexyl), 4-(1-fluoro-cyclohexenyl), 4-tetrahydropyranyl and 4-(1-bromo-bicyclo[2,2]octanyl). In another embodiment of the present invention,

is a selected from the group consisting of cyclohexyl, 1-(4,4-difluoro-cyclohexyl), 4-(1-fluoro-cyclohexenyl) and 4-tetrahydropyranyl. In another embodiment of the present invention,

is a selected from the group consisting of cyclohexyl, 1-(4,4-difluoro-cyclohexyl) and 4-tetrahydropyranyl.

In additional embodiments, the present invention is directed to one or more compounds of formula (I) independently selected from the group consisting of 2-(2-Cyclohexyl-vinyl)-5-(2-trifluoromethoxy-phenyl)-1H-benzimidazole;
2-(2-Cyclohexyl-vinyl)-5-phenyl-1H-benzimidazole;
2-(2-Cyclohexyl-vinyl)-5-o-tolyl-1H-benzimidazole;
2-(2-Cyclohexyl-vinyl)-5-[2-(2,2,2-trifluoro-ethoxy)-phenyl]-1H-benzimidazole;
3-[2-(2-Cyclohexyl-vinyl)-1H-benzimidazol-5-yl]-phenol;
2-[2-(2-Cyclohexyl-vinyl)-1H-benzimidazol-5-yl]-phenyl}-methanol;
2-(2-Cyclohexyl-vinyl)-5-[2-(2-methyl-[1,3]dioxolan-2-yl)-phenyl]-1H-benzimidazole;
1-{2-[2-(2-Cyclohexyl-vinyl)-1H-benzimidazol-5-yl]-phenyl}-ethanone;
5-(2-Chloro-5-fluoro-phenyl)-2-(2-cyclohexyl-vinyl)-1H-benzimidazole;
5-(2-Chloro-6-fluoro-phenyl)-2-(2-cyclohexyl-vinyl)-1H-benzimidazole;
2-(2-Cyclohexyl-vinyl)-5-(2-fluoro-6-methoxy-phenyl)-1H-benzimidazole;
2-(2-Cyclohexyl-vinyl)-5-(4-fluoro-2-methoxy-phenyl)-1H-benzimidazole;
2-(2-Cyclohexyl-vinyl)-5-(5-fluoro-2-methoxy-phenyl)-1H-benzimidazole;
2-(2-Cyclohexyl-vinyl)-5-(2,6-dimethoxy-phenyl)-1H-benzimidazole;
2-(2-Cyclohexyl-vinyl)-5-(2,6-difluoro-phenyl)-1H-benzimidazole;
2-(2-Cyclohexyl-vinyl)-5-(2-fluoro-phenyl)-1H-benzimidazole;
2-(2-Cyclohexyl-vinyl)-5-(3-methyl-thiophen-2-yl)-1H-benzimidazole;
5-(2-Chloro-5-methoxy-phenyl)-2-(2-cyclohexyl-vinyl)-1H-benzimidazole;
2-(2-Cyclohexyl-vinyl)-5-(2,5-dichloro-phenyl)-1H-benzimidazole;
5-(5-Chloro-2-methoxy-phenyl)-2-(2-cyclohexyl-vinyl)-1H-benzimidazole;
2-(2-Cyclohexyl-vinyl)-5-(2,5-dimethoxy-phenyl)-1H-benzimidazole;
2-(2-Cyclohexyl-vinyl)-5-(2,5-difluoro-phenyl)-1H-benzimidazole;
2-(2-Cyclopentyl-vinyl)-5-(2-fluoro-phenyl)-1H-benzimidazole;
2-(2-Cyclopentyl-vinyl)-5-(3-methyl-thiophen-2-yl)-1H-benzimidazole;
2-(2-Cyclopentyl-vinyl)-5-(2-trifluoromethoxy-phenyl)-1H-benzimidazole;
2-[2-(2-Cyclopentyl-vinyl)-1H-benzimidazol-5-yl]-benzonitrile;
{2-[2-(2-Cyclopentyl-vinyl)-1H-benzimidazol-5-yl]-phenyl}-methanol;
1-{2-[2-(2-Cyclopentyl-vinyl)-1H-benzimidazol-5-yl]-phenyl}-ethanone;
2-[2-(4,4-Difluoro-cyclohexyl)-vinyl]-5-(2-trifluoromethyl-phenyl)-1H-benzimidazole;

2-[2-(4,4-Difluoro-cyclohexyl)vinyl]-5-(2-fluoro-6-trifluoromethyl-phenyl)-1H-benzimidazole;

2-[2-(4-Fluoro-cyclohex-3-enyl)-vinyl]-5-(2-trifluoromethyl-phenyl)-1H-benzoimidazole;

2-[2-(4-Fluoro-cyclohex-3-enyl)-vinyl]-5-(2-trifluoromethoxy-phenyl)-1H-benzoimidazole;

2-[2-(4-Fluoro-cyclohex-3-enyl)-vinyl]-5-(5-fluoro-2-methoxy-phenyl)-1H-benzoimidazole;

5-(2-Chloro-phenyl)-2-[2-(4-fluoro-cyclohex-3-enyl)-vinyl]-1H-benzoimidazole;

5-(2,6-Dimethyl-phenyl)-2-[2-(4-fluoro-cyclohex-3-enyl)-vinyl]-1H-benzoimidazole;

2-[2-(4-Fluoro-cyclohex-3-enyl)-vinyl]-5-(2-fluoro-phenyl)-1H-benzoimidazole;

2-[2-(4,4-Difluoro-cyclohexyl)-vinyl]-5-(2-trifluoromethoxy-phenyl)-1H-benzoimidazole;

5-(2-Chloro-phenyl)-2-[2-(4,4-difluoro-cyclohexyl)-vinyl]-1H-benzoimidazole;

2-[2-(4,4-Difluoro-cyclohexyl)-vinyl]-5-(2-fluoro-phenyl)-1H-benzoimidazole;

5-(2,6-Dimethoxy-phenyl)-2-[2-(4-fluoro-cyclohex-3-enyl)-vinyl]-1H-benzoimidazole;

2-[2-(4-Fluoro-cyclohex-3-enyl)-vinyl]-5-(2-fluoro-6-methoxy-phenyl)-1H-benzoimidazole;

2-[2-(4,4-Difluoro-cyclohexyl)-vinyl]-5-(2-fluoro-6-trifluoromethyl-phenyl)-1H-benzoimidazole;

2-[2-(4,4-Difluoro-cyclohexyl)-vinyl]-5-(2,6-dimethoxy-phenyl)-1H-benzoimidazole;

2-[2-(4,4-Difluoro-cyclohexyl)-vinyl]-5-(2-fluoro-6-methoxy-phenyl)-1H-benzoimidazole;

2-[2-(4,4-Difluoro-cyclohexyl)-vinyl]-5-(5-fluoro-2-methoxy-phenyl)-1H-benzoimidazole;

2-[2-(4-Fluoro-cyclohex-3-enyl)-vinyl]-7-trifluoromethyl-5-(2-trifluoromethyl-phenyl)-1H-benzoimidazole;

2-[2-(4,4-Difluoro-cyclohexyl)-vinyl]-7-trifluoromethyl-5-(2-trifluoromethyl-phenyl)-1H-benzoimidazole;

2-(2-Cyclohexyl-vinyl)-7-methyl-5-(2-trifluoromethoxy-phenyl)-1H-benzoimidazole;

2-(2-Cyclohexyl-vinyl)-7-methyl-5-(2-trifluoromethyl-phenyl)-1H-benzoimidazole;

(E)-2-[2-(Tetrahydro-pyran-4-yl)-vinyl]-5-(2-trifluoromethyl-phenyl)-1H-benzimidazole;

(E)-2-[2-(Tetrahydro-thiopyran-4-yl)-vinyl]-5-(2-trifluoromethyl-phenyl)-1H-benzimidazole;

(E)-5-(2-Fluoro-phenyl)-2-[2-(tetrahydro-pyran-4-yl)-vinyl]-1H-benzimidazole;

(E)-7-Methyl-2-[2-(tetrahydro-pyran-4-yl)-vinyl]-5-(2-trifluoromethyl-phenyl)-1H-benzimidazole;

(E)-2-[2-(Tetrahydro-pyran-4-yl)-vinyl]-5-(2-trifluoromethyl-pyridin-4-yl)-1H-benzimidazole;

(E)-2-(2-Cyclohexyl-vinyl)-5-(2-trifluoromethyl-pyridin-4-yl)-1H-benzimidazole;

(E)-2-(2-Cyclohexyl-vinyl)-5-(2-trifluoromethyl-pyridin-3-yl)-1H-benzimidazole;

(E)-2-(2-Cyclohexyl-vinyl)-5-(2-fluoro-6-trifluoromethyl-phenyl)-1H-benzimidazole;

(E)-5-(2,6-Bis-trifluoromethyl-phenyl)-2-(2-cyclohexyl-vinyl)-1H-benzimidazole;

(E)-2-(2-Cyclohexyl-vinyl)-5-(2-fluoro-6-trifluoromethoxy-phenyl)-1H-benzimidazole;

(E)-2-(2-Cyclohexyl-vinyl)-5-(3-trifluoromethyl-pyridin-2-yl)-1H-benzimidazole;

(E)-5-(2,6-Difluoro-phenyl)-2-[2-(tetrahydro-pyran-4-yl)-vinyl]-1H-benzimidazole;

(E)-2-[2-(Tetrahydro-pyran-4-yl)-vinyl]-5-(3-trifluoromethyl-pyridin-2-yl)-1H-benzoimidazole;

(E)-2-[2-(4,4-Dimethyl-cyclohexyl)-vinyl]-7-methyl-5-(2-trifluoromethyl-phenyl)-1H-benzoimidazole;

(E)-2-[2-(4,4-Dimethyl-cyclohexyl)-vinyl]-5-(2-trifluoromethyl-phenyl)-1H-benzoimidazole;

(E)-5-(2,6-Difluoro-phenyl)-2-[2-(4,4-dimethyl-cyclohexyl)-vinyl]-1H-benzoimidazole;

(E)-2-[2-(4-Methyl-tetrahydro-pyran-4-yl)-vinyl]-5-(2-trifluoromethyl-phenyl)-1H-benzimidazole;

(E)-5-(2,6-Bis-trifluoromethyl-phenyl)-2-[2-(4-methyl-tetrahydro-pyran-4-yl)-vinyl]-1H-benzimidazole;

(E)-2-(2-Cyclohexyl-propenyl)-5-(2-trifluoromethyl-phenyl)-1H-benzimidazole;

(E)-2-(2-Cyclohexyl-propenyl)-5-(2-trifluoromethyl-phenyl)-1H-benzimidazole;

(E)-2-[2-(4-Bromo-bicyclo[2.2.2]oct-1-yl)-vinyl]-5-(2-trifluoromethyl-phenyl)-1H-benzimidazole;

2-(2-Cyclohexyl-vinyl)-5-(2-trifluoromethyl-phenyl)-1H-benzoimidazole;

and solvates, hydrates, tautomers and pharmaceutically acceptable salts thereof.

In additional embodiments, the present invention is directed to one or more compounds selected from the group consisting of 2-(2-cyclohexyl-vinyl)-5-(2-trifluoromethoxy-phenyl)-1H-benzimidazole;

2-[2-(4,4-difluoro-cyclohexyl)-vinyl]-5-(2-trifluoromethyl-phenyl)-1H-benzimidazole;

(E)-2-[2-(tetrahydro-pyran-4-yl)-vinyl]-5-(2-trifluoromethyl-phenyl)-1H-benzimidazole;

(E)-5-(2,6-bis-trifluoromethyl-phenyl)-2-(2-cyclohexyl-vinyl)-1H-benzimidazole;

(E)-2-(2-cyclohexyl-vinyl)-5-(2-fluoro-6-trifluoromethoxy-phenyl)-1H-benzimidazole;

2-(2-cyclohexyl-vinyl)-5-(2-trifluoromethyl-phenyl)-1H-benzimidazole;

and solvates, hydrates, tautomers and pharmaceutically acceptable salts thereof.

Additional embodiments of the present invention, include those wherein the substituents selected for one or more of the variables defined herein (i.e. $R^1$, $R^2$, $R^3$,

Ⓐ, Ⓑ, etc.) are independently selected to be any individual substituent or any subset of substituents selected from the complete list as defined herein. In another embodiment of the present invention is any single compound or subset of compounds selected from the representative compounds listed in Tables 1-3, below. Representative compounds of the present invention are as listed in Tables 1-3, below.

TABLE 1

Representative Compounds of Formula (I)

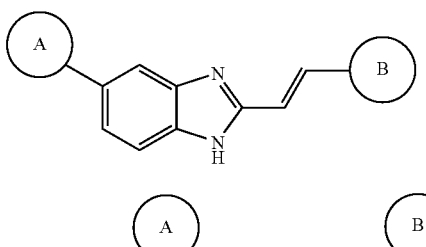

| ID No. | A | B |
|---|---|---|
| 1 | 2-trifluoromethoxy-phenyl | cyclohexyl |
| 2 | phenyl | cyclohexyl |
| 3 | 2-methylphenyl | cyclohexyl |
| 4 | 2-(2,2,2-trifluoro-ethoxy)-phenyl | cyclohexyl |
| 5 | 3-hydroxyphenyl | cyclohexyl |
| 6 | 2-hydroxymethyl-phenyl | cyclohexyl |
| 7 | 2-(2-(2-methyl-[1,3]dioxolanyl))-phenyl | cyclohexyl |
| 8 | 2-(methylcarbonyl)-phenyl | cyclohexyl |
| 9 | 2-chloro-5-fluoro-phenyl | cyclohexyl |
| 10 | 2-chloro-6-fluoro-phenyl | cyclohexyl |
| 11 | 2-trifluoromethoxy-6-fluoro-phenyl | cyclohexyl |
| 12 | 2-methoxy-4-fluoro-phenyl | cyclohexyl |
| 13 | 2-trifluoromethoxy-5-fluoro-phenyl | cyclohexyl |
| 14 | 2,6-dimethoxy-phenyl | cyclohexyl |
| 15 | 2,6-difluorophenyl | cyclohexyl |
| 16 | 2-fluorophenyl | cyclohexyl |
| 17 | 2-(3-methyl-thienyl) | cyclohexyl |
| 18 | 2-chloro-5-methoxy-phenyl | cyclohexyl |
| 19 | 2,5-dichlorophenyl | cyclohexyl |
| 20 | 3-chloro-6-methoxy-phenyl | cyclohexyl |
| 21 | 2,4-dimethoxy-phenyl | cyclohexyl |
| 22 | 2,5-dimethoxy-phenyl | cyclohexyl |
| 23 | 2,5-difluoro-phenyl | cyclohexyl |
| 24 | 2-fluorophenyl | cyclopentyl |
| 25 | 2-(3-methyl-thienyl) | cyclopentyl |
| 26 | 2-trifluoromethoxy-phenyl | cyclopentyl |
| 27 | 2-cyanophenyl | cyclopentyl |
| 28 | 2-hydroxymethyl-phenyl | cyclopentyl |
| 29 | 2-methylcarbonyl-phenyl | cyclopentyl |
| 30 | 2-trifluoromethyl-phenyl | 1-(4,4,-difluoro-cyclohexyl) |
| 31 | 2-trifluoromethyl-phenyl | 4-(1-fluoro-cyclohexenyl) |
| 32 | 2-trifluoromethoxy-phenyl | 4-(1-fluoro-cyclohexenyl) |
| 33 | 3-fluoro-6-methoxy-phenyl | 4-(1-fluoro-cyclohexenyl) |
| 34 | 2-chlorophenyl | 4-(1-fluoro-cyclohexenyl) |
| 35 | 2,6-dimethyl-phenyl | 4-(1-fluoro-cyclohexenyl) |
| 36 | 2-fluorophenyl | 4-(1-fluoro-cyclohexenyl) |
| 37 | 2-trifluoromethoxy-phenyl | 1-(4,4-difluoro-cyclohexyl) |
| 38 | 2-chlorophenyl | 1-(4,4-difluoro-cyclohexyl) |
| 39 | 2-fluorophenyl | 1-(4,4-difluoro-cyclohexyl) |
| 40 | 2,6-dimethoxy-phenyl | 4-(1-fluoro-cyclohexenyl) |
| 41 | 2-fluoro-6-methoxy-phenyl | 4-(1-fluoro-cyclohexenyl) |
| 42 | 2-fluoro-6-trifluoromethyl-phenyl | 1-(4,4-difluoro-cyclohexyl) |
| 43 | 2,6-dimethoxy-phenyl | 1-(4,4-difluoro-cyclohexyl) |
| 44 | 2-fluoro-6-trifluoromethoxy-phenyl | 1-(4,4-difluoro-cyclohexyl) |
| 45 | 3-fluoro-6-methoxy-phenyl | 1-(4,4-difluoro-cyclohexyl) |
| 50 | 2-trifluoromethyl-phenyl | 4-tetrahydro-pyranyl |
| 51 | 2-trifluoromethyl-phenyl | 4-tetrahydro-thiopyranyl |
| 52 | 2-fluorophenyl | 4-tetrahydro-pyranyl |
| 54 | 4-(3-trifluoromethyl-pyridyl) | 4-tetrahydro-pyranyl |

TABLE 1-continued

Representative Compounds of Formula (I)

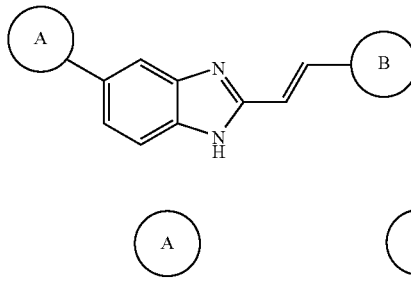

| ID No. | A | B |
|---|---|---|
| 55 | 4-(3-trifluoromethyl-pyridyl) | cyclohexyl |
| 56 | 3-(2-trifluoromethyl-pyridyl) | cyclohexyl |
| 57 | 2-fluoro-6-trifluoromethyl-phenyl | cyclohexyl |
| 58 | 2,6-di(trifluoromethyl)-phenyl | cyclohexyl |
| 59 | 2-fluoro-6-trifluoromethoxy-phenyl | cyclohexyl |
| 60 | 2-(6-trifluoromethyl-pyridyl) | cyclohexyl |
| 61 | 2,6-difluoro-phenyl | 4-tetrahydro-pyranyl |
| 62 | 2-(3-trifluoromethyl-pyridyl) | 4-tetrahydro-pyranyl |
| 64 | 2-trifluoromethyl-phenyl | 1-(4,4-dimethyl-cyclohexyl) |
| 65 | 2,6-difluoro-phenyl | 1-(4,4-dimethyl-cyclohexyl) |
| 70 | 2-trifluoromethyl-phenyl | 4-(1-bromo-bicyclo[2.2.2]octanyl) |
| 71 | 2-trifluoromethyl-phenyl | cyclohexyl |

TABLE 2

Representative Compounds of Formula (I)

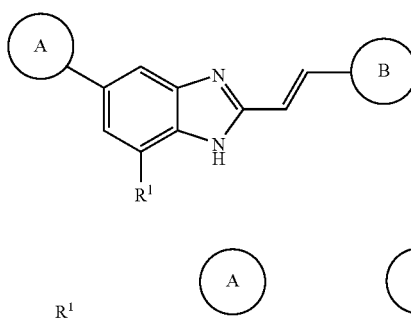

| ID No. | R¹ | A | B |
|---|---|---|---|
| 46 | trifluoromethyl | 2-trifluoromethyl-phenyl | 4-(1-fluoro-cyclohexenyl) |
| 47 | trifluoromethyl | 2-trifluoromethyl-phenyl | 1-(4,4-difluoro-cyclohexyl) |
| 48 | methyl | 2-trifluoromethoxy-phenyl | cyclohexyl |
| 49 | methyl | 2-trifluoromethyl-phenyl | cyclohexyl |
| 53 | methyl | 2-trifluoromethyl-phenyl | 4-tetrahydro-pyranyl |
| 63 | methyl | 2-trifluoromethyl-phenyl | 1-(4,4-dimethyl-cyclohexyl) |

TABLE 3

Representative Compounds of Formula (I)

| ID No. | $R^2$ | $R^3$ | A | B |
|---|---|---|---|---|
| 66 | H | methyl | 2-trifluoromethyl-phenyl | 4-tetrahydro-pyranyl |
| 67 | H | methyl | 2,6-di(trifluoromethyl)-phenyl | 4-tetrahydro-pyranyl |
| 68 | H | methyl | 2-trifluoromethyl-phenyl | 1-(4,4-difluoro-cyclohexyl) |
| 69 | methyl | H | 2-trifluoromethyl-phenyl | cyclohexyl |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. Similarly, the term "$C_{X-Y}$alkyl" wherein X and Y are integers shall indicate an alkyl group as herein define containing between X and Y carbon atoms. For example, the term "$C_{1-2}$alkyl" shall indicate an alkyl chain containing one to two carbon atoms, more particularly, methyl and ethyl.

As used herein, unless otherwise noted, the term "halogenated lower alkyl" shall mean any lower alkyl group as defined above substituted with at least one halogen atom, preferably substituted with a least one fluoro atom. Suitable examples include but are not limited to —$CF_3$, —$CH_2$—$CF_3$, —$CF_2$—$CF_2$—$CF_2$—$CF_3$, —$CCl_3$, —$CH_2CCl_3$, and the like. Similarly, the term "fluorinated lower alkyl" shall mean any lower alkyl group as defined above substituted with at least one fluoro atom. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted alkyl" shall mean alkyl group as defined above substituted with at least one hydroxy group. Preferably, the alkyl group is substituted with one hydroxy group. Preferably, the alkyl group is substituted with a hydroxy group at the terminal carbon. Suitable examples include, but are not limited to, —$CH_2(OH)$, —$CH_2$—$CH_2(OH)$, —$CH_2$—$CH(OH)$—$CH_2$, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{X-Y}$alkoxy" wherein X and Y are integers shall indicate an alkoxy group as herein define containing between X and Y carbon atoms. For example, the term "$C_{1-2}$alkoxy" shall indicate an alkyl chain containing one to two carbon atoms, more particularly, methoxy and ethoxy.

As used herein, unless otherwise noted, the term "halogenated lower alkoxy" shall mean any lower alkoxy group as defined above substituted with at least one halogen atom, preferably substituted with a least one fluoro atom. Suitable examples include but are not limited to —$OCF_3$, —$OCH_2$—$CF_3$, —$OCF_2$—$CF_2$—$CF_2$—$CF_3$, —$OCCl_3$, —$OCH_2$—$CCl_3$, and the like. Similarly, the term "fluorinated lower alkoxy" shall mean any lower alkyl group as defined above substituted with at least one fluoro atom. Suitable examples include but are not limited to —$OCF_3$, —$OCH_2$—$CF_3$, —$OCF_2$—$CF_2$—$CF_2$—$CF_3$, and the like.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl-$C_1$-$C_6$alkyl-amino-carbonyl-$C_1$-$C_6$alkyl" substituent refers to a group of the formula

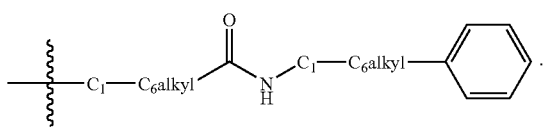

Abbreviations used in the specification, particularly the Schemes and Examples, are as follows:

| | |
|---|---|
| BSA = | Bovine Serum Albumin |
| BuLi = | Butyl Lithium |
| CSA = | Camphorsulfonic Acid |
| DAST = | Diethylaminosulfur trifluoride |
| DCM = | Dichloromethane |
| DIBAL-H = | Diisobutylammonium hydride |
| DME = | 1,2-Dimethoxyethane |
| DMEM = | Dulbecco's Modified Eagle Medium |
| DMF = | N,N-Dimethylformamide |
| DMSO = | Dimethylsulfoxide |
| EGTA = | Ethylene Glycol-O,O'-bis(2-aminoethyl)-N,N,N',N'-tetracetic acid |
| EtOAc = | Ethyl acetate |
| EtOH = | Ethanol |
| FBS = | Fetal Bovine Serum |
| HEPES = | 4-(2-Hydroxyethyl)-1-Piperizine Ethane Sulfonic Acid |
| HPLC = | High Pressure Liquid Chromatography |
| HPMC = | Hydroxypropyl Methylcellulose |
| i-PrOH = | Isopropanol |
| KOAc = | Potassium Acetate |
| KO-t-Bu = | Potassium tert-Butoxide |
| LAH = | Lithium Aluminum Hydride |
| MeOH = | Methanol |
| PCC = | Pyridinium Dichromate |
| PdCl$_2$dppf or = (dppf)PdCl$_2$ | [1,1'-Bis(diphenylphosphino)ferrocene] Dichloropalladium(II). |
| Pd$_2$(dba)$_3$ = | Tris(dibenzylidene acetone)dipalladium(0) |
| Pd(PPh$_3$)$_4$ = | Tetrakistriphenylphosphine palladium (0) |
| TFA = | Trifluoroacetic Acid |
| THF = | Tetrahydrofuran |
| TRP M8 = | Transient Receptor Potential M8 channel |

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For the purposes of the present invention, the term "antagonist" is used to refer to a compound capable of producing, depending on the circumstance, a functional antagonism of an ion channel, including but not limited to competitive antagonists, non-competitive antagonists, desensitizing agonists, and partial agonists.

For purposes of the present invention, the term "TRPM8-modulated" is used to refer to the condition of being affected by the modulation of the TRPM8 receptor, including but not limited to, the state of being mediated by the TRPM8 receptor.

As used herein, unless otherwise noted, the term "inflammatory pain" shall include pain due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, and arachnoiditis.

As used herein, unless otherwise noted "inflammatory hyperalgesia" shall include inflammatory hyperplasia due to inflammation, osteoarthritis, rheumatoid arthritis, back pain, joint pain, abdominal pain, musculoskeletal diseases, skin diseases, post operative pain, headaches, fibromyalgia, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, Crohn's Disease, and ulcerative colitis.

As used herein, unless otherwise noted, the term "inflammatory hypersensitivity" is used to refer to a condition that is characterized by one or more hallmarks of inflammation, including but not limited to edema, erythema, hyperthermia and pain, and/or by an exaggerated physiologic or pathophysiologic response to one or more than one type of stimulation, including but not limited to thermal, mechanical and/or chemical stimulation.

As used herein, unless otherwise noted "neuropathic pain" shall include neuropathic pain due to cancer, a neurological disorder, spine or peripheral nerve surgery, a brain tumor, traumatic brain injury (TBI), spinal cord trauma, a chronic pain syndrome, fibromyalgia, chronic fatigue syndrome, a neuralgia, lupus, sarcoidosis, peripheral neuropathy, bilateral peripheral neuropathy, diabetic neuropathy, central pain, neuropathies associated with spinal cord injury, stroke, ALS, Parkinson's disease, multiple sclerosis, sciatic neuritis, mandibular joint neuralgia, peripheral neuritis, polyneuritis, stump pain, phantom limb pain, a bony fracture, oral neuropathic pain, Charcot's pain, complex regional pain syndrome I and II (CRPS I/II), radiculopathy, Guillain-barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia and vidian neuralgia.

As used herein, unless otherwise noted, the term "neuropathic cold allodynia" shall include neuropathic cold allodynia arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II), and radiculopathy.

As used herein, unless otherwise noted, the term "anxiety" shall include social anxiety, post traumatic stress disorder, phobias, social phobia, special phobias, panic disorder, obsessive compulsive disorder, acute stress disorder, separation anxiety disorder, and generalized anxiety disorder.

As used herein, unless otherwise noted, the term "depression" shall include major depression, bipolar disorder, seasonal affective disorder, post natal depression, manic depression, and bipolar depression.

As used herein, unless otherwise noted, the term "cardiovascular disease aggravated by cold" shall include peripheral vascular disease, vascular hypertension, pulmonary hypertension, Raynaud's disease and coronary artery disease.

In an embodiment, the present invention is further directed to methods for the treatment of inflammatory pain, inflammatory hypersensitivity condition, neuropathic pain, anxiety and depression.

In an embodiment of the present invention, the inflammatory pain is pain due to inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, sinus headache, tension headache, or arachnoiditis. Preferably, the inflammatory pain is inflammatory hyperalgesia.

In another embodiment of the present invention, the inflammatory hyperalgesia is inflammatory somatic hyperalgesia or inflammatory visceral hyperalgesia.

In another embodiment, the present invention is directed to methods for the treatment of inflammatory hyperplasia, wherein the inflammatory hyperalgesia is due to inflammation, osteoarthritis, rheumatoid arthritis, back pain, joint pain, abdominal pain, musculoskeletal diseases, skin diseases, post operative pain, headaches, fibromyalgia, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, Crohn's Disease, or ulcerative colitis.

In another embodiment, the present invention is directed to methods of treating inflammatory hypersensitivity conditions, wherein the inflammatory hypersensitivity condition is urinary incontinence, benign prostatic hypertrophy, cough, asthma, rhinitis, nasal hypersensitivity, itch, contact dermatitis, dermal allergy, or chronic obstructive pulmonary disease.

In another embodiment, the present invention is directed to methods for the treatment of neuropathic pain, wherein the neuropathic pain is due to cancer, a neurological disorder, spine or peripheral nerve surgery, a brain tumor, traumatic brain injury (TBI), spinal cord trauma, a chronic pain syndrome, fibromyalgia, chronic fatigue syndrome, a neuralgia, lupus, sarcoidosis, peripheral neuropathy, bilateral peripheral neuropathy, diabetic neuropathy, central pain, neuropathies associated with spinal cord injury, stroke, ALS, Parkinson's disease, multiple sclerosis, sciatic neuritis, mandibular joint neuralgia, peripheral neuritis, polyneuritis, stump pain, phantom limb pain, a bony fracture, oral neuropathic pain, Charcot's pain, complex regional pain syndrome I and II (CRPS I/II), radiculopathy, Guillain-barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vulvodynia or vidian neuralgia. Preferably, the neuropathic pain is neuropathic cold allodynia or neuralgia. Preferably, the neuralgia is trigeminal neuralgia, glossopharyngeal neuralgia, postherpetic neuralgia, or causalgia.

In another embodiment, the present invention is directed to methods for the treatment of neuropathic cold allodynia, wherein the neuropathic cold allodynia is pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II), or radiculopathy.

In another embodiment, the present invention is directed to methods for the treatment of anxiety, wherein the anxiety is social anxiety, post traumatic stress disorder, phobias, social phobia, special phobias, panic disorder, obsessive compulsive disorder, acute stress disorder, separation anxiety disorder, or generalized anxiety disorder.

In another embodiment, the present invention is directed to methods for the treatment of depression wherein the depression is major depression, bipolar disorder, seasonal affective disorder, post natal depression, manic depression, or bipolar depression.

In another embodiment, the present invention is directed to a method for the treatment of inflammatory somatic hyperalgesia in which a hypersensitivity to thermal stimuli exists. In another embodiment, the present invention is directed to a method for the treatment of inflammatory visceral hyperalgesia in which an enhanced visceral irritability exists. In another embodiment, the present invention is directed to a method for the treatment of neuropathic cold allodynia in which a hypersensitivity to cooling stimuli exists.

In another embodiment, the present invention is directed to a method for the treatment of cardiovascular disease aggravated by cold, including peripheral vascular disease, vascular hypertension, pulmonary hypertension, Raynaud's disease and coronary artery disease.

In another embodiment, the present invention is directed to methods for the treatment and/or prevention of migraine, post herpetic neuralgia, post traumatic neuralgia, post chemotherapy neuralgia, complex regional pain syndrome I and II (CRPS I/II), fibromyalgia, inflammatory bowel disease, pruritis, asthma, chronic obstructive pulmonary disease, toothache, bone pain or pyresis in a mammal, which method comprises administering to a mammal in need of such treatment or prevention a therapeutically effective amount of a TRPM8 antagonist.

In another embodiment, the present invention is directed to methods for the treatment and/or prevention of hypertension, peripheral vascular disease, Raynaud's disease, reperfusion injury or frostbite in a mammal, which method comprises administering to a mammal in need of such treatment or prevention a therapeutically effective amount of a TRPM8 antagonist.

In yet another embodiment, the present invention is directed to methods for accelerating post-anesthetic recovery or post hypothermia recovery in a mammal, which method comprises administering to a mammal in need of such treatment a therapeutically effective amount of a TRPM8 antagonist.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base.

The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

One embodiment of the present invention is directed to a composition comprising the dextrorotatory enantiomer of a compound of formula (I) wherein said composition is substantially free from the levorotatory isomer of said compound. In the present context, substantially free means less than 25%, preferably less than 10%, more preferably less than 5%, even more preferably less than 2% and even more preferably less than 1% of the levorotatory isomer calculated as.

$$\% \text{ dextrorotatory} = \frac{(\text{mass dextrorotatory})}{(\text{mass dextrorotatory}) + (\text{mass levorotatory})} \times 100$$

Another embodiment of the present invention is a composition comprising the levorotatory enantiomer of a compound of formula (I) wherein said composition is substantially free from the dextrorotatory isomer of said compound. In the present context, substantially free from means less than 25%, preferably less than 10%, more preferably less than 5%, even more preferably less than 2% and even more preferably less than 1% of the dextrorotatory isomer calculated as $$\% \text{ levorotatory} = \frac{(\text{mass levorotatory})}{(\text{mass dextrorotatory}) + (\text{mass levorotatory})} \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium, camsylate, carbonate, chloride, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1, below.

Scheme 1

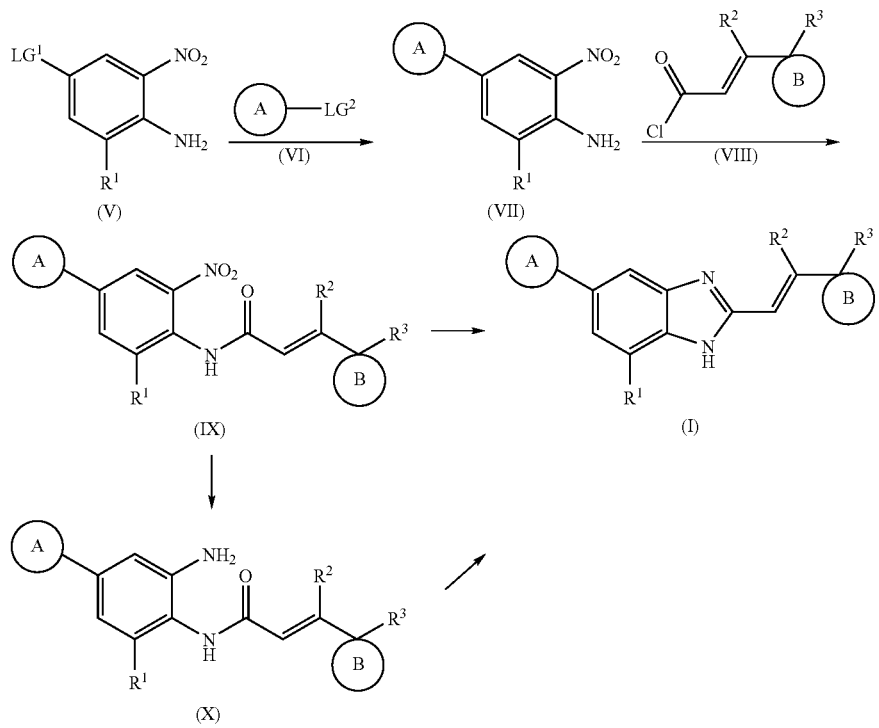

Accordingly, a suitably substituted compound of formula (V), wherein LG¹ is a first suitably selected leaving group such as —B(OH)₂ (e.g. the corresponding boronic acid),

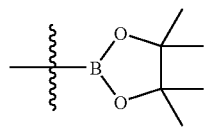

(e.g. a corresponding boronate ester) and the like, a known compound or compound prepared by known methods, is reacted with a suitably substituted compound of formula (VI), wherein LG² is a second suitably selected leaving group such as Br, Cl, I, and the like; in the presence of an inorganic base such as sodium carbonate, cesium carbonate, potassium phosphate, and the like; in the presence of a suitably selected catalyst such as Pd(PPh₃)₄, (dppf)PdCl₂.DCM, Pd₂(dba)₃, and the like; in an organic solvent or mixture of organic solvents such as DME, 1,4-dioxane, a mixture of DME and water, ethanol, and the like; preferably at a temperature in the range of from about room temperature to about 120° C., to yield the corresponding compound of formula (VII).

One skilled in the art will recognize that the coupling reaction may alternatively be carried out by reacting a compound of compound of formula (V) wherein LG¹ is a suitable leaving group such as Cl, Br, I, and the like, with a compound of formula (VI), wherein LG² a suitably selected leaving group such as —B(OH)₂ (e.g. the corresponding boronic acid),

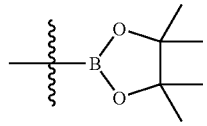

(e.g. a corresponding boronate ester) and the like.

The compound of formula (VII) (or its corresponding anion prepared by reacting the compound of formula (VII) with a base such as NaH, LiH, KO-t-Bu, and the like, in an organic solvent such as DMF, THF, DCM, and the like) is reacted with a suitably substituted compound of formula (VIII), a known compound or compound prepared by known methods; in an organic solvent such as DMF, THF, DCM, and the like, to yield the corresponding compound of formula (IX).

The compound of formula (IX) is cyclized by reacting with a suitably selected reducing agent such as iron powder, tin powder, zinc powder, and the like; in the presence of an acid such as acetic acid, hydrochloric acid, and the like; neat or in an organic solvent such as ethanol, methanol, 1,4-dioxane, and the like; preferably at a temperature in the range of from about 50° C. to about 80° C.; to yield the corresponding compound of formula (I).

Alternatively, the compound of formula (IX) is reacted with a suitably selected reducing agent such as hydrogen gas in the presence of a palladium catalyst, iron or zinc powder in the presence of an acid such as acetic acid, hydrochloric acid, and the like, or in the presence of iron and ammonium chloride; neat or in an organic solvent such as ethanol, methanol, 1,4-dioxane, and the like; preferably at a n elevated temperature in the range of from about 50° C. to about 80° C.; to yield the corresponding compound of formula (X).

The compound of formula (X) is reacted with a suitably selected acid such as acetic acid, tosic acid, CSA, and the like; in an organic solvent such as toluene, 1,4-dioxane, THF, and the like; preferably at a temperature in the range of form about room temperature to about 120° C.; to yield the corresponding compound of formula (I).

Compounds of formula (I) may alternatively be prepared according to the process outlined in Scheme 2, below.

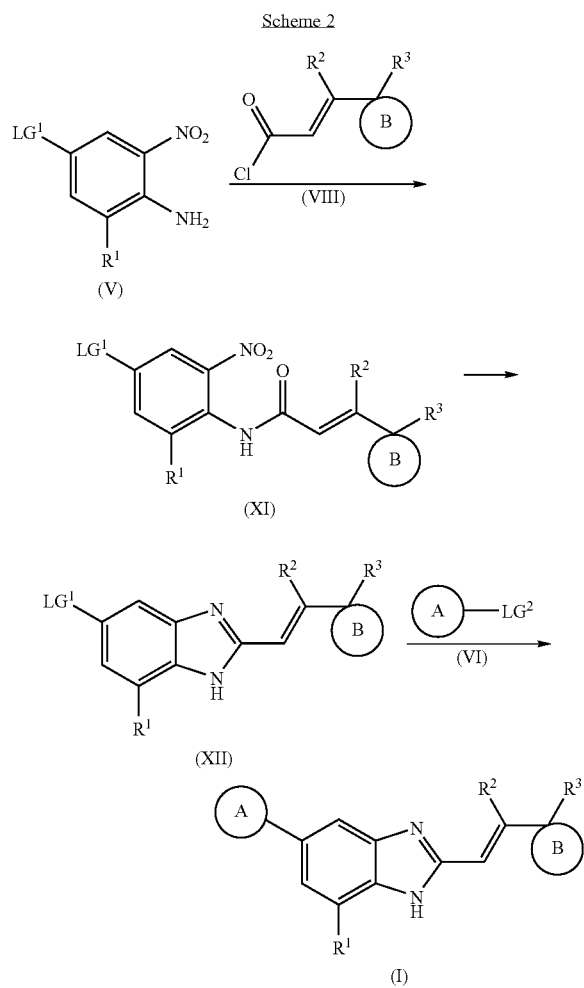

Accordingly, a suitably substituted compound of formula (V) (or its corresponding anion prepared by reacting the compound of formula (V) with a base such as NaH, LiH, KO-t-Bu, and the like, in an organic solvent such as DMF, THF, DCM, and the like), wherein $LG^1$ is a first suitably selected leaving group such as Cl, Br, I, and the like, preferably Br, a known compound or compound prepared by known methods, is reacted with a suitably substituted compound of formula (VIII), a known compound or compound prepared by known methods; in an organic solvent such as DMF, THF, DCM, and the like, to yield the corresponding compound of formula (XI).

The compound of formula (XI) is cyclized via a one-step or two-step process as outlined in detail in Scheme 1 above. Briefly, the compound of formula (XI) is reacted with a suitably selected reducing agent such as iron powder, zinc powder, tin powder, and the like; in the presence of an acid such as acetic acid, hydrochloric acid, and the like; neat or in an organic solvent such as ethanol, methanol, THF, and the like; preferably at a temperature in the range of from about room temperature to about 120° C.; to yield the corresponding compound of formula (XII).

Alternatively, the compound of formula (XI) is reacted with a suitably selected reducing agent such as hydrogen gas in the presence of a palladium catalyst, iron or zinc powder in the presence of an acid such as acetic acid, hydrochloric acid, and the like, or in the presence of iron and ammonium chloride; neat or in an organic solvent such as ethanol, methanol, THF, and the like; preferably at a temperature in the range of from about room temperature to about 120° C.; and then reacted with a suitably selected acid such as acetic acid, tosic acid, CSA, and the like; in an organic solvent such as toluene, THF, 1,4-dioxane, and the like; preferably at a temperature in the range of form about room temperature to about 120° C.; to yield the corresponding compound of formula (XII).

The compound of formula (XII) is reacted with a suitably substituted compound of formula (VI), wherein $LG^2$ is a suitably selected second leaving group such as $—B(OH)_2$ (e.g. the corresponding boronic acid),

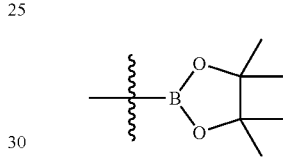

(e.g. a corresponding boronate ester) and the like; in the presence of an inorganic base such as sodium carbonate, cesium carbonate, potassium phosphates, and the like; in the presence of a suitably selected catalyst such as $Pd(PPh_3)_4$, $(dppf)PdCl_2.DCM$, $Pd_2(dba)_3$, and the like; in an organic solvent or mixture of organic solvents such as DME, 1,4-dioxane, a mixture of DME and water, ethanol, and the like; preferably at a temperature in the range of from about 60° C. to about 120° C., to yield the corresponding compound of formula (I).

Compounds of formula (VIII) are known compounds or compounds which may be prepared according to known methods as would be readily known to those skilled in the art. The examples which follow herein further describe processes for the preparation of representative compounds of formula (VIII), which processes may be readily adapted by one skilled in the art to the preparation of additional compounds of formula (VIII). In another example, compounds of formula (VIII) may be prepared, for example, according to the process outlined in Scheme 3, below.

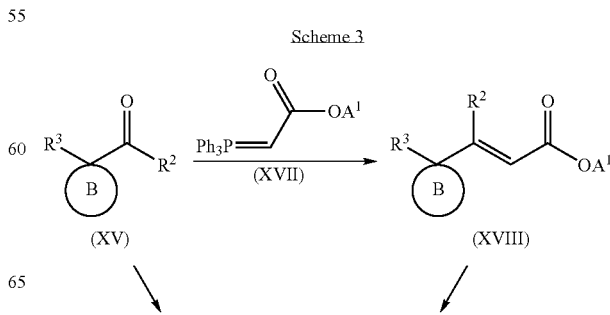

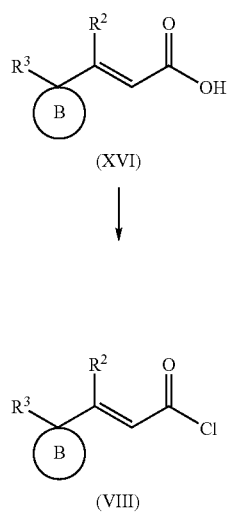

(XVI)

↓

(VIII)

Accordingly, a suitably substituted compound of formula (XV), a known compound or compound prepared by known methods, is reacted with malonic acid; in the presence of tertiary base such as piperidine, and the like; in an organic solvent such as pyridine, and the like; preferably at an elevated temperature in the range of from about 50° C. to about 100° C.; to yield the corresponding compound of formula (XVI).

Alternatively, a suitably substituted compound of formula (XV), a known compound or compound prepared by known methods, is reacted with a suitably substituted compound of formula (XVII), wherein $A^1$ is lower alkyl or phenyl, a known compound or compound prepared by known methods; to yield the corresponding compound of formula (XVIII).

The compound of formula (XVIII) is reacted with a suitably selected base such as NaOH, KOH, LiOH, and the like; in an aqueous organic solvent such as ethanol, methanol, 1,4-dioxane, and the like; to yield the corresponding compound of formula (XVI).

The compound of formula (XVI) is reacted with a suitably selected chlorinating agent such as thionyl chloride, oxalyl chloride, and the like; in the presence of a catalyst such as DMF, and the like; in an organic solvent such as DCM, DCE, 1,4-dioxane, and the like; to yield the corresponding compound of formula (VIII).

Compounds of formula (XV) are known compounds or compounds which may be prepared according to known methods as would be readily known to those skilled in the art. The examples which follow herein further describe processes for the preparation of representative compounds of formula (XV), which processes may be readily adapted by one skilled in the art to the preparation of additional compounds of formula (XV). In another example, compounds of formula (XV) wherein $R^3$ is hydrogen, may be prepared according to the process outlined in Scheme 4, below.

Scheme 4

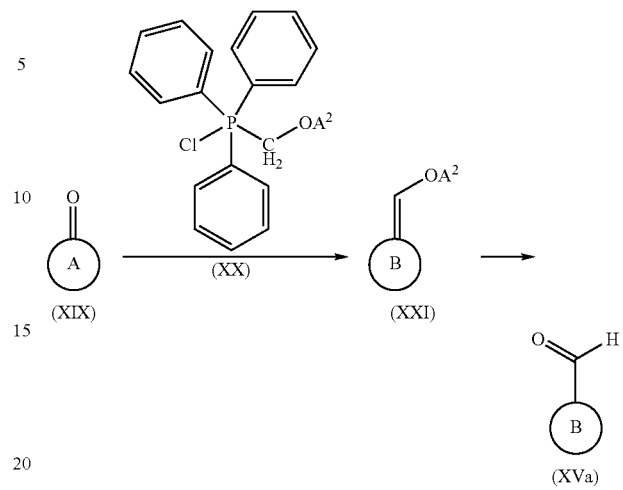

Accordingly, a suitably substituted compound of formula (XIX), a known compound or compound prepared by known methods, is reacted with a compound of formula (XX) (i.e. an alkoxymethyl triphenylphosphonium chloride), a known compound or compound prepared by known methods; in the presence of a suitably selected base such as LiHMDS, LDA, BuLi, KO-t-Bu, lithium tetramethylpiperidide, $NaNH_2$, and the like; in an organic solvent such as THF, ethyl ether, DME, and the like; preferably at a temperature in the range of from about −10° C. to about room temperature; to yield the corresponding compound of formula (XXI), The compound of formula (XXI) is reacted with a suitably selected acid such as formic acid, hydrochloric acid, sulfuric acid, and the like; neat or in an organic solvent such as THF, 1,4-dioxane, and the like; preferably at a temperature in the range of form about room temperature to about 100° C.; to yield the corresponding compound of formula (XVa).

In another example, compounds of formula (XV) wherein $R^3$ is other than hydrogen, may be prepared according to the process outlined in Scheme 5, below.

Scheme 5

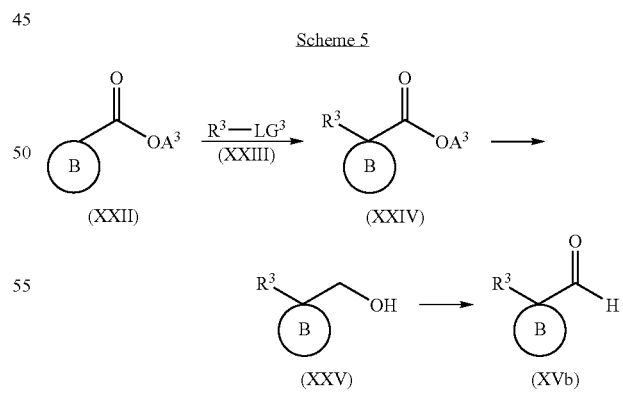

Accordingly, a suitably substituted compound of formula (XXII), wherein $A^3$ is lower alkyl or phenyl, a known compound or compound prepared by known methods, is reacted with a suitably substituted compound of formula (XXIII), wherein $LG^3$ is a suitably selected leaving group such as Cl, Br, I, tosylate, mesylate, and the like; in the presence of a suitably selected base such as potassium t-butoxide, sodium methoxide, sodium hydroxide, and the like; in an organic solvent such as ethanol, methanol, DMF, and the like; to yield the corresponding compound of formula (XXIV).

The compound of formula (XXIV) is reacted with a suitably selected reducing agent such as LAH, $BH_3$/THF, $LiAlH_4(OCH_3)_3$, and the like; in an organic solvent such as THF, DCM, diethyl ether, and the like; preferably at a temperature in the range of form about −78° C. to about 100° C.; to yield the corresponding compound of formula (XXV).

The compound of formula (XXV) is reacted with a suitably selected oxidizing agent such as PCC, Dess-Martin periodinane, and the like; in an organic solvent such as DCM, DCE, THF, and the like; preferably at a temperature in the range of form about −78° C. to about 80° C.; to yield the corresponding compound of formula (XVb).

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 to about 1000 mg or any amount or range therein, and may be given at a dosage of from about 0.01 to about 300 mg/kg/day, or any amount or range therein, preferably from about 0.5 to about 50 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating TRP M8 mediated disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 10 to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by TRP M8 is required.

The daily dosage of the products may be varied over a wide range from about 0.01 to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.5 to about 50.0 mg/kg of body weight per day, or any amount or range therein. More preferably, from about 1.0 to about 5.0 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

2-(2-Cyclohexyl-vinyl)-5-(2-trifluoromethoxy-phenyl)-1H-benzimidazole hydrochloride salt (Cpd. 1)

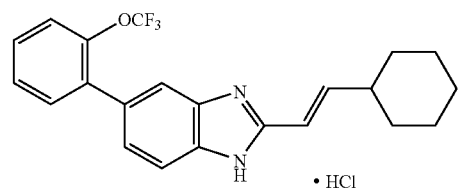

Step A: 3-Cyclohexyl-acrylic acid

A solution of malonic acid (30 g, 0.29 mol), cyclohexanecarbaldehyde (17.3 mL, 0.14 mol), and piperidine (2.9 mL, 0.029 mol) in pyridine (90 mL) was stirred at 70° C. for 18 h. The resulting mixture was cooled to room temperature and then treated with water (200 mL). The resulting solution was acidified to pH 2 with 1N HCl and extracted thrice with ethyl acetate (100 mL). The ethyl acetate extracts were pooled, washed successively with water and brine, then dried over sodium sulfate, filtered and concentrated to yield 3-cyclohexyl-acrylic acid.

$^1$H-NMR (400 MHz, DMSO d$_6$) δ (ppm) 12.1 (s, 1H) 6.73-6.80 (dd, J=6.82, 15.7 Hz, 1H) 5.70-5.72 (dd, J=1.26, 15.7 Hz, 1H) 2.09-2.19 (m, 1H) 1.60-1.75 (m, 5H) 1.05-1.32 (m, 5H).

Step B:
5-Bromo-2-(2-cyclohexyl-vinyl)-1H-benzimidazole

A solution of 3-cyclohexyl-acrylic acid (5.0 g, 32.5 mmol, prepared as in STEP A above) and oxalyl chloride (3.4 mL, 34.0 mmol) in anhydrous methylene chloride (50 mL) was treated with one drop of dimethylformamide. The resulting solution was stirred at room temperature for 18 h, concentrated and used as is for the next step.

To a solution of 4-bromo-benzene-1,2-diamine (3.0 g, 16.1 mmol) in anhydrous toluene (50 mL) was added a solution of 3-cyclohexyl-acryloyl chloride (32.5 mmol) in toluene (5 mL). The resulting solution was stirred at 40° C. for 6 h and then treated with p-toluenesulfonic acid (3.0 g, 16.1 mmol). The resulting mixture was heated at reflux for 18 h. allowed to cool to room temperature and concentrated. The residue obtained was partitioned between ethyl acetate and a saturated solution of sodium bicarbonate in water. The layers were separated. The organic layer was washed successively with saturated. sodium bicarbonate, water and brine, then dried over sodium sulfate, filtered and concentrated. The residue was chromatographed on silica with ethyl acetate/hexanes 3:7 to yield 5-bromo-2-(2-cyclohexyl-vinyl)-1H-benzimidazole.

$^1$H-NMR (400 MHz, DMSO d$_6$) δ (ppm) 12.58 (bs, 1H) 7.4-7.70 (m, 2H) 7.22-7.30 (m, 1H) 6.74-6.84 (m, 1H) 6.34-6.42 (dd, J=1.26, 16.2 Hz, 1H) 2.18-2.24 (m, 1H) 1.60-1.80 (m, 5H) 1.20-1.40 (m, 5H). Mass Spectrum (LCMS, ESI pos.) Calcd. For $C_{15}H_{17}BrN_2$: 305.2, 307.2 (M+H). Found 305.1, 307.2.

Step C: 2-(2-Cyclohexyl-vinyl)-5-(2-trifluoromethoxy-phenyl)-1H-benzimidazole

A solution of 5-bromo-2-(2-cyclohexyl-vinyl)-1H-benzimidazole (1.2 g, 3.9 mmol, prepared as in STEP B above), 2-trifluoromethoxyphenylboronic acid (1.6 g, 7.8 mmol), dichloro[1,1'-bis(diphenylphosphino)ferrocene]palladium (II) dichloromethane adduct (0.752 g, 0.92 mmol) in dimethoxyethane (32 mL) and 2M sodium carbonate (16 mL, 32 mmol) was stirred at 95° C. for 18 h. The resulting solution was cooled to room temperature and poured into a mixture of ethyl acetate and water (1:1, 50 mL). The layers were separated and the organic layer was washed with brine, dried over sodium sulfate, filtered and concentrated. The residue was purified on silica using 3:7 v/v ethyl acetate/hexanes to yield 2-(2-cyclohexyl-vinyl)-5-(2-trifluoromethoxy-phenyl)-1H-benzimidazole.

$^1$H-NMR (400 MHz, DMSO d$_6$) δ (ppm) 7.2-7.64 (m, 7H) 6.76-6.84 (m, 1H) 6.42 (d, J=17.7 Hz, 1H) 2.2 (bs, 1H) 1.6-1.88 (m, 5H) 1.15-1.4 (m, 5H). Mass Spectrum (LCMS, ESI pos.) Calcd. For $C_{22}H_{21}F_3N_2O$: 387.2 (M+H). Found 387.2.

Step D: 2-(2-Cyclohexyl-vinyl)-5-(2-trifluoromethoxy-phenyl)-1H-benzimidazole hydrochloride salt A solution of 2-(2-cyclohexyl-vinyl)-5-(2-trifluoromethoxy-phenyl)-1H-benzimidazole (0.3 g, 0.78 mmol, prepared as in STEP C above) in ethyl ether (5 mL) was treated with 2M HCl in ethyl ether (0.8 mmol, 0.4 mL). After five minutes the resulting solution was concentrated and dried in vacuo to yield the title compound.

$^1$H-NMR (400 MHz, DMSO d$_6$) δ (ppm) 7.8-7.87 (m, 2H) 7.52-7.69 (m, 7H) 7.32-7.40 (dd, J=6.82, 16.4 Hz, 1H) 6.52-6.63 (dd, 1.26, 16.2 Hz, 1H) 2.35-2.47 (m, 1H) 1.65-1.85 (m, 5H) 1.20-1.40 (m, 5H). Mass Spectrum (LCMS, ESI pos.) Calcd. For $C_{22}H_{21}F_3N_2O$: 387.1 (M+H). Found 387.2.

Compounds #2-29 were similarly prepared according to the procedure as described in Example 1 above, with selection and substitution of suitable reagents and starting materials. The Table below lists measured 1HMR and Mass Spec values for the prepared Compounds #2-29.

| ID No. | Compound Name; Measured $^1$HNMR and Mass Spec |
|---|---|
| 2 | 2-(2-Cyclohexyl-vinyl)-5-phenyl-1H-benzimidazole<br>$^1$H-NMR (400 MHz, CD$_3$OD) δ (ppm): 7.73 (s, 1H) 7.58-7.62 (m, 3H) 7.50-7.56 (m, 1H) 7.40-7.48 (m, 2H) 7.30-7.75 (m, 1H) 6.77-6.85 (dd, J = 6.82, 16.4 Hz, 1H) 6.42-6.54 (dd, J = 1.26, 16.4 Hz) 2.2-2.3 (m, 1H) 1.65-1.87 (m, 5H) 1.20-1.42 (m, 5H)<br>Mass Spectrum (LCMS, ESI pos.) Calcd. For $C_{21}H_{22}N_2$: 302.4 (M + H), Found 302.6. |
| 3 | 2-(2-Cyclohexyl-vinyl)-5-o-tolyl-1H-benzimidazole<br>$^1$H-NMR (400 MHz, CD$_3$OD) δ (ppm): 7.44 (d, J = 8.34 Hz, 1H) 7.29 (s, 1H) 7.0-7.18 (m, 6H) 6.6-6.74 (m, 1H) 6.35-6.40 (m, 1H) 2.14-2.18 (m, 4H) 1.58-1.77 (m, 5H) 1.0-1.28 (m, 5H)<br>Mass Spectrum (LCMS, ESI pos.) Calcd. For $C_{22}H_{24}N_2$: 317.2 (M + H), Found 317.2. |
| 4 | 2-(2-Cyclohexyl-vinyl)-5-[2-(2,2,2-trifluoro-ethoxy)-phenyl]-1H-benzimidazole<br>$^1$H-NMR (400 MHz, CD$_3$OD) δ (ppm): 7.63 (s, 1H) 7.52-7.58 (m, 1H) 7.30-7.43 (m, 3H) 7.10-7.18 (m, 2H) 6.78-6.84 (m, 1H) 6.42 (d, J = 16.6 Hz, 1H) 4.40-4.48 (m, 2H) 2.20-2.30 (m, 1H) 1.68-1.90 (m, 5H) 1.20-1.48 (m, 5H)<br>Mass Spectrum (LCMS, ESI pos.) Calcd. For $C_{23}H_{23}F_3N_2O$: 401.2 (M + H), Found 401.2. |
| 5 | 3-[2-(2-Cyclohexyl-vinyl)-1H-benzimidazol-5-yl]-phenol<br>$^1$H-NMR (400 MHz, CD$_3$OD) δ (ppm): 7.58 (s, 1H) 7.34-7.43 (m, 2H) |

| ID No. | Compound Name; Measured ¹HNMR and Mass Spec |
|---|---|
| | 6.88-7.17 (m, 3H) 6.62-6.70 (m, 2H) 6.30-6.38 (dd, J = 1.26, 16.2 Hz, 1H) 2.10-2.21 (m, 1H) 1.59-1.80 (m, 5H) 1.15-1.30 (m, 5H)<br>Mass Spectrum (LCMS, ESI pos.) Calcd. For $C_{21}H_{22}N_2O$: 319.2 (M + H), Found 319.2 |
| 6 | 2-[2-(2-Cyclohexyl-vinyl)-1H-benzimidazol-5-yl]-phenyl}-methanol<br>¹H-NMR (400 MHz, $CD_3OD$) δ (ppm): 7.2-7.62 (m, 7H) 6.77-6.84 (dd, J = 6.82, 16.2 Hz, 1H) 6.44-6.50 (dd, J = 1.52, 16.4 Hz, 1H) 2.22-2.30 (m, 1H) 1.70-1.90 (m, 5H) 1.20-1.46 (m, 5H)<br>Mass Spectrum (LCMS, ESI pos.) Calcd. For $C_{22}H_{24}N_2O$: 333.2 (M + H), Found 333.2 |
| 7 | 2-(2-Cyclohexyl-vinyl)-5-[2-(2-methyl-[1,3]dioxolan-2-yl)-phenyl]-1H-benzimidazole<br>¹H-NMR (400 MHz, $CD_3OD$) δ (ppm): 7.52-7.58 (m, 1H) 7.30-7.80 (m, 2H) 7.16-7.24 (m, 2H) 7.00-7.06 (m, 2H) 6.60-6.70 (m, 1H) 6.30-6.38 (dd, J = 1.26, 16.2 Hz, 1H) 3.58-3.77 (m, 4H) 2.17-2.20 (m, 1H) 1.60-1.80 (m, 5H) 1.08-1.40 (m, 8H)<br>Mass Spectrum (LCMS, ESI pos.) Calcd. For $C_{25}H_{28}N_2O_2$: 389.2 (M + H), Found 389.2. |
| 8 | 1-{2-[2-(2-Cyclohexyl-vinyl)-1H-benzimidazol-5-yl]-phenyl}-ethanone<br>¹H-NMR (400 MHz, $CD_3OD$) δ (ppm): 7.53-7.60 (m, 3H) 7.42-7.50 (m, 3H) 7.18-7.21 (m, 1H) 6.78-6.30 (m, 1H) 6.44-6.49 (dd, J = 1.26, 16.2 Hz, 1H) 2.20-2.30 (m, 1H) 1.95 (s, 3H) 1.70-1.90 (m, 5H) 1.20-1.42 (m, 5H)<br>Mass Spectrum (LCMS, ESI pos.) Calcd. For $C_{23}H_{24}N_2O$: 345.2 (M + H), Found 345.2. |
| 9 | 5-(2-Chloro-5-fluoro-phenyl)-2-(2-cyclohexyl-vinyl)-1H-benzimidazole<br>¹H-NMR (400 MHz, $CDCl_3$) δ (ppm): 7.59-7.62 (m, 2H) 7.36-7.42 (m, 1H) 7.22-7.30 (m, 1H) 6.94-7.10 (m, 2H) 6.76-6.82 (m, 1H) 6.46-6.54 (m, 1H)<br>Mass Spectrum (LCMS, ESI pos.) Calcd. For $C_{21}H_{20}ClFN_2$: 355.1 (M + H), Found 355.2. |
| 10 | 5-(2-Chloro-6-fluoro-phenyl)-2-(2-cyclohexyl-vinyl)-1H-benzimidazole<br>¹H-NMR (400 MHz, $CDCl_3$) δ (ppm): 7.50-7.64 (m, 2H) 7.18-7.34 (m, 4H) 7.08-7.12 (m, 1H) 6.70-6.78 (m, 1H) 6.40-6.50 (m, 1H) 2.20-2.30 (m, 1H) 1.62-1.90 (m, 5H) 1.16-1.41 (m, 5H)<br>Mass Spectrum (LCMS, ESI pos.) Calcd. For $C_{21}H_{20}ClFN_2$: 355.1 (M + H), Found 355.1. |
| 11 | 2-(2-Cyclohexyl-vinyl)-5-(2-fluoro-6-methoxy-phenyl)-1H-benzimidazole<br>¹H-NMR (400 MHz, $CDCl_3$) δ (ppm): 7.56-7.61 (m, 2H) 7.20-7.45 (m, 3H) 6.70-6.82 (m, 3H) 6.44-6.50 (m, 1H) 3.71 (s, 3H) 2.15-2.20 (m, 1H) 1.60-1.80 (m, 5H) 1.05-1.36 (m, 5H).<br>Mass Spectrum (LCMS, ESI pos.) Calcd. For $C_{22}H_{23}FN_2O$: 351.2 (M + H), Found 351.3. |
| 12 | 2-(2-Cyclohexyl-vinyl)-5-(4-fluoro-2-methoxy-phenyl)-1H-benzimidazole<br>¹H-NMR (400 MHz, $CDCl_3$) δ (ppm): 7.50-7.68 (m, 2H) 7.20-7.35 (m, 2H) 6.64-6.80 (m, 3H) 6.42-6.50 (m, 1H) 3.74 (s, 3H) 2.10-2.20 (m, 1H) 1.60-1.80 (m, 5H) 1.04-1.32 (m, 5H)<br>Mass Spectrum (LCMS, ESI pos.) Calcd. For $C_{22}H_{23}FN_2O$: 351.2 (M + H), Found 351.2. |
| 13 | 2-(2-Cyclohexyl-vinyl)-5-(5-fluoro-2-methoxy-phenyl)-1H-benzimidazole<br>¹H-NMR (400 MHz, $CDCl_3$) δ (ppm): 7.54-7.70 (m, 2H) 7.34-7.38 (m, 1H) 6.84-7.10 (m, 3H) 6.70-6.80 (m, 1H) 6.40-6.48 (m, 1H) 3.75 (s, 3H) 2.16-2.21 (m, 1H) 1.60-1.80 (m, 5H) 1.10-1.38 (m, 5H)<br>Mass Spectrum (LCMS, ESI pos.) Calcd. For $C_{21}H_{23}N_3O$: 334.2 (M + H), Found 334.1. |
| 14 | 2-(2-Cyclohexyl-vinyl)-5-(2,6-dimethoxy-phenyl)-1H-benzimidazole<br>¹H-NMR (400 MHz, $CDCl_3$) δ (ppm): 7.48-7.60 (m, 2H) 7.20-7.30 (m, 1H) 7.17-7.20 (m, 1H) 6.60-6.66 (m, 3H) 6.40-6.44 (m, 1H) 3.70 (s, 6H) 2.16-2.20 (m, 1H) 1.64-1.82 (m, 5H) 1.18-1.37 (m, 5H)<br>Mass Spectrum (LCMS, ESI pos.) Calcd. For $C_{23}H_{26}N_2O_2$: 363.2 (M + H), Found 363.2. |
| 15 | 2-(2-Cyclohexyl-vinyl)-5-(2,6-difluoro-phenyl)-1H-benzimidazole<br>¹H-NMR (400 MHz, $CDCl_3$) δ (ppm): 7.52-7.60 (m, 2H) 7.22-7.36 (m, 2H) 6.94-7.00 (m, 2H) 6.63-6.70 (m, 1H) 6.40-6.48 (m, 1H) 2.08-2.20 (m, 1H) 1.60-1.80 (m, 5H) 1.12-1.30 (m, 5H)<br>Mass Spectrum (LCMS, ESI pos.) Calcd. For $C_{21}H_{20}F_2N_2$: 337.2 (M + H), Found 337.2. |
| 16 | 2-(2-Cyclohexyl-vinyl)-5-(2-fluoro-phenyl)-1H-benzimidazole<br>¹H-NMR (400 MHz, $CDCl_3$) δ (ppm): 7.70-7.76 (bs, 1H) 7.56-7.62 (m, 1H) 7.38-7.50 (m, 2H) 7.20-7.30 (m, 1H) 7.10-7.20 (m, 2H) 6.70-6.78 (m, 1H) 6.40-6.48 (m, 1H) 2.16-2.21 (m, 1H) 1.60-1.80 (m, 5H) 1.18-1.30 (m, 5H)<br>Mass Spectrum (LCMS, ESI pos.) Calcd. For $C_{21}H_{21}FN_2$: 321.2 (M + H), Found 321.2. |
| 17 | 2-(2-Cyclohexyl-vinyl)-5-(3-methyl-thiophen-2-yl)-1H-benzimidazole<br>¹H-NMR (400 MHz, $CDCl_3$) δ (ppm): 7.56-7.62 (m, 2H) 7.30-7.36 (m, 1H) 7.15-7.18 (m, 1H) 6.86-6.91 (m, 1H) 6.44-6.52 (m, 1H) 2.28 (s, 3H) 2.11-2.20 (m, 1H) 1.60-1.80 (m, 5H) 1.08-1.20 (m, 5H) |

| ID No. | Compound Name; Measured ¹HNMR and Mass Spec |
|---|---|
| | Mass Spectrum (LCMS, ESI pos.) Calcd. For $C_{20}H_{22}N_2S$: 323.2 (M + H), Found 323.2 |
| 18 | 5-(2-Chloro-5-methoxy-phenyl)-2-(2-cyclohexyl-vinyl)-1H-benzimidazole<br>¹H-NMR (400 MHz, DMSO $d_6$) δ (ppm): 7.70-7.84 (m, 2H) 7.49-7.58 (m, 2H) 7.30-7.37 (m, 1H) 7.00-7.05 (m, 2H) 6.57-6.63 (m, 1H) 3.80 (s, 3H) 2.38-2.44 (m, 1H) 1.60-1.86 (m, 5H) 1.20-1.40 (m, 5.50)<br>Mass Spectrum (LCMS, ESI pos.) Calcd. For $C_{22}H_{23}ClN_2O$: 367.1 (M + H), Found 367.20. |
| 19 | 2-(2-Cyclohexyl-vinyl)-5-(2,5-dichloro-phenyl)-1H-benzimidazole<br>1H-NMR (400 MHz, DMSO $d_6$) δ (ppm): 7.80-7.83 (m, 2H) 7.64-7.70 (m, 1H) 7.54-7.60 (m, 3H) 7.28-7.34 (m, 1H) 6.56-6.63 (m, 1H)<br>Mass Spectrum (LCMS, ESI pos.) Calcd. For $C_{21}H_{20}Cl_2N_2$: 372.3 (M + H), Found 372.4. |
| 20 | 5-(5-Chloro-2-methoxy-phenyl)-2-(2-cyclohexyl-vinyl)-1H-benzimidazole<br>¹H-NMR (400 MHz, DMSO $d_6$) δ (ppm): 7.76-7.82 (m, 2H) 7.58-7.61 (m, 1H) 7.40-7.48 (m, 2H) 7.29-7.36 (m, 1H) 7.16-7.21 (m, 1H) 6.57-6.60 (m, 1H) 3.78 (s, 3H) 3.36-2.44 (m, 1H) 1.60-1.88 (m, 5H) 1.20-1.40 (m, 5H)<br>Mass Spectrum (LCMS, ESI pos.) Calcd. For $C_{22}H_{23}ClN_2O$: 367.1 (M + H), Found 367.2. |
| 21 | 2-(2-Cyclohexyl-vinyl)-5-(2,5-dimethoxy-phenyl)-1H-benzimidazole<br>¹H-NMR (400 MHz, DMSO $d_6$) δ (ppm): 7.74-7.81 (m, 2H) 7.56-7.61 (m, 1H) 7.28-7.34 (m, 1H) 7.08-7.12 (m, 1H) 6.91-7.00 (m, 2H) 6.56-6.63 (m, 1H)<br>Mass Spectrum (LCMS, ESI pos.) Calcd. For $C_{23}H_{26}N_2O_2$: 363.2 (M + H), Found 363.3. |
| 22 | 2-(2-Cyclohexyl-vinyl)-5-(2,5-difluoro-phenyl)-1H-benzimidazole<br>¹H-NMR (400 MHz, DMSO $d_6$) δ (ppm): 7.80-7.90 (m, 2H) 7.64-7.71 (m, 1H) 7.26-7.56 (m, 4H) 6.56-6.62 (m, 1H) 2.36-2.44 (m, 1H) 1.60-1.84 (m, 5H) 1.17-1.40 (m, 5H)<br>Mass Spectrum (LCMS, ESI pos.) Calcd. For $C_{21}H_{20}F_2N_2$: 339.2 (M + H), Found 339.2. |
| 24 | 2-(2-Cyclopentyl-vinyl)-5-(2-fluoro-phenyl)-1H-benzimidazole<br>¹H NMR (400 MHz, DMSO $d_6$) δ (ppm): 8.60 (s, 1H) 8.44-8.56 (m, 2H) 8.24-8.35 (m, 2H) 8.12-8.24 (m, 2H) 7.40-7.45 (m, 1H) 3.64-3.76 (m, 1H) 2.84-2.96 (m, 2H) 2.61-2.77 (m, 4H) 2.40-2.51 (m, 2H)<br>Mass Spectrum (LCMS, ESI pos.) Calcd. For $C_{20}H_{19}FN_2$: 307.2 (M + H), Found 307.2. |
| 25 | 2-(2-Cyclopentyl-vinyl)-5-(3-methyl-thiophen-2-yl)-1H-benzimidazole<br>¹H-NMR (400 MHz, DMSO $d_6$) δ (ppm): 8.45-8.48 (m, 2H) 8.30-8.26 (dd, J = 1.52, 8.34 Hz, 1H) 8.17 (d, J = 5.05 Hz, 1H) 7.86 (d, J = 5.05 Hz, 1H) 7.71-7.78 (dd, J = 8.08, 16.2 Hz, 1H) 7.37-7.43 (dd, J = 1.01, 16.2 Hz, 1H) 3.59-3.67 (m, 1H) 3.23 (s, 3H) 2.80-2.90 (m, 2H) 2.55-2.72 (m, 4H) 2.35-2.45 (m, 2H)<br>Mass Spectrum (LCMS, ESI pos.) Calcd. For $C_{19}H_{20}N_2S$: 309.1 (M + H), Found 309.2. |
| 26 | 2-(2-Cyclopentyl-vinyl)-5-(2-trifluoromethoxy-phenyl)-1H-benzimidazole<br>¹H-NMR (400 MHz, DMSO $d_6$) δ (ppm): 8.24-8.55 (m, 7H) 7.76-7.81 (m, 1H) 7.40-7.43 (m, 1H) 3.64-3.70 (m, 1H) 2.84-2.94 (m, 4H) 2.60-2.76 (m, 4H) 2.40-2.50 (m, 2H)<br>Mass Spectrum (LCMS, ESI pos.) Calcd. For $C_{21}H_{19}F_3N_2O$: 373.1 (M + H), Found 373.2. |
| 27 | 2-[2-(2-Cyclopentyl-vinyl)-1H-benzimidazol-5-yl]-benzonitrile<br>¹H-NMR (400 MHz, DMSO $d_6$) δ (ppm): 8.30-8.80 (m, 7H) 7.76-7.85 (m, 1H) 7.40-7.48 (m, 1H) 3.64-3.76 (m, 1H) 2.84-2.95 (m, 2H) 2.60-2.76 (m, 4H) 2.40-2.50 (m, 2H)<br>Mass Spectrum (LCMS, ESI pos.) Calcd. For $C_{21}H_{19}N_3$: 314.2 (M + H), Found 314.2. |
| 28 | {2-[2-(2-Cyclopentyl-vinyl)-1H-benzimidazol-5-yl]-phenyl}-methanol<br>¹H-NMR (400 MHz, DMSO $d_6$) δ (ppm): 8.40-8.56 (m, 3H) 8.20-8.36 (m, 3H) 8.15-8.18 (m, 1H) 7.72-7.81 (m, 1H) 7.40-7.46 (m, 1H) 5.48 (s, 2H) 3.64-3.72 (m, 1H) 2.84-2.96 (m, 2H) 2.60-2.78 (m, 4H) 2.41-2.50 (m, 2H)<br>Mass Spectrum (LCMS, ESI pos.) Calcd. For $C_{21}H_{22}N_2O$: 319.2 (M + H), Found 319.2. |
| 29 | 1-{2-[2-(2-Cyclopentyl-vinyl)-1H-benzimidazol-5-yl]-phenyl}-ethanone<br>¹H-NMR (400 MHz, DMSO $d_6$) δ (ppm): 8.38-8.56 (m, 6H) 8.12-8.16 (m, 1H) 7.78-7.84 (m, 1H) 7.40-7.44 (m, 1H) 3.64-3.74 (m, 1H) 2.84-2.88 (m, 5H) 2.60-2.78 (m, 4H) 2.40-2.50 (m, 2H)<br>Mass Spectrum (LCMS, ESI pos.) Calcd. For $C_{22}H_{22}N_2O$: 331.2 (M + H), Found 331.2. |

Example 2

2-[2-(4,4-Difluoro-cyclohexyl)-vinyl]-5-(2-trifluoromethyl-phenyl)-1H-benzimidazole hydrochloride salt (Cpd 30)

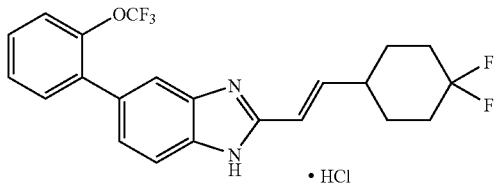

Step A: 1,4-Dioxa-spiro[4.5]decane-8-carboxylic acid ethyl ester

A solution of 4-oxo-cyclohexanecarboxylic acid ethyl ester (5.0 g, 29.4 mmol), ethylene glycol (5.7 mL, 102 mmol) and p-toluenesulfonic acid (0.067 g, 0.35 mmol) in toluene (15 mL) was stirred at room temperature for 18 h. The resulting solution was diluted with ethyl ether (20 mL). The organic layer was washed successively with water and brine, separated and dried with sodium sulfate, filtered and concentrated to yield 1,4-dioxa-spiro[4.5]decane-8-carboxylic acid ethyl ester.

$^1$H-NMR (400 MHz, CDCl$_3$) δ (ppm) 4.02-4.08 (q, J=7.07 Hz, 2H), 3.87 (s, 4H) 2.22-2.30 (m, 1H) 1.84-1.91 (m, 2H) 1.68-1.78 (m, 4H) 1.44-1.53 (m, 2H) 1.16-1.20 (t, J=7.07 Hz, 3H).

Step B: 1,4-Dioxa-spiro[4.5]decane-8-carbaldehyde

A solution of 1,4-dioxa-spiro[4.5]decane-8-carboxylic acid ethyl ester (5.4 g, 25.2 mmol, prepared as in STEP A above) in anhydrous toluene (25 mL) was cooled to −78° C. under an argon atmosphere. To the resulting solution was added a solution of DIBAL-H (26 mL, 1N DIBAL-H in toluene, 26 mmol) in toluene while ensuring the inside temperature was kept between −60 to −70° C. Methanol (25 mL) was added slowly and the resulting mixture was allowed to warm to room temperature, then treated with aqueous sodium chloride (20 mL). The resulting mixture was passed through a silica gel plug (100 g) using ethyl acetate. The resulting eluent was concentrated to yield 1,4-dioxa-spiro[4.5]decane-8-carbaldehyde.

$^1$H-NMR (400 MHz, CDCl$_3$) δ (ppm) 9.58 (m, 1H) 3.82-3.86 (m, 4H) 2.18-2.24 (m, 1H) 1.84-1.90 (m, 2H) 1.60-1.76 (m, 4H) 1.48-1.60 (m, 2H).

Step C: 3-(1,4-Dioxa-spiro[4.5]dec-8-yl)-acrylic acid

A solution of 1,4-dioxa-spiro[4.5]decane-8-carbaldehyde (3.1 g, 18.4 mmol, prepared as in STEP B above), malonic acid (3.8 g, 36.5 mmol), piperidine (0.182 mL, 1.8 mmol) in pyridine (20 mL) was stirred at 70° C. under an argon atmosphere. After 3 h the resulting solution was concentrated. The residue obtained was partitioned between ethyl acetate and water. The layers were separated, and the ethyl acetate layer was washed successively with water and brine. The ethyl acetate layer was dried over sodium sulfate and was filtered, concentrated, and dried in vacuo to yield 3-(1,4-dioxa-spiro[4.5]dec-8-yl)-acrylic acid.

$^1$H-NMR (400 MHz, DMSO d$_6$) δ (ppm) 12.18 (bs, 1H) 6.74-6.80 (dd, J=6.82, 15.7 Hz, 1H) 5.70-5.75 (dd, J=1.52, 15.9 Hz, 1H) 3.85 (m, 4H) 2.15-2.25 (m, 1H) 1.65-1.74 (m, 4H) 1.46-1.55 (m, 2H) 1.30-1.42 (m, 2H).

Step D: N-(2-Amino-4-bromo-phenyl)-3-(1,4-dioxa-spiro[4.5]dec-8-yl)-acrylamide A solution of 3-(1,4-dioxa-spiro[4.5]dec-8-yl)acrylic acid (4.6 g, 21.7 mmol, as prepared in the previous step) and oxalyl chloride (2.3 mL, 26.3 mmol) in methylene chloride (50 mL) was treated with one drop of anhydrous dimethylformamide. The resulting solution was stirred at room temperature for 4 h concentrated and used as is for the next step.

A solution of 3-(1,4-dioxa-spiro[4.5]dec-8-yl)acryloyl chloride (21.7 mmol) in tetrahydrofuran (20 mL) was added slowly to a solution of 4-bromo-benzene-1,2-diamine (5.2 g, 27.9 mmol) and N-methylmorpholine (7.1 mL, 83.7 mmol) in THF (50 mL) at 0° C. The resulting solution was allowed to warm up to room temperature. After 18 h the resulting solution was poured into a solution of ethyl acetate and water (1:1, 80 mL). The layers were separated. The organic layer was washed successively with water and brine dried over sodium sulfate, filtered and concentrated to yield N-(2-amino-4-bromo-phenyl)-3-(1,4-dioxa-spiro[4.5]dec-8-yl)-acrylamide.

Mass Spectrum (LCMS, ESI pos.) Calcd. For C$_{17}$H$_{21}$BrN$_2$O$_3$: 381.1 (M+H). Found 381.2.

Step E: 4-[2-(5-Bromo-1H-benzimidazol-2-yl)-vinyl]-cyclohexanone

A solution of N-(2-amino-4-bromo-phenyl)-3-(1,4-dioxa-spiro[4.5]dec-8-yl)-acrylamide (6.0 g, 28 mmol, prepared as in STEP D above) in 1,4-dioxane (100 mL) was treated with 1N HCl (30 mL, 30 mmol). The resulting solution was stirred at 100° C. for 1 h and then allowed to cool to room temperature. The resulting mixture was made basic with saturated aqueous sodium bicarbonate and extracted thrice with ethyl acetate. The ethyl acetate layers were combined and washed successively with water and brine, separated, dried over sodium sulfate, filtered and concentrated. The residue was taken up in ethyl acetate and applied to a silica gel plug (100 g) equilibrated with ethyl acetate and eluted with ethyl acetate. The desired fractions were pooled, concentrated and dried in vacuo to yield 4-[2-(5-bromo-1H-benzimidazol-2-yl)-vinyl]-cyclohexanone.

$^1$H-NMR (400 MHz, DMSO d$_6$) δ (ppm) 7.64-7.70 (bs, 1H) 7.40-7.48 (m, 1H) 7.24-7.30 (m, 1H) 6.80-6.90 (dd, J=6.82, 16.2 Hz, 1H) 6.47-6.54 (dd, J=1.26, 16.2 Hz, 1H) 2.70-2.82 (m, 1H) 2.45-2.55 (m, 4H) 2.24-2.32 (m, 2H) 2.05-2.13 (m, 2H). Mass Spectrum (LCMS, ESI pos.) Calcd. For C$_{15}$H$_{15}$BrN$_2$O: 321.2 (M+H). Found, 321.2.

Step F: 5-Bromo-2-[2-(4,4-difluoro-cyclohexyl)-vinyl]-1H-benzimidazole

A solution of DAST (0.83 mL, 6.3 mmol) in methylene chloride (10 mL) was cooled in an ice-water bath under an argon atmosphere. To the solution was added dropwise 4-[2-(5-bromo-1H-benzimidazol-2-yl)-vinyl]-cyclohexanone (0.40 g, 1.2 mmol, prepared as in STEP E above). The solution was stirred at 0° C. for 30 minutes and warmed to room temperature. After 18 h the solution was poured into a silica gel plug equilibrated with ethyl acetate/hexanes 1:1 and eluted with ethyl acetate. The desired fractions were pooled, concentrated and dried in vacuo to yield 5-bromo-2-[2-(4,4-difluoro-cyclohexyl)-vinyl]-1H-benzimidazole.

Mass Spectrum (LCMS, ESI pos.) Calcd. For $C_{16}H_{15}BrF_2N_2$: 343.2 (M+H). Found 343.2.

Step G: 2-[2-(4,4-Difluoro-cyclohexyl)-vinyl]-5-(2-fluoro-6-trifluoromethyl-phenyl)-1H-benzimidazole and 2-[2-(4-Fluoro-cyclohex-3-enyl)-vinyl]-5-(2-trifluoromethyl-phenyl)-1H-benzimidazole A solution of 5-bromo-2-[2-(4,4-difluoro-cyclohexyl)-vinyl]-1H-benzimidazole (0.030 g, 0.088 mmol, prepared as in STEP F above), 2-fluoro-6-trifluoromethylphenyl boronic acid (0.040 g, 0.19 mmol), 1,1-bis(di-t-butyl-phosphinoferrocene palladium chloride (0.012 g, 0.018 mmol) in dimethoxyethane (2 mL) and 2M sodium carbonate (1.0 mL, 2 mmol) was stirred at 95° C. for 18 h. The resulting solution was cooled to room temperature and poured into a solution of ethyl acetate and water (1:1, 50 mL). The layers were separated. The organic layer was washed with brine, dried over sodium sulfate, filtered and concentrated. The residue was purified on silica using ethyl acetate/hexanes 3:7 as eluent to yield 2-[2-(4,4-difluoro-cyclohexyl)-vinyl]-5-(2-fluoro-6-trifluoromethyl-phenyl)-1H-benzimidazole.

$^1$H-NMR (400 MHz, DMSO $d_6$) δ (ppm) 7.56-7.64 (m, 2H) 7.44-7.52 (m, 2H) 7.32-7.38 (m, 1H) 7.14-7.18 (m, 1H) 6.68-6.78 (m, 1H) 6.47-6.56 (m, 1H) 2.32-2.40 (m, 1H) 2.10-2.20 (m, 2H) 1.80-1.96 (m, 6H). Mass Spectrum (LCMS, ESI pos.) Calcd. For $C_{22}H_{18}F_6N_2$: 407.1 (M+H). Found 407.3 and 2-[2-(4-fluoro-cyclohex-3-enyl)-vinyl]-5-(2-trifluoromethyl-phenyl)-1H-benzimidazole (0.50 g, 30%). $^1$H-NMR (400 MHz, CDCl$_3$) δ (ppm): 7.70-7.76 (m, 1H) 7.40-7.56 (m, 4H) 7.38-7.40 (m, 1H) 7.16-7.22 (m, 1H) 6.74-6.82 (m, 1H) 6.48-6.56 (m, 1H) 5.14-5.23 (m, 1H) 2.44-2.56 (m, 1H) 2.16-2.30 (m, 3H) 1.90-2.04 (m, 2H). Mass Spectrum (LCMS, ESI pos.) Calcd. For $C_{22}H_{18}F_4N_2$: 387.2 (M+H). Found 387.2.

Compounds #32-49 were similarly prepared according to the procedure as described in Example 2 above, with selection and substitution of suitable reagents and starting materials. The Table below lists measured 1HMR and Mass Spec values for the prepared Compounds #32-49.

| ID No. | Compound Name; Measured $^1$H-NMR and Mass Spec |
|---|---|
| 32 | 2-[2-(4-Fluoro-cyclohex-3-enyl)-vinyl]-5-(2-trifluoromethoxy-phenyl)-1H-benzoimidazole hydrochloride salt<br>$^1$H NMR (400 MHz, DMSO $d_6$) δ (ppm): 7.87-7.90 (d, J = 7.58 Hz, 1H) 7.75-7.82 (m, 2H) 7.65-7.70 (m, 2H) 7.46-7.50 (d, J = 7.32 Hz, 1H) 7.41-7.44 (d, J 8.59 Hz, 1H) 7.29-7.36 (dd, J = 7.07, 16.2 Hz, 1H) 6.65-6.71 (dd, J = 1.26, 16.4 Hz, 1H) 5.25-5.35 (m, 1H) 2.66-2.75 (m, 1H) 2.25-2.35 (m, 3H) 1.90-2.10 (m, 2H)<br>Mass Spectrum (LCMS, ESI pos.). Calcd. For $C_{22}H_{18}F_4N_2O$: 403.1 (M + H), Found 403.2. |
| 33 | 2-[2-(4-Fluoro-cyclohex-3-enyl)-vinyl]-5-(5-fluoro-2-methoxy-phenyl)-1H-benzoimidazole hydrochloride salt<br>$^1$H NMR (400 MHz, DMSO $d_6$) δ (ppm): 7.75-7.83 (m, 2H) 7.59-7.62 (dd, J = 1.52, 8.59 Hz, 1H) 7.15-7.35 (m, 4H) 6.64-6.70 (m, 1H) 5.28-5.34 (m, 1H) 3.76 (s, 3H) 2.65-2.74 (m, 1H) 2.20-2.40 (m, 3H) 1.94-2.10 (m, 2H)<br>Mass Spectrum (LCMS, ESI pos.) Calcd. For $C_{22}H_{20}F_2N_2O$: 367.2 (M + H), Found 367.2. |
| 34 | 5-(2-Chloro-phenyl)-2-[2-(4-fluoro-cyclohex-3-enyl)-vinyl]-1H-benzoimidazole hydrochloride salt<br>$^1$H NMR (400 MHz, DMSO $d_6$) δ (ppm): 7.76-7.84 (m, 2H) 7.42-7.64 (m, 5H) 7.30-7.40 (m, 1H) 6.66-6.72 (m, 1H) 5.26-5.34 (m, 1H) 2.66-2.74 (m, 1H) 2.22-2.40 (m, 3H) 1.94-2.10 (m, 2H)<br>Mass Spectrum (LCMS, ESI pos.) Calcd. For $C_{21}H_{18}FN_2$: 353.1 (M + H), Found 353.2. |
| 35 | 5-(2,6-Dimethyl-phenyl)-2-[2-(4-fluoro-cyclohex-3-enyl)-vinyl]-1H-benzoimidazole hydrochloride salt<br>$^1$H NMR (400 MHz, DMSO $d_6$) δ (ppm): 7.80-7.84 (d, J = 8.33 Hz, 1H) 7.57 (bs, 1H) 7.03-7.35 (m, 5H) 6.88-6.92 (d, J = 7.58 Hz, 1H) 6.65-6.70 (m, 1H) 5.26-5.34 (m, 1H) 2.66-2.75 (m, 1H) 2.24-2.36 (m, 5H) 2.00-2.10 (m, 7H) 1.64-1.76 (m, 1H)<br>Mass Spectrum (LCMS, ESI pos.) Calcd. For $C_{23}H_{23}FN_2$: 347.2 (M + H), Found 347.2. |
| 36 | 2-[2-(4-Fluoro-cyclohex-3-enyl)-vinyl]-5-(2-fluoro-phenyl)-1H-benzoimidazole hydrochloride salt<br>$^1$H NMR (400 MHz, DMSO $d_6$) δ (ppm): 7.76-7.80 (bs, 1H) 7.58-7.63 (m, 1H) 7.40-7.50 (m, 2H) 7.28-7.34 (m, 1H) 7.15-7.20 (m, 2H) 6.76-6.82 (m, 1H) 6.50-6.58 (d, J = 16.17 Hz, 1H) 5.10-5.20 (m, 1H) 2.44-2.52 (m, 1H) 2.18-2.34 (m, 3H) 1.90-2.04 (m, 3H)<br>Mass Spectrum (LCMS, ESI pos.) Calcd. For $C_{21}H_{18}F_2N_2$: 337.4 (M + H), Found 337.4. |
| 37 | 2-[2-(4,4-Difluoro-cyclohexyl)-vinyl]-5-(2-trifluoromethoxy-phenyl)-1H-benzoimidazole hydrochloride salt<br>$^1$H NMR (400 MHz, DMSO $d_6$) δ (ppm): 7.80-7.88 (m, 2H) 7.50-7.64 (m, 5H) 7.26-7.35 (dd, J = 7.32, 16.42 Hz, 1H) 6.62-6.68 (d, J = 16.42 Hz, 1H) 2.55-2.65 (m, 1H) 1.88-2.15 (m, 6H)<br>Mass Spectrum (LCMS, ESI pos.) Calcd. For $C_{22}H_{19}F_5N_2O$: 423.1 (M + H), Found 423.2 |
| 38 | 5-(2-Chloro-phenyl)-2-[2-(4,4-difluoro-cyclohexyl)-vinyl]-1H-benzoimidazole hydrochloride salt<br>$^1$H NMR (400 MHz, DMSO $d_6$) δ (ppm): 7.81-7.84 (d, J = 8.59 Hz, 1H) 7.77 (s, 1H) 7.45-7.55 (m, 4H) 7.24-7.31 (dd, J = 6.82, 16.42, 1H) |

| ID No. | Compound Name; Measured $^1$H-NMR and Mass Spec |
|---|---|
| | 6.62-6.67 (d, J = 16.17 Hz, 1H) 2.55-2.65 (m, 1H) 1.88-2.15 (m, 6H)<br>Mass Spectrum (LCMS, ESI pos.) Calcd. For $C_{21}H_{19}F_2N_2Cl$:<br>373.1 (M + H), Found 373.2. |
| 39 | 2-[2-(4,4-Difluoro-cyclohexyl)-vinyl]-5-(2-fluoro-phenyl)-1H-benzoimidazole hydrochloride salt<br>$^1$H NMR (400 MHz, DMSO $d_6$) δ (ppm): 7.82-7.89 (m, 2H)<br>7.56-7.70 (m, 2H) 7.44-7.52 (m, 1H) 7.25-7.40 (m, 3H) 6.62-6.68 (d, J = 16.17 Hz, 1H) 2.56-2.68 (m, 1H) 1.88-2.17 (m, 6H)<br>Mass Spectrum (LCMS, ESI pos.) Calcd. For $C_{21}H_{19}F_3N_2$: 357.2 (M + H), Found 357.2. |
| 40 | 5-(2,6-Dimethoxy-phenyl)-2-[2-(4-fluoro-cyclohex-3-enyl)-vinyl]-1H-benzoimidazole hydrochloride salt<br>$^1$H NMR (400 MHz, DMSO $d_6$) δ (ppm): 7.70-7.76 (d, J = 8.59 Hz, 1H)<br>7.55 (s, 1H) 7.26-7.38 (m, 3H) 6.77-6.81 (d, J = 8.59 Hz, 2H)<br>6.65-6.70 (d, J = 15.91 Hz, 1H) 5.26-5.36 (m, 1H) 3.66 (s, 6H)<br>2.68-2.76 (m, 1H) 2.26-2.36 (m, 3H) 1.90-2.15 (m, 3H). Mass Spectrum (LCMS, ESI pos.) Calcd. For $C_{23}H_{23}FN_2O_2$: 379.1 (M + H), Found 379.2. |
| 41 | 2-[2-(4-Fluoro-cyclohex-3-enyl)-vinyl]-5-(2-fluoro-6-methoxy-phenyl)-1H-benzoimidazole hydrochloride salt<br>$^1$H NMR (400 MHz, $CD_3OD$) δ (ppm): 8.70-8.76 (d, J = 8.59 Hz, 1H)<br>8.64 (s, 1H) 8.50-8.56 (d, J = 11.12 Hz, 1H) 8.30-8.40 (m, 1H)<br>8.16-8.24 (m, 1H) 7.90-7.96 (d, J = 8.58 Hz) 7.76-7.82 (m, 1H)<br>7.61-7.70 (d, J = 16.42 Hz, 1H) 6.19-6.22 (m, 1H) 4.72 (s, 3H) 3.64-3.73 (m, 1H)<br>3.00-3.40 (m, 5H) 2.72-2.82 (m, 1H)<br>Mass Spectrum (LCMS, ESI pos.) Calcd. For $C_{22}H_{20}F_2N_2O$:<br>367.2 (M + H), Found 367.2. |
| 42 | 2-[2-(4,4-Difluoro-cyclohexyl)-vinyl]-5-(2-fluoro-6-trifluoromethyl-phenyl)-1H-benzoimidazole hydrochloride salt<br>$^1$H NMR (400 MHz, $CD_3OD$) δ (ppm): 8.76-8.80 (d, J = 8.59 Hz, 1H)<br>8.60-8.66 (m, 3H) 8.46-8.54 (m, 2H) 8.10-8.20 (dd, J = 6.82, 16.17, 1H) 7.62-7.66 (d, J = 16.42 Hz, 1H) 3.50-3.64 (m, 1H) 3.05-3.16 (m, 3H) 2.80-3.00 (m, 5H)<br>Mass Spectrum (LCMS, ESI pos.) Calcd. For $C_{22}H_{18}F_6N_2$: 425.1 (M + H), Found 425.2. |
| 43 | 2-[2-(4,4-Difluoro-cyclohexyl)-vinyl]-5-(2,6-dimethoxy-phenyl)-1H-benzoimidazole hydrochloride salt<br>$^1$H NMR (400 MHz, DMSO $d_6$) δ (ppm): 7.73-7.76 (d, J = 8.59 Hz, 1H)<br>7.55 (s, 1H) 7.28-7.38 (m, 3H) 6.76-6.81 (d, J = 8.59 Hz, 2H)<br>6.64-6.68 (d, J = 16.42 Hz, 1H) 3.66 (s, 3H) 2.55-2.66 (m, 1H)<br>1.88-2.16 (m, 7H)<br>Mass Spectrum (LCMS, ESI pos.) Calcd. For $C_{23}H_{24}F_2N_2O_2$:<br>399.2 (M + H), Found 399.2. |
| 44 | 2-[2-(4,4-Difluoro-cyclohexyl)-vinyl]-5-(2-fluoro-6-methoxy-phenyl)-1H-benzoimidazole hydrochloride salt<br>$^1$H NMR (400 MHz, DMSO $d_6$) δ (ppm): 7.76-7.80 (d, J = 8.59 Hz, 1H)<br>7.70 (s, 1H) 7.40-7.48 (m, 2H) 7.22-7.34 (m, 1H) 6.94-7.20 (m, 2H)<br>6.60-6.66 (d, J = 16.42 Hz, 1H) 3.76 (s, 3H) 2.56-2.66 (m, 1H)<br>1.86-2.18 (m, 6H) 1.44-1.56 (m, 2H)<br>Mass Spectrum (LCMS, ESI pos.) Calcd. For $C_{22}H_{21}F_3N_2O$:<br>387.2 (M + H), Found 387.2. |
| 45 | 2-[2-(4,4-Difluoro-cyclohexyl)-vinyl]-5-(5-fluoro-2-methoxy-phenyl)-1H-benzoimidazole hydrochloride salt<br>$^1$H NMR (400 MHz, DMSO $d_6$) δ (ppm): 7.81 (s, 1H) 7.75-7.80 (d, J = 8.59 Hz, 1H) 7.57-7.61 (d, J = 8.33 Hz, 1H) 7.16-7.30 (m, 4H)<br>6.60-6.66 (d, J = 16.17 Hz, 1H) 3.76 (s, 3H) 2.56-2.64 (m, 1H)<br>1.90-2.17 (m, 6H) 1.42-1.56 (m, 2H)<br>Mass Spectrum (LCMS, ESI pos.) Calcd. For $C_{22}H_{21}F_3N_2O$:<br>387.2 (M + H), Found 387.2. |
| 46 | 2-[2-(4-Fluoro-cyclohex-3-enyl)-vinyl]-7-trifluoromethyl-5-(2-trifluoromethyl-phenyl)-1H-benzoimidazole hydrochloride salt<br>$^1$H NMR (400 MHz, DMSO $d_6$) δ (ppm): 7.84-7.88 (d, J = 7.33 Hz, 1H)<br>7.72-7.78 (m, 2H) 7.62-7.68 (m, 1H) 7.48-7.52 (d, J = 7.33 Hz, 1H)<br>7.42 (s, 1H) 7.00-7.08 (dd, J = 7.07, 16.17 Hz, 1H) 6.57-6.68 (d, J = 16.42 Hz, 1H) 5.24-5.32 (m, 1H) 2.50-2.64 (m, 1H) 2.18-2.38 (m, 3H) 1.90-2.10 (3H)<br>Mass Spectrum (LCMS, ESI pos.) Calcd. For $C_{23}H_{17}F_7N_2$: 455.1 (M + H), Found 455.2. |
| 47 | 2-[2-(4,4-Difluoro-cyclohexyl)-vinyl]-7-trifluoromethyl-5-(2-trifluoromethyl-phenyl)-1H-benzoimidazole hydrochloride salt<br>$^1$H NMR (400 MHz, DMSO $d_6$) δ (ppm): 7.84-7.90 (d, J = 7.07H, 1H)<br>7.48-7.78 (m, 4H) 7.40 (s, 1H) 6.94-7.00 (dd, J = 6.82, 16.42 Hz, 1H)<br>6.56-6.60 (d, J = 16.42 Hz, 1H) 1.80-2.16 (m, 6H) 1.42-1.56 (m, 2H)<br>Mass Spectrum (LCMS, ESI pos.) Calcd. For $C_{23}H_{18}F_8N_2$: 475.1 (M + H), Found 475.2. |
| 48 | 2-(2-Cyclohexyl-vinyl)-7-methyl-5-(2-trifluoromethoxy-phenyl)-1H-benzoimidazole hydrochloride salt<br>$^1$H NMR (400 MHz, DMSO $d_6$) δ (ppm): 7.50-7.61 (m, 5H) 7.39 (s, |

| ID No. | Compound Name; Measured ¹H-NMR and Mass Spec |
|---|---|
| | 1H) 7.22-7.31 (dd, J = 7.07, 16.42 Hz, 1H) 6.52-6.58 (d, J = 17.68 Hz, 1H) 2.61 (s, 3H) 2.36-2.42 (m, 1H) 1.6-1.90 (m, 6H) 1.30-1.40 (2H) Mass Spectrum (LCMS, ESI pos.) Calcd. For $C_{23}H_{23}F_3N_2O$: 401.2 (M + H), Found 401.2. |
| 49 | 2-(2-Cyclohexyl-vinyl)-7-methyl-5-(2-trifluoromethyl-phenyl)-1H-benzoimidazole hydrochloride salt<br>¹H NMR (400 MHz, DMSO $d_6$) δ (ppm): 7.84-7.86 (d, J = 8.08 Hz, 1H) 7.72-7.76 (m, 1H) 7.62-7.68 (m, 1H) 7.43-7.47 (m, 2H) 7.21-7.29 (m, 2H) 6.54-6.58 (dd, J = 1.26, 16.42 Hz) 2.60 (s, 3H) 2.36-2.42 (m, 1H) 1.60-1.84 (m, 5H) 1.20-1.40 (m, 5H) Mass Spectrum (LCMS, ESI pos.) Calcd. For $C_{23}H_{23}F_3N_2$: 385.2 (M + H), Found 385.2. |

Example 3

(E)-2-[2-(Tetrahydro-pyran-4-yl)-vinyl]-5-(2-trifluoromethyl-phenyl)-1H-benzimidazole hydrochloride (Cpd 50)

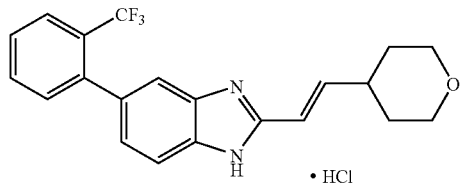

Step A: 3-Nitro-2'-trifluoromethyl-biphenyl-4-ylamine

A solution of 4-bromo-2-nitro-phenylamine (5.00 g, 0.0230 mol) in DME (100 mL) was treated with (2-trifluoromethylphenyl) boronic acid (5.25 g, 0.0277 mol), LiCl (0.976 g, 0.0230 mol), and 2M aqueous $Na_2CO_3$ (92.1 mL, 0.184 mol). The resulting mixture was heated to 80° C. under a stream of Argon, treated with Pd(PPh₃)₄ (2.66 g, 0.00230 mol) and heated to 80° C. overnight. The cooled mixture was diluted with water and extracted thrice with EtOAc. The combined organic layers were dried over $MgSO_4$ and concentrated in vacuo. The residue was purified on a 200-g Sepra Si 50 SPE column (Isco system: flow rate=40 mL/min; eluting with EtOAc/hexanes, 5:95 v/v, over 10 min, 5:95 to 20:80, v/v over 25 min, and 20:80 to 40:60 v/v over 35 min) to yield 3-nitro-2'-trifluoromethyl-biphenyl-4-ylamine as an orange solid ¹H-NMR (400 MHz; CDCl₃) δ: 8.11 (d, J=2.0 Hz, 1H), 7.75 (d, J=7.8 Hz, 1H), 7.58 (t, J=7.2 Hz, 1H), 7.49 (t, J=7.5 Hz, 1H), 7.31-7.39 (m, 2H), 6.85 (d, J=8.6 Hz, 1H), 6.16 (br. s., 2H). Mass Spectrum (LCMS, ESI pos.) Calcd. For $C_{13}H_9F_3N_2O_2$: 283.1 (M+H). Found 283.2.

Step B: (E)-N-(3-Nitro-2'-trifluoromethyl-biphenyl-4-yl)-3-(tetrahydro-pyran-4-yl)-acrylamide A solution of (E)-3-(tetrahydro-pyran-4-yl)-acrylic acid (prepared as described in PCT Publication WO 2005/101989 (A2,A3), 0.200 g, 1.28 mmol) in dry $CH_2Cl_2$ (5 mL) was treated with oxalyl chloride (0.110 mL, 0.00128 mol) and DMF (1 drop) at room temperature for 1 h. The volatiles were evaporated in vacuo (water bath temperature <30° C.). At the same time, a suspension of NaH (78.8 mg, 1.97 mmol, 60% dispersion in oil) in dry THF (3 mL) was treated portionwise with 3-nitro-2'-trifluoromethyl-biphenyl-4-ylamine (278 mg, 0.985 mmol, prepared as in STEP A above) and stirred at room temperature for 30 min. The residue was taken up in dry THF (2 mL) and slowly added to the NaH mixture. The resulting mixture was stirred at room temperature overnight, quenched with saturated aqueous NH₄Cl (20 mL) and extracted with EtOAc (2×20 mL). The combined organic layers were dried over $MgSO_4$ and concentrated in vacuo. The residue was purified on a 24-g Sepra Si 50 SPE column (Isco system: flow rate=20 mL/min; eluting with EtOAc/hexane, 5:95, v/v over 5 min and 5:95 to 40:60, v/v over 25 min) to yield (E)-N-(3-nitro-2'-trifluoromethyl-biphenyl-4-yl)-3-(tetrahydro-pyran-4-yl)-acrylamide as a yellow solid.

¹H-NMR (400 MHz; CDCl₃) δ: 10.55 (s, 1H), 8.95 (d, J=8.8 Hz, 1H), 8.23 (d, J=2.0 Hz, 1H), 7.79 (d, J=7.8 Hz, 1H), 7.58-7.68 (m, 2H), 7.51-7.58 (m, 1H), 7.34 (d, J=7.6 Hz, 1H), 7.02 (dd, J=15.4, 6.6 Hz, 1H), 6.03 (dd, J=15.4, 1.5 Hz, 1H), 4.00-4.08 (m, 2H), 3.43-3.53 (m, 2H), 2.44-2.57 (m, 1H), 1.70-1.79 (m, 2H), 1.54-1.67 (m, 2H). Mass Spectrum (LCMS, ESI pos.) Calcd. For $C_{21}H_{19}F_3N_2O_4$: 421.1 (M+H). Found 420.9.

Step C: (E)-N-(3-Amino-2'-trifluoromethyl-biphenyl-4-yl)-3-(tetrahydro-pyran-4-yl)-acrylamide A solution of (E)-N-(3-nitro-2'-trifluoromethyl-biphenyl-4-yl)-3-(tetrahydro-pyran-4-yl)-acrylamide (82.0 mg, 0.195 mmol) in MeOH (5 mL) and water (5 mL) was treated with NH₄Cl (104 mg, 1.95 mmol) and Fe powder (54.5 mg, 0.975 mmol) and heated to 50° C. for 1 h. The cooled mixture was treated with saturated aqueous NaHCO₃ (30 mL) and extracted with EtOAc (2×30 mL). The combined organic layers were dried over $MgSO_4$ and concentrated in vacuo to yield (E)-N-(3-amino-2'-trifluoromethyl-biphenyl-4-yl)-3-(tetrahydro-pyran-4-yl)-acrylamide as a colorless glassy solid.

Mass Spectrum (LCMS, APCI pos.) Calcd. For $C_{21}H_{21}F_3N_2O_2$: 391.2 (M+H). Found 391.1.

Step D: (E)-2-[2-(Tetrahydro-pyran-4-yl)-vinyl]-5-(2-trifluoromethyl-phenyl)-1H-benzimidazole A mixture of N-(3-amino-2'-trifluoromethyl-biphenyl-4-yl)-3-(tetrahydro-pyran-4-yl)-acrylamide (76.0 mg, 0.195 mmol, as prepared in the previous step) in toluene (5 mL) was treated with p-toluenesulfonic acid (74.2 mg, 0.390 mmol) and heated to 100° C. under a reflux condenser for 4 h. The cooled mixture was treated with saturated aqueous NaHCO₃ (50 mL) and extracted with EtOAc (2×50 mL). The combined organic layers were dried over $MgSO_4$ and concentrated in vacuo. The residue was purified on a 24-g Sepra Si 50 SPE column (Isco system: flow rate=20 mL/min; Eluent=1% MeOH—$CH_2Cl_2$ for 0-5 min, then 1-4% MeOH—$CH_2Cl_2$ for 5-25 min). The resulting residue was purified by RP-HPLC (C18) eluting with $CH_3CN$, 0.1% TFA/water, 10:90 to 50:50, v/v over a period of 20 minutes. The desired column fractions were treated with saturated aqueous NaHCO₃ to pH 7 and extracted with EtOAc. The organic layer was dried over MgSO$_4$ and concentrated in vacuo to yield (E)-2-[2-(tetrahydro-pyran-4-yl)-vinyl]-5-(2-trifluoromethyl-phenyl)-1H-benzimidazole as a pale yellow solid.

$^1$H-NMR (400 MHz; CDCl$_3$) δ: 7.72-7.76 (m, 1H), 7.44-7.61 (m, 4H), 7.38 (d, J=7.6 Hz, 1H), 7.21 (dd, J=8.2, 1.1 Hz, 1H), 6.75 (dd, J=16.2, 6.8 Hz, 1H), 6.51 (dd, J=16.2, 1.5 Hz, 1H), 3.97-4.05 (m, 2H), 3.47 (td, J=11.7, 2.0 Hz, 2H), 2.42-2.55 (m., 1H), 1.68-1.77 (m, 2H), 1.50-1.65 (m, 2H). Mass Spectrum (LCMS, APCI pos.) Calcd. For C$_{21}$H$_{19}$F$_3$N$_2$O: 373.1 (M+H). Found 373.3.

Step E: (E)-2-[2-(Tetrahydro-pyran-4-yl)-vinyl]-5-(2-trifluoromethyl-phenyl)-1H-benzimidazole hydrochloride A mixture of (E)-2-[2-(tetrahydro-pyran-4-yl)-vinyl]-5-(2-trifluoromethyl-phenyl)-1H-benzimidazole (0.220 g, 0.591 mmol, prepared as in STEP D above) in EtOH (4 mL) was treated with 5M HCl in i-PrOH (130 μL, 0.650 mmol) at room temperature for 1 h and concentrated in vacuo. The residue was taken up in a minimum amount of EtOH (2 mL). Hexane was added with stirring until the mixture became cloudy. EtOH (1 mL) was added, and hexane was very slowly added until precipitate formed. The resulting mixture was cooled in the refrigerator for 45 min. The solid was filtered, washed with cold hexane, and air-dried to yield (E)-2-[2-(tetrahydro-pyran-4-yl)-vinyl]-5-(2-trifluoromethyl-phenyl)-1H-benzimidazole hydrochloride as an off-white solid.

$^1$H-NMR (400 MHz; CD$_3$OD) δ: 7.87 (d, J=7.8 Hz, 1H), 7.81 (d, J=8.3 Hz, 1H), 7.70-7.77 (m, 1H), 7.61-7.70 (m, 2H), 7.55 (d, J=8.6 Hz, 1H), 7.47 (d, J=7.6 Hz, 1H), 7.21 (dd, J=16.3, 6.7 Hz, 1H), 6.68 (d, J=16.2 Hz, 1H), 4.01-4.09 (m, 2H), 3.57 (td, J=11.7, 2.3 Hz, 2H), 2.68-2.82 (m, 1H), 1.82-1.90 (m, 2H), 1.58-1.73 (m, 2H). Mass Spectrum (LCMS, APCI pos.) Calcd. For C$_{21}$H$_{19}$F$_3$N$_2$O: 373.1 (M+H). Found 373.2.

Example 4

(E)-2-[2-(Tetrahydro-thiopyran-4-yl)-vinyl]-5-(2-trifluoromethyl-phenyl)-1H-benzimidazole (Cpd 51)

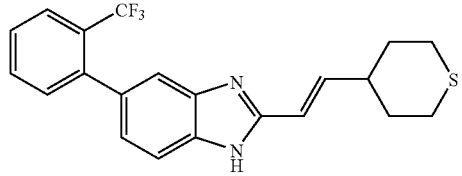

Step A: (E)-N-(3-Nitro-2'-trifluoromethyl-biphenyl-4-yl)-3-(tetrahydro-thiopyran-4-yl)-acrylamide Following the procedure as described in Example 3, STEP B the title compound was prepared as a bright yellow solid, from 3-nitro-2'-trifluoromethyl-biphenyl-4-ylamine (1.51 g, 0.00536 mol) and (E)-3-(tetrahydro-thiopyran-4-yl)-acrylic acid (prepared from tetrahydro-thiopyran-4-carbaldehyde 1.32 g, 0.00766 mol, according to the procedure as described in PCT Publication WO 2005/101989 (A2,A3)).

$^1$H-NMR (400 MHz; CDCl$_3$) δ: 8.12 (d, J=2.0 Hz, 1H), 7.82 (d, J=7.1 Hz, 1H), 7.64-7.72 (m, 2H), 7.60 (t, J=8.0 Hz, 1H), 7.44 (d, J=7.6 Hz, 1H), 7.33 (d, J=8.1 Hz, 1H), 6.99 (dd, J=15.4, 6.6 Hz, 1H), 6.23 (d, J=15.9 Hz, 1H), 2.56-2.76 (m, 4H), 2.13-2.27 (m, 1H), 1.97-2.05 (m, 2H), 1.45-1.66 (m, 2H).

Step B: (E)-N-(3-Amino-2'-trifluoromethyl-biphenyl-4-yl)-3-(tetrahydro-thiopyran-4-yl)-acrylamide Following the procedure as described in Example 3, STEP C, the title compound was prepared from (E)-N-(3-nitro-2'-trifluoromethyl-biphenyl-4-yl)-3-(tetrahydro-thiopyran-4-yl)-acrylamide (0.969 g, 2.22 mmol, prepared in STEP A above) and was obtained as an off-white solid.

1H-NMR (400 MHz; CDCl$_3$) δ: 7.72 (d, J=7.8 Hz, 1H), 7.50-7.58 (m, 1H), 7.41-7.49 (m, 1H), 7.28-7.36 (m, 2H), 7.15 (brs, 1H), 6.87-7.01 (m, 1H), 6.78 (brs, 2H), 5.96 (d, J=15.7 Hz, 1H), 3.91 (br. s., 2H), 2.58-2.82 (m, 4H), 2.19-2.32 (m., 1H), 2.13 (d, J=13.1 Hz, 2H), 1.56-1.71 (m, 2H). Mass Spectrum (LCMS, ESI pos.) Calcd. For C$_{21}$H$_{21}$F$_3$N$_2$OS: 407.1 (M+H). Found 407.1.

Step C: (E)-2-[2-(Tetrahydro-thiopyran-4-yl)-vinyl]-5-(2-trifluoromethyl-phenyl)-1H-benzimidazole A solution of (E)-N-(3-amino-2'-trifluoromethyl-biphenyl-4-yl)-3-(tetrahydro-thiopyran-4-yl)-acrylamide (143 mg, 0.351 mmol, prepared as in STEP B above) in EtOH (20 mL) and glacial acetic acid (4 mL) was heated to 60° C. overnight. The cooled mixture was treated with saturated aqueous NaHCO$_3$ to pH 7, and EtOH was removed in vacuo. The remaining aqueous mixture was extracted twice with CH$_2$Cl$_2$. The combined organic layers were dried over MgSO$_4$ and concentrated in vacuo. The resulting residue was purified by RP-HPLC (C18), eluting with CH$_3$CN/0.1% TFA/water, 10:90 to 80:20, v/v over 25 min. The desired column fractions were treated with saturated aqueous NaHCO$_3$ to pH 7 and extracted with CH$_2$Cl$_2$ (3×). The organic layers were dried over MgSO$_4$ and concentrated in vacuo to yield (E)-N-(3-amino-2'-trifluoromethyl-biphenyl-4-yl)-3-(tetrahydro-thiopyran-4-yl)-acrylamide as a pale yellow solid.

$^1$H-NMR (400 MHz; CDCl$_3$) δ: 7.75 (d, J=7.8 Hz, 1H), 7.56 (t, J=7.5 Hz, 1H), 7.47 (t, J=7.6 Hz, 1H), 7.38 (d, J=7.6 Hz, 1H), 7.20 (d, J=8.1 Hz, 1H), 6.70 (dd, J=16.3, 6.9 Hz, 1H), 6.48 (d, J=16.2 Hz, 1H), 2.62-2.82 (m, 4H), 2.23-2.37 (m, 1H), 2.09-2.17 (m, 2H), 1.55-1.71 (m, 2H). Mass Spectrum (LCMS, APCI pos.) Calcd. For C$_{21}$H$_{19}$F$_3$N$_2$S: 389.1 (M+H). Found 389.2.

Example 5

(E)-5-(2-Fluoro-phenyl)-2-[2-(tetrahydro-pyran-4-yl)-vinyl]-1H-benzimidazole trifluoroacetic acid salt (Cpd 52)

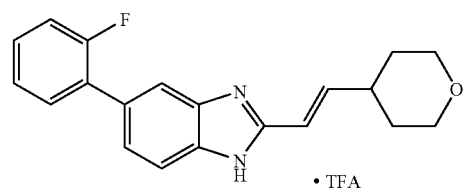

Step A: (E)-N-(4-Bromo-2-nitro-phenyl)-3-(tetrahydro-pyran-4-yl)-acrylamide

Following the procedure as described in Example 3, STEP B, the title compound was prepared from 4-bromo-2-nitro-phenylamine (2.06 g, 9.47 mmol) and (E)-3-(tetrahydro-pyran-4-yl)-acrylic acid (prepared as described in PCT Publication WO 2005/101989 (A2,A3), 1.14 g, 7.29 mmol) and was obtained as a yellow solid.

$^1$H-NMR (400 MHz; CDCl$_3$) δ: 10.40 (s, 1H), 8.84 (d, J=9.1 Hz, 1H), 8.38 (d, J=2.3 Hz, 1H), 7.75 (dd, J=9.1, 2.3 Hz, 1H), 7.00 (dd, J=15.4, 6.6 Hz, 1H), 5.98 (dd, J=15.4, 1.5 Hz, 1H), 4.03 (dt, J=9.4, 2.2 Hz, 2H), 3.47 (td, J=11.7, 2.1 Hz, 2H), 2.42-2.55 (m, 1H), 1.68-1.77 (m, 2H), 1.51-1.65 (m, 2H).

Step B: (E)-5-Bromo-2-[2-(tetrahydro-pyran-4-yl)-vinyl]-1H-benzimidazole

A solution of (E)-N-(4-bromo-2-nitro-phenyl)-3-(tetrahydro-pyran-4-yl)-acrylamide (1.26 g, 3.55 mmol, as prepared in the previous step) in 25 mL anhydrous MeOH was treated with glacial acetic acid (4 mL) and Fe powder (0.991 g, 0.0177 mol) and heated to 85° C. under a reflux condenser for 2 h. The resulting mixture was concentrated in vacuo, treated with saturated aqueous NaHCO$_3$ (200 mL) and extracted thrice with 125 mL CH$_2$Cl$_2$. The combined organic layers were dried over MgSO$_4$ and concentrated in vacuo. The residue was triturated with CH$_2$Cl$_2$, and the resulting solid was filtered and air-dried. The mother liquor was purified on an 80-g Sepra Si 50 SPE column (Isco system: flow rate=30 mL/min; eluting with EtOAc/hexane, 40:60 v/v over 10 min and 40:60 to 100:0, v/v over 30 min to yield (E)-5-bromo-2-[2-(tetrahydro-pyran-4-yl)-vinyl]-1H-benzimidazole as a white solid.

$^1$H-NMR (400 MHz; CDCl$_3$) δ: 7.01-7.14 (m, 2H), 6.84-7.01 (m, 3H), 5.93 (d, J=15.4 Hz, 1H), 4.01 (d, J=9.3 Hz, 2H), 3.94 (br. s., 2H), 3.46 (t, J=11.5 Hz, 2H), 2.37-2.49 (m, 1H), 1.65-1.76 (m, 2H). Mass Spectrum (LCMS, APCI pos.) Calcd. For C$_{14}$H$_{15}$BrN$_2$O: 307.0 (M+H). Found 307.1.

Step C: (E)-5-(2-Fluoro-phenyl)-2-[2-(tetrahydropyran-4-yl)-vinyl]-1H-benzimidazole trifluoroacetic acid salt A solution of (E)-5-bromo-2-[2-(tetrahydro-pyran-4-yl)-vinyl]-1H-benzimidazole (0.100 g, 0.326 mmol, prepared as in STEP B above) in DME (10 mL) was treated with 2-fluorophenyl boronic acid (54.7 mg, 0.391 mmol), LiCl (13.8 mg, 0.326 mmol), and Na$_2$CO$_3$ (1.30 mL, 0.00260 mol, 2M aqueous). The resulting mixture was degassed via sonication, placed under Ar, treated with tetrakis(triphenylphosphine) palladium (37.6 mg, 0.0326 mmol), and heated to 80° C. overnight. The cooled mixture was diluted with water (50 mL) and extracted twice with 50 mL EtOAc. The residue was purified on a 40-g Sepra Si 50 SPE column (Isco system: flow rate=30 mL/min; eluting with EtOAc/hexane, 30:70, v/v over 10 min and 30:70 to 100:0, v/v over 30 min). The resulting material was purified again by RP-HPLC (C18), eluting with CH$_3$CN/0.1% TFA in water 10:90 to 80:20 over 25 min to yield (E)-5-(2-fluoro-phenyl)-2-[2-(tetrahydro-pyran-4-yl)-vinyl]-1H-benzimidazole trifluoroacetic acid salt as a white solid.

$^1$H-NMR (400 MHz; CD$_3$OD) δ: 7.36-7.58 (m, 5H), 7.18-7.35 (m, 2H), 7.04 (dd, J=15.5, 6.4 Hz, 1H), 6.24 (d, J=15.4 Hz, 1H), 4.01 (dd, J=11.5, 2.7 Hz, 2H), 3.46-3.60 (m, 2H), 2.47-2.61 (m, 1H), 1.77 (d, J=12.9 Hz, 2H), 1.48-1.64 (m, 2H). Mass Spectrum (LCMS, APCI pos.) Calcd. For C$_{20}$H$_{19}$FN$_2$O: 323.2 (M+H). Found 323.2.

Example 6

(E)-7-Methyl-2-[2-(tetrahydro-pyran-4-yl)-vinyl]-5-(2-trifluoromethyl-phenyl)-1H-benzimidazole hydrochloride (Cpd 53)

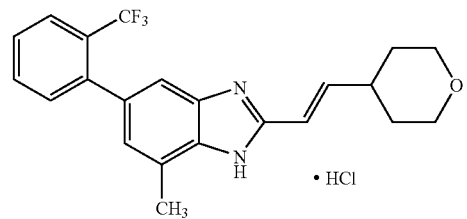

Following the procedure as described in Example 3, STEP A and STEP B, the procedure described in Example 5, STEP B and the procedure described in Example 3, STEP E, the title compound was prepared from 4-bromo-2-methyl-6-nitrophenylamine (154 mg, 0.519 mmol) and (E)-3-(tetrahydropyran-4-yl)-acrylic acid (prepared as described in PCT Publication WO 2005/101989 (A2,A3), 105 mg, 0.675 mmol) and was obtained as a pale yellow solid.

$^1$H-NMR (400 MHz; CD$_3$OD) δ: 7.85 (d, J=7.3 Hz, 1H), 7.72 (t, J=7.3 Hz, 1H), 7.63 (t, J=7.6 Hz, 1H), 7.43-7.50 (m, 2H), 7.33 (s, 1H), 7.19-7.30 (m, 1H), 6.67 (dd, J=16.3, 1.4 Hz, 1H), 4.01-4.10 (m, 2H), 3.58 (td, J=11.7, 1.9 Hz, 2H), 2.65-2.82 (m, 4H), 1.87 (dd, J=12.9, 1.8 Hz, 2H), 1.59-1.73 (m, 2H). Mass Spectrum (LCMS, APCI pos.) Calcd. For C$_{22}$H$_{21}$F$_3$N$_2$O: 387.2 (M+H). Found 387.3.

Example 7

(E)-2-[2-(Tetrahydro-pyran-4-yl)-vinyl]-5-(2-trifluoromethyl-pyridin-4-yl)-1H-benzimidazole hydrochloride (Cpd 54)

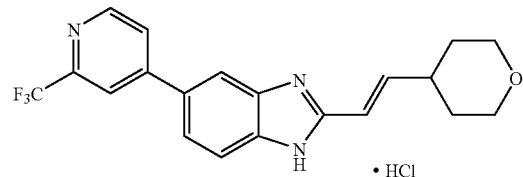

Step A: 2-Nitro-4-(4,4,5,5-tetramethyl-[1,3,2]dioxaborolan-2-yl)-phenylamine

A 100 mL round-bottomed flask was charged with 4,4,5,5,4',4',5',5'-octamethyl-[2,2']bi[[1,3,2]dioxaborolanyl] (3.86 g, 0.0152 mol), PdCl$_2$dppf (303 mg, 0.415 mmol), KOAc (4.07 g, 0.0415 mol), and dppf (230 mg, 0.415 mmol), was flushed with Argon, treated with a solution of 4-bromo-2-nitro-phenylamine (3.00 g, 0.0138 mol) in anhydrous dioxane (30 mL), and heated to 100° C. overnight. The cooled mixture was filtered through a frit, and the solid was washed with EtOAc. The filtrate was diluted with 200 mL EtOAc and washed twice with 150 mL brine. The combined aqueous layers were extracted four times with 100 mL EtOAc. The combined organic layers were dried over MgSO$_4$ and concentrated in vacuo. The residue was purified on a 200-g Sepra Si 50 SPE column (Isco system: flow rate=40 mL/min; eluting with EtOAc/hexane, 10:90, v/v over 15 min and 10:90 to 40:60, v/v over 25 min). The chromatography was repeated as above to yield 2-Nitro-4-(4,4,5,5-tetramethyl-[1,3,2]dioxaborolan-2-yl)-phenylamine as a bright yellow solid.

$^1$H-NMR (400 MHz; CDCl$_3$) δ: 8.59 (s, 1H), 7.72 (d, J=8.6 Hz, 1H), 6.77 (d, J=8.3 Hz, 1H), 6.20 (br. s., 2H), 1.33 (s, 12H). Mass Spectrum (LCMS, ESI pos.) Calcd. For C$_{12}$H$_{17}$BN$_2$O$_4$: 265.1 (M+H). Found 265.1.

Step B: 2-Nitro-4-(2-trifluoromethyl-pyridin-4-yl)-phenylamine

Following the procedure as described in Example 2, STEP A, the title compound was prepared from 2-nitro-4-(4,4,5,5-tetramethyl-[1,3,2]dioxaborolan-2-yl)-phenylamine (0.300 g, 1.14 mmol, as prepared in the previous step) and 4-chloro-2-trifluoromethyl-pyridine hydrochloride (322 mg, 1.48 mmol) and was obtained as an orange solid.

$^1$H-NMR (400 MHz; CDCl$_3$) δ: 8.98 (s, 1H), 8.82 (d, J=5.1 Hz, 1H), 8.17 (d, J=2.0 Hz, 1H), 7.35-7.42 (m, 1H), 7.30 (d, J=5.1 Hz, 1H), 6.90 (d, J=8.6 Hz, 1H), 6.25 (br. s., 2H). Mass Spectrum (LCMS, ESI pos.) Calcd. For C$_{12}$H$_8$F$_3$N$_3$O$_2$: 284.1 (M+H). Found 284.1.

Step C: (E)-N-[2-Nitro-4-(2-trifluoromethyl-pyridin-4-yl)-phenyl]-3-(tetrahydro-pyran-4-yl)-acrylamide Following the procedure as described in Example 3, STEP B, the title compound was prepared from 2-nitro-4-(2-trifluoromethyl-pyridin-4-yl)-phenylamine (84.5 mg, 0.298 mmol, as prepared in the previous step) and (E)-3-(tetrahydro-pyran-4-yl)-acrylic acid (prepared as described in PCT Publication WO 2005/101989 (A2, A3), 60.5 mg, 0.388 mmol) and was obtained as a yellow solid.

Mass Spectrum (LCMS, ESI pos.) Calcd. For C$_{20}$H$_{18}$F$_3$N$_3$O$_4$: 422.1 (M+H). Found 422.1.

Step D: (E)-2-[2-(Tetrahydro-pyran-4-yl)-vinyl]-5-(2-trifluoromethyl-pyridin-4-yl)-1H-benzimidazole Following the procedure as described in Example 8, STEP C, which follows herein, the title compound was prepared from (E)-N-[2-nitro-4-(2-trifluoromethyl-pyridin-4-yl)-phenyl]-3-(tetrahydro-pyran-4-yl)-acrylamide (98.0 mg, 0.233 mmol, as prepared in the previous step) and was obtained as a colorless glassy solid.

Mass Spectrum (LCMS, ESI pos.) Calcd. For C$_{20}$H$_{18}$F$_3$N$_3$O: 374.1 (M+H). Found 374.2.

Step E: (E)-2-[2-(Tetrahydro-pyran-4-yl)-vinyl-]-5-(2-trifluoromethyl-pyridin-4-yl)-1H-benzoimidazole hydrochloride Following the procedure as described in Example 1, STEP D, the title compound was prepared from (E)-2-[2-(tetrahydro-pyran-4-yl)-vinyl]-5-(2-trifluoromethyl-pyridin-4-yl)-1H-benzimidazole (58.0 mg, 0.155 mmol, prepared as in STEP D above) and was obtained as a pale yellow solid.

$^1$H-NMR (400 MHz; CD$_3$OD) δ: 9.03 (s, 1H), 8.90 (d, J=5.1 Hz, 1H), 7.87 (d, J=8.3 Hz, 1H), 7.77 (s, 1H), 7.55-7.62 (m, 2H), 7.22 (dd, J=16.3, 6.7 Hz, 1H), 6.68 (dd, J=16.4, 1.5 Hz, 1H), 4.05 (dt, J=9.5, 2.2 Hz, 2H), 3.57 (td, J=11.7, 2.1 Hz, 2H), 2.69-2.81 (m, 1H), 1.86 (dd, J=12.9, 1.8 Hz, 2H), 1.60-1.72 (m, 2H). Mass Spectrum (LCMS, ESI pos.) Calcd. For C$_{20}$H$_{18}$F$_3$N$_3$O: 374.1 (M+H). Found 374.2.

Compounds #55-56 were similarly prepared according to the procedure as described in Example 7 above, with selection and substitution of suitable reagents and starting materials. The Table below lists measured 1HMR and Mass Spec values for the prepared Compounds #55-56.

| Cpd | Compound Name; Measured $^1$HNMR and Mass Spec |
| --- | --- |
| 55 | (E)-2-(2-Cyclohexyl-vinyl)-5-(2-trifluoromethyl-pyridin-4-yl)-1H-benzimidazole hydrochloride<br>$^1$H-NMR (400 MHz; CD$_3$OD) δ: 9.02 (s, 1H), 8.88 (d, J = 5.1 Hz, 1H), 7.81 (d, J = 8.6 Hz, 1H), 7.72 (s, 1H), 7.57 (d, J = 5.1 Hz, 1H), 7.52 (d, J = 8.6 Hz, 1H), 7.18 (dd, J = 16.4, 7.1 Hz, 1H), 6.61 (dd, J = 16.3, 1.4 Hz, 1H), 2.37-2.50 (m, 1H), 1.95 (d, J = 12.6 Hz, 2H), 1.87 (dt, J = 12.8, 3.3 Hz, 2H), 1.28-1.52 (m, 6H)<br>Mass Spectrum (LCMS, APCI pos.) Calcd. For C$_{21}$H$_{20}$F$_3$N$_3$: 372.2 (M + H), Found 372.2. |
| 56 | (E)-2-(2-Cyclohexyl-vinyl)-5-(2-trifluoromethyl-pyridin-3-yl)-1H-benzimidazole hydrochloride<br>$^1$H-NMR (400 MHz; CD$_3$OD) δ: 8.75-8.80 (m, 1H), 7.93-8.03 (m, 1H), 7.73-7.86 (m, 2H), 7.71 (s, 1H), 7.54 (d, J = 8.6 Hz, 1H), 7.21 (dd, J = 16.3, 6.9, 4.0 Hz, 1H), 6.62 (d, J = 16.2 Hz, 1H), 2.37-2.53 (m, 1H), 1.92-2.00 (m, 2H), 1.83-1.92 (m, 2H), 1.72-1.83 (m, 1H), 1.25-1.53 (m, 7H)<br>Mass Spectrum (LCMS, APCI pos.) Calcd. For C$_{21}$H$_{20}$F$_3$N$_3$: 372.2 (M + H), Found 372.3. (2 too many) |

Example 8

(E)-2-(2-Cyclohexyl-vinyl)-5-(2-fluoro-6-trifluoromethyl-phenyl)-1H-benzimidazole (Cpd-57)

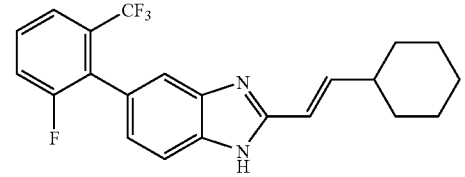

Step A: 6'-Fluoro-3-nitro-2'-trifluoromethyl-biphenyl-4-ylamine

A mixture of 2-nitro-4-(4,4,5,5-tetramethyl-[1,3,2]dioxaborolan-2-yl)-phenylamine (264 mg, 1.00 mmol, as prepared in Example 17, step A) and 2-bromo-1-fluoro-3-trifluoromethyl-benzene (243 mg, 1.00 mmol) in DME (5 mL) and 2 M aqueous $Na_2CO_3$ (4 mL, 8 mmol) was degassed via sonication, placed under argon and treated with $Pd(PPh_3)_4$ (115 mg, 0.100 mmol). The resulting mixture was heated at 80° C. for 16 h and allowed to cool to room temperature. The resulting mixture was diluted with EtOAc (10 mL) and washed twice with water (10 mL). The aqueous layer was extracted with additional EtOAc (10 mL), and the combined organic layers were dried over $Na_2SO_4$ and concentrated in vacuo. The residue was purified on silica (EtOAc/hexanes, 0:100 to 50:50, v/v) to yield 6'-fluoro-3-nitro-2'-trifluoromethyl-biphenyl-4-yl-amine.

$^1$H-NMR (CDCl$_3$) δ: 8.11 (d, J=2.0 Hz, 1H), 7.56-7.60 (m, 1H), 7.49 (td, J=7.9, 5.4 Hz, 1H), 7.28-7.39 (m, 2H), 6.88 (d, J=8.6 Hz, 1H), 6.20 (br. s., 2H)

Step B: 3-Cyclohexyl-N-(6'-fluoro-3-nitro-2'-trifluoromethyl-biphenyl-4-yl)-acrylamide To a solution of 6'-fluoro-3-nitro-2'-trifluoromethyl-biphenyl-4-yl-amine (150 mg, 0.500 mmol, prepared as in STEP A above) in DMF (10 mL) was added 60% NaH (120 mg, 3 mmol) portion wise. The resulting mixture was stirred at room temperature for 15 min. and treated with 3-cyclohexyl-acryloyl chloride (172 mg, 1.00 mmol) in DMF (2 mL). The resulting mixture was stirred overnight and poured into saturated aqueous ammonium chloride solution (10 mL). The aqueous layer was extracted thrice with EtOAc (10 mL). The EtOAc layers were combined, dried over $Na_2SO_4$ and concentrated. The residue was purified on silica (EtOAc/hexane, 0:100 to 100:0, v/v) to yield 3-cyclohexyl-N-(6'-fluoro-3-nitro-2'-trifluoromethyl-biphenyl-4-yl)-acrylamide.

$^1$H-NMR (CDCl$_3$) δ: 10.58 (s, 1H), 9.02 (d, J=8.8 Hz, 1H), 8.21 (d, J=2.0 Hz, 1H), 7.57-7.63 (m, 2H), 7.54 (m, 1H), 7.34-7.41 (m, 1H), 6.99-7.07 (m, 1H), 5.99 (dd, 1H), 2.19-2.30 (m, 1H), 1.66-1.89 (m, 5H), 1.15-1.41 (m, 5H).

Step C: 2-(2-Cyclohexyl-vinyl)-5-(2-fluoro-6-trifluoromethyl-phenyl)-1H-benzimidazole To a solution of 3-cyclohexyl-N-(6'-fluoro-3-nitro-2'-trifluoromethyl-biphenyl-4-yl)-acrylamide (135 mg, 0.309 mmol, prepared as in STEP B above) in EtOH (4 mL) and HOAc (2 mL) was added Fe powder (86.3 mg, 1.54 mmol). The resulting mixture was heated at reflux overnight. The resulting mixture was allowed to cool to room temperature and filtered. The filtrate was concentrated. The residue was dissolved in DCM with heating and sonication. The DCM layer was washed with 10 mL saturated aqueous $NaHCO_3$, separated, dried over $Na_2SO_4$ and concentrated. The residue obtained was purified on silica (EtOAc/hexane, 0:100 to 100:0, v/v) to yield 2-(2-Cyclohexyl-vinyl)-5-(2-fluoro-6-trifluoromethyl-phenyl)-1H-benzimidazole.

$^1$H-NMR (CD$_3$OD) δ: 10.55 (br. s., 1H), 7.37-7.79 (m, 4H), 7.33 (t, J=8.2 Hz, 1H), 7.14 (d, J=8.3 Hz, 1H), 6.76 (dd, J=16.2, 6.8 Hz, 1H), 6.49 (dd, J=16.2, 1.3 Hz, 1H), 2.13-2.27 (m, 1H), 1.58-1.87 (m, 5H), 1.07-1.37 (m, 5H). Mass Spectrum (LCMS, ESI pos.) Calcd. For $C_{22}H_{20}F_4N_2$: 489.2 (M+H). Found 489.4.

Compounds #58-65 were similarly prepared according to the procedure as described in Example 8 above, with selection and substitution of suitable reagents and starting materials. The Table below lists measured 1 HMR and Mass Spec values for the prepared Compounds #58-62.

| ID No. | Compound Name; Measured $^1$HNMR and Mass Spec |
|---|---|
| 58 | (E)-5-(2,6-Bis-trifluoromethyl-phenyl)-2-(2-cyclohexyl-vinyl)-1H-benzimidazole<br>$^1$H-NMR (CD$_3$OD) δ: 7.92-7.99 (m, 2H), 7.61-7.68 (m, 1H), 7.33-7.50 (m, 2H), 7.01-7.08 (m, 1H), 6.71-6.80 (m, 1H), 6.37-6.45 (m, 1H), 2.16-2.28 (m, 1H), 1.63-1.89 (m, 5H), 1.27 (m, 6H)<br>Mass Spectrum (LCMS, ESI pos.) Calcd. For $C_{23}H_{20}F_6N_2$: 439.2 (M + H), Found 439.3. |
| 59 | (E)-2-(2-Cyclohexyl-vinyl)-5-(2-fluoro-6-trifluoromethoxy-phenyl)-1H-benzimidazole<br>$^1$H-NMR (CDCl$_3$) δ: 12.57 (br. s., 1H), 7.60-7.71 (m, 2H), 7.29-7.39 (m, 1H), 7.23 (d, J = 8.3 Hz, 1H), 7.15-7.21 (m, 1H), 7.08-7.15 (m, 1H), 6.87 (dd, J = 16.2, 6.8 Hz, 1H), 6.54-6.62 (m, 1H), 2.09-2.21 (m, 1H), 1.57-1.78 (m, 5H), 1.18-1.31 (m, 2H), 1.01-1.17 (m, 3H)<br>Mass Spectrum (LCMS, ESI pos.) Calcd. For $C_{22}H_{20}F_4N_2O$: 405.2 (M + H). Found 405.3. |
| 60 | (E)-2-(2-Cyclohexyl-vinyl)-5-(3-trifluoromethyl-pyridin-2-yl)-1H-benzimidazole<br>$^1$H-NMR (CDCl$_3$-d, 400 MHz): δ = 8.80 (d, J = 3.8 Hz, 1 H), 8.03-8.08 (m, 1 H), 7.70 (br. s., 1 H), 7.55 (d, J = 6.3 Hz, 1 H), 7.39 (dd, J = 7.8, 5.1 Hz, 1 H), 7.34 (d, J = 8.3 Hz, 1 H), 6.76 (dd, J = 16.2, 6.8 Hz, 1 H), 6.43 (d, J = 15.4 Hz, 1 H), 2.01-2.13 (m, 1 H), 1.54-1.74 (m, 5 H), 0.95-1.23 (m, 5 H)<br>Mass Spectrum (LCMS, ESI pos.) Calcd. For $C_{21}H_{20}F_3N_3$: 372.1 (M + H). Found 372.3. |
| 61 | (E)-5-(2,6-Difluoro-phenyl)-2[2-(tetrahydro-pyran-4-yl)-vinyl]-1H-benzoimidazole hydrochloride<br>$^1$H NMR (400 MHz; CD$_3$OD) δ: 7.79 (d, J = 8.3 Hz, 1H), 7.76 (s, 1H), 7.54-7.60 (m, 1H), 7.47 (tt, J = 8.4, 6.3 Hz, 1H), 7.07-7.19 (m, 3H), 6.64 (dd, J = 16.4, 1.5 Hz, 1H), 4.04 (dt, J = 9.5, 2.3 Hz, 2H), 3.52-3.61 (m, 2H), 2.64-2.77 (m, 1H), 1.80-1.89 (m, 2H), 1.58-1.71 (m, 2H)<br>Mass Spectrum (LCMS, APCI pos.) Calcd. For $C_{20}H_{18}F_2N_2O$: 341.1 (M + H), Found 341.3. |

| ID No. | Compound Name; Measured $^1$HNMR and Mass Spec |
|---|---|
| 62 | (E)-2-[2-(Tetrahydro-pyran-4-yl)-vinyl]-5-(3-trifluoromethyl-pyridin-2-yl)-1H-benzoimidazole hydrochloride<br>$^1$H NMR (400 MHz; CD$_3$OD) δ: 8.87-8.93 (m, 1H), 8.36 (dd, J = 8.1, 1.3 Hz, 1H), 7.83-7.89 (m, 2H), 7.67-7.76 (m, 2H), 7.22 (dd, J = 16.4, 6.6 Hz, 1H), 6.69 (dd, J = 16.3, 1.4 Hz, 1H), 4.05 (dt, J = 9.5, 2.2 Hz, 2H), 3.57 (td, J = 11.7, 2.1 Hz, 2H), 2.69-2.81 (m, 1H), 1.86 (dt, J = 11.1, 1.8 Hz, 2H), 1.60-1.73 (m, 2H)<br>Mass Spectrum (LCMS, APCI pos.) Calcd. For C$_{20}$H$_{18}$F$_3$N$_3$O: 374.1 (M + H), Found 374.3. |
| 63 | (E)-2-[2-(4,4-Dimethyl-cyclohexyl)-vinyl]-7-methyl-5-(2-trifluoromethyl-phenyl)-1H-benzoimidazole hydrochloride<br>$^1$H NMR (400 MHz; CD$_3$OD) δ: 7.73 (d, J = 7.8 Hz, 1H), 7.60 (t, J = 7.6 Hz, 1H), 7.52 (t, J = 7.7 Hz, 1H), 7.36 (s, 1H), 7.33 (d, J = 7.3 Hz, 1H), 7.16-7.25 (m, 2H), 6.53 (d, J = 16.4 Hz, 1H), 2.58 (s, 3H), 2.22-2.34 (m, 1H), 1.64-1.73 (m, 2H), 1.38-1.51 (m, 4H), 1.25-1.33 (m, 2H), 0.88 (s, 6H)<br>Mass Spectrum (LCMS, APCI pos.) Calcd. For C$_{25}$H$_{27}$F$_3$N$_2$: 413.2 (M + H), Found 413.4. |
| 64 | (E)-2-[2-(4,4-Dimethyl-cyclohexyl)-vinyl]-5-(2-trifluoromethyl-phenyl)-1H-benzoimidazole hydrochloride<br>$^1$H NMR (400 MHz; CD$_3$OD) δ: 7.75 (d, J = 7.8 Hz, 1H), 7.69 (d, J = 8.6 Hz, 1H), 7.58-7.65 (m, 1H), 7.56 (s, 1H), 7.50-7.56 (m, 1H), 7.40-7.46 (m, 1H), 7.36 (d, J = 7.6 Hz, 1H), 7.17 (dd, J = 16.3, 6.9 Hz, 1H), 6.54 (dd, J = 16.4, 1.3 Hz, 1H), 2.22-2.34 (m, 1H), 1.63-1.73 (m, 2H), 1.38-1.51 (m, 4H), 1.21-1.33 (m, 2H), 0.88 (s, 6H)<br>Mass Spectrum (LCMS, APCI pos.) Calcd. For C$_{24}$H$_{25}$F$_3$N$_2$: 399.2 (M + H), Found 399.3. |
| 65 | (E)-5-(2,6-Difluoro-phenyl)-2-[2-(4,4-dimethyl-cyclohexyl)-vinyl]-1H-benzoimidazole trifluoroacetic acid salt<br>$^1$H NMR (400 MHz; CD$_3$OD) δ: 7.72 (dd, J = 8.5, 0.6 Hz, 1H), 7.69 (s, 1H), 7.50-7.55 (m, 1H), 7.37 (tt, J = 8.4, 6.3 Hz, 1H), 7.14 (dd, J = 16.3, 6.9 Hz, 1H), 7.00-7.08 (m, 2H), 6.53 (dd, J = 16.4, 1.5 Hz, 1H), 2.19-2.33 (m, 1H), 1.63-1.72 (m, 2H), 1.37-1.50 (m, 4H), 1.21-1.32 (m, 2H), 0.88 (s, 6H)<br>Mass Spectrum (LCMS, APCI pos.) Calcd. For C$_{23}$H$_{24}$F$_2$N$_2$: 367.2 (M + H), Found 367.3. |

Example 9

(E)-2-[2-(4-Methyl-tetrahydro-pyran-4-yl)-vinyl]-5-(2-trifluoromethyl-phenyl)-1H-benzimidazole (Cpd 66)

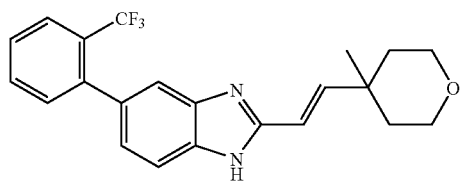

Step A: 3-(4-Methyl-tetrahydro-pyran-4-yl)-acrylic acid ethyl ester

To a solution of 4-methyl-tetrahydro-pyran-4-carbaldehyde (prepared as described in PCT Publication WO 2006/001752 A1 (1.36 g, 10.6 mmol) in THF (20 mL) ethyl(triphenylphosphoranylidene)acetate (4.1 g, 10 mmol) was added. The resulting mixture was heated at reflux for 16 h. The resulting mixture was allowed to cool to room temperature and filtered. The filtrate was concentrated and the residue was suspended in diethyl ether (100 mL) and sonicated for 15 min. The solid formed was removed by filtration and the filtrate was concentrated. The resulting residue was purified on silica (EtOAc/hexane, 0:100 to 50:50, v/v) to yield 3-(4-methyl-tetrahydro-pyran-4-yl)-acrylic acid ethyl ester.

$^1$H-NMR (CDCl$_3$) δ: 6.95 (d, J=16.2 Hz, 1H), 5.79 (d, J=15.9 Hz, 1H), 4.21 (q, J=7.1 Hz, 2H), 3.59-3.76 (m, 4H), 1.49-1.74 (m, 4H), 1.31 (t, J=7.2 Hz, 3H), 1.14 (s, 3H).

Step B: 3-(4-Methyl-tetrahydro-pyran-4-yl)-acrylic acid

To a solution of 3-(4-methyl-tetrahydro-pyran-4-yl)-acrylic acid ethyl ester (396 mg, 2.00 mmol, prepared as in STEP A above) in EtOH (10 mL), 6N aqueous NaOH (1 mL) was added dropwise. The resulting mixture was stirred at room temperature over night. The resulting mixture was concentrated and the resulting residue was dissolved in 20 mL of water. The resulting solution was washed twice with diethyl ether (10 mL), and the aqueous layer was acidified with 6N HCl and extracted thrice with DCM (20 mL). The DCM layers were combined, dried over Na$_2$SO$_4$ and concentrated in vacuo to yield 3-(4-methyl-tetrahydro-pyran-4-yl)-acrylic acid, which was used in next step without further purification.

$^1$H-NMR (CDCl$_3$) δ: 11.58-11.77 (m, 1H), 7.03 (d, J=15.9 Hz, 1H), 5.79 (d, J=16.2 Hz, 1H), 3.68-3.79 (m, 2H), 3.63 (m, 2H), 1.70 (m, 2H), 1.47-1.58 (m, 2H), 1.13 (s, 3H).

Step C: (E)-2-[2-(4-Methyl-tetrahydro-pyran-4-yl)-vinyl]-5-(2-trifluoromethyl-phenyl)-1H-benzimidazole (E)-2-[2-(4-Methyl-tetrahydro-pyran-4-yl)-vinyl]-5-(2-trifluoromethyl-phenyl)-1H-benzimidazole was prepared from the acid chloride of 3-(4-methyl-tetrahydro-pyran-4-yl)-acrylic acid (prepared as in STEP B above) and 3-nitro-2'-trifluoromethyl-biphenyl-4-ylamine (prepared as described in Example 3, STEP A) following the procedure as described in Example 8, STEP C.

$^1$H-NMR (CD$_3$OD, 400 MHz): δ=7.78 (m, 1H), 7.61-7.67 (m, 1H), 7.50-7.58 (m, 2H), 7.39-7.49 (m, 2H), 7.13-7.20 (m, 1H), 6.86-6.95 (m, 1H), 6.45-6.54 (m, 1H), 3.68-3.84 (m, 4H), 1.76-1.86 (m, 2H), 1.58-1.68 (m, 2H), 1.25 (s, 3H). Mass Spectrum (LCMS, ESI pos.) Calcd. For C$_{22}$H$_{21}$F$_3$N$_2$O: 387.1 (M+H). Found 387.3.

Compound #67, (E)-5-(2,6-Bis-trifluoromethyl-phenyl)-2-[2-(4-methyl-tetrahydro-pyran-4-yl)-vinyl]-1H-benzimidazole, was similarly prepared according to the procedure as described in Example 9 above, with selection and substitution of suitable reagents and starting materials. Measured $^1$H NMR and Mass Spec for the prepared compound were as follows: $^1$H-NMR (CD$_3$OD) δ: 8.07 (d, 2H), 7.78 (t, J=8.0 Hz, 1H), 7.52 (br. s., 1H), 7.39 (br. s., 1H), 7.09 (d, J=8.3 Hz, 1H), 6.91 (d, J=16.7 Hz, 1H), 6.51 (d, J=16.7 Hz, 1H), 3.69-3.85 (m, 4H), 1.84 (m, 2H), 1.59-1.69 (m, 2H), 1.23 (m, 3H). Mass Spectrum (LCMS, ESI pos.) Calcd. For C$_{23}$H$_{20}$F$_6$N$_2$O: 455.1 (M+H). Found 455.3.

Example 10

(E)-2-(2-Cyclohexyl-propenyl)-5-(2-trifluoromethyl-phenyl)-1H-benzimidazole (Cpd 68)

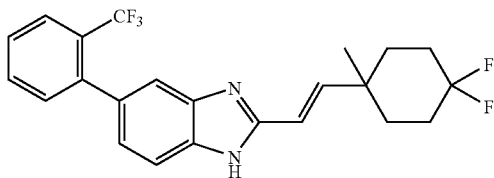

(E)-2-(2-Cyclohexyl-propenyl)-5-(2-trifluoromethyl-phenyl)-1H-benzimidazole was prepared from 3-(4,4-difluoro-cyclohexyl)-acryloyl chloride (prepared from 4,4-difluoro-cyclohexanecarboxylic acid ethyl ester utilizing a procedure analogous to the preparation of 4-methyl-tetrahydro-pyran-4-carbaldehyde in Example 9) and 3-nitro-2'-trifluoromethyl-biphenyl-4-ylamine (prepared as described in Example 3, STEP A) as described in Example 9, STEPS A-C.

$^1$H-NMR (CD$_3$OD) δ: 7.75 (d, J=7.8 Hz, 1H), 7.34-7.64 (m, 5H), 7.16 (d, J=8.3 Hz, 1H), 6.87 (d, J=16.7 Hz, 1H), 6.53 (d, J=16.7 Hz, 1H), 1.56-1.99 (m, 8H), 1.18 (s, 3H). Mass Spectrum (LCMS, ESI pos.) Calcd. For C$_{23}$H$_{21}$F$_5$N$_2$: 421.1 (M+H). Found 421.2.

Example 11

(E)-2-(2-Cyclohexyl-propenyl)-5-(2-trifluoromethyl-phenyl)-1H-benzimidazole (Cpd 69)

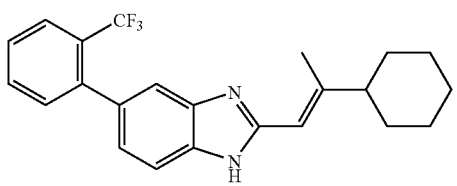

(E)-2-(2-Cyclohexyl-propenyl)-5-(2-trifluoromethyl-phenyl)-1H-benzimidazole was prepared from the acid chloride of 3-cyclohexyl-but-2-enoic acid (prepared as described in YOUNG, S. T. et al., "Synthetic Studies in the Fumagillin Series", *J. Org. Chem.*, 1963, pp 928-932, Vol. 28) and 3-nitro-2'-trifluoromethyl-biphenyl-4-ylamine (prepared as described in Example 3, STEP A) according to the procedures s described in Example 3, STEPS B, C and D.

$^1$H-NMR (CDCl$_3$) δ: 10.87-11.21 (m, 1H), 7.74 (d, J=7.3 Hz, 1H), 7.48-7.67 (m, 3H), 7.41-7.48 (m, 1H), 7.37 (d, J=7.6 Hz, 1H), 7.17 (d, J=8.1 Hz, 1H), 6.34 (s, 1H), 2.28 (s, 3H), 1.99-2.09 (m, 1H), 1.58-1.81 (m, 5H), 1.10-1.36 (m, 5H). Mass Spectrum (LCMS, ESI pos.) Calcd. For C$_{23}$H$_{23}$F$_3$N$_2$: 385.2 (M+H). Found 385.5.

Example 12

(E)-2-[2-(4-Bromo-bicyclo[2.2.2]oct-1-yl)-vinyl]-5-(2-trifluoromethyl-phenyl)-1H-benzoimidazole (Cpd 70)

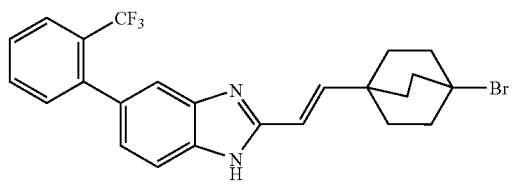

(E)-2-[2-(4-Bromo-bicyclo[2.2.2]oct-1-yl)-vinyl]-5-(2-trifluoromethyl-phenyl)-1H-benzoimidazole was prepared from 3-(4-bromo-bicyclo[2.2.2]oct-1-yl)-acryloyl chloride (prepared from 4-bromo-bicyclo[2.2.2]octane-1-carboxylic acid methyl ester utilizing a procedure analogues to the preparation of 4-methyl-tetrahydro-pyran-4-carbaldehyde in Example 9) and 3-nitro-2'-trifluoromethyl-biphenyl-4-ylamine (prepared as described in Example 3, STEP A) according to the procedure as described in Example 9, STEPS A-C.

$^1$H-NMR (CD$_3$OD) δ: 7.77 (d, 1H), 7.58-7.64 (m, 1H), 7.49-7.56 (m, 2H), 7.38-7.44 (m, 2H), 7.12-7.18 (m, 1H), 6.68 (d, J=16.4 Hz, 1H), 6.31 (d, J=16.4 Hz, 1H), 2.24-2.34 (m, 6H), 1.80-1.89 (m, 6H). Mass Spectrum (LCMS, ESI pos.) Calcd. For C$_{24}$H$_{22}$BrF$_3$N$_2$: 476.3 (M+H). Found 477.3.

Example 13

2-(2-Cyclohexyl-vinyl)-5-(2-trifluoromethyl-phenyl)-1H-benzoimidazole hydrochloride (Compd. 71)

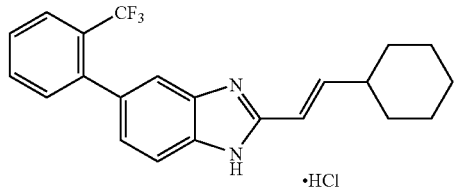

Step A: 3-Cyclohexyl-acrylic acid

A solution of malonic acid (30 g, 0.29 mol), cyclohexanecarbaldehyde (17.3 ml, 0.14 mol) and piperidine (2.9 ml, 0.029 mol) in pyridine (90 ml) was stirred at 70° C. for 18 h.

The resulting solution was allowed to cool to room temperature and then water (200 ml) was added. The resulting solution was acidified to pH 2 (litmus) using 1N HCl. The acidic aqueous solution was extracted thrice with ethyl acetate. The ethyl acetate extracts were pooled, washed successively with water, brine, dried over sodium sulfate, filtered and concentrated to yield 3-cyclohexyl-acrylic acid.

$^1$H-NMR (400 MHz, DMSO $d_6$) δ (ppm): 12.1 (s, 1H), 6.73-6.80 (dd, J=6.82, 15.7 Hz, 1H), 5.70-5.72 (dd, J=1.26, 15.7 Hz, 1H), 2.09-2.19 (m, 1H), 1.60-1.75 (m, 5H), 1.05-1.32 (m, 5H).

Step B: 3-Cyclohexyl-acryloyl chloride

A solution of 3-cyclohexyl-acrylic acid (5.0 g, 32.5 mmol) and oxalyl chloride (3.4 ml, 34.0 mmol) in anhydrous DCM (50 ml) was treated with one drop of dimethylformamide. The resulting solution was stirred at room temperature for 18 h, concentrated and used directly in the next step.

Step C:
5-Bromo-2-(2-cyclohexyl-vinyl)-1H-benzoimidazole

To a solution of 4-bromo-benzene-1,2-diamine (3.0 g, 16.1 mmol) in anhydrous toluene (50 ml) was added a solution of 3-cyclohexyl-acryloyl chloride (as prepared in STEP B above, 32.5 mmol) in toluene (5 ml). The resulting solution was stirred at 40° C. for 6 h. To the resulting solution was added p-toluenesulfonic acid (3.0 g, 16 mmol) and heated to reflux for 18 h. The resulting solution was concentrated. The residue obtained was partitioned between ethyl acetate and a saturated solution of sodium bicarbonate. The layers were separated. The organic layer was washed successively with saturated sodium bicarbonate, water, brine, then dried over sodium sulfate, filtered and concentrated. The residue was chromatographed using a silica gel to yield 5-bromo-2-(2-cyclohexyl-vinyl)-1H-benzoimidazole.

$^1$H-NMR (400 MHz, DMSO $d_6$) δ (ppm): 12.58 (bs, 1H), 7.4-7.70 (m, 2H), 7.22-7.30 (m, 1H), 6.74-6.84 (m, 1H), 6.34-6.42 (dd, J=1.26, 16.2 Hz, 1H), 2.18-2.24 (m, 1H), 1.60-1.80 (m, 5H), 1.20-1.40 (m, 5H). Mass Spectrum (LCMS, ESI pos.) Calcd. For $C_{15}H_{17}BrN_2$: 305.1, 307.1 (M+H). Found, 305.2, 307.2

Step D: 2-(2-Cyclohexyl-vinyl)-5-(2-trifluoromethyl-phenyl)-1H-benzoimidazole

A solution of 5-bBromo-2-(2-cyclohexyl-vinyl)-1H-benzoimidazole (2.0 g, 6.6 mmol), 2-trifluoromethylphenylboronic acid (2.5 g, 13 mmol), dichloro[1,1'-bis(diphenylphosphino)ferrocene]palladium (II) dichloromethane adduct (1.1 g, 1.3 mmol) in dimethoxyethane (55 ml) and 2M sodium carbonate (27 ml, 54 mmol) was stirred at 95° C. for 18 h. The resulting solution was cooled to room temperature. The resulting solution was poured into a solution of ethyl acetate and water (1:1, 50 ml). The layers were separated. The organic layer was washed with brine, then dried over sodium sulfate, filtered and concentrated. The residue was purified on silica gel using ethyl acetate/hexanes 3:7 as eluent to yield 2-(2-Cyclohexyl-vinyl)-5-(2-trifluoromethyl-phenyl)-1H-benzoimidazole.

$^1$H NMR (400 MHz, DMSO $d_6$) δ (ppm): 12.5-12.6 (m, 1H), 7.80-7.83 ((m, 1H), 7.68-7.75 (m, 1H), 7.54-7.64 (m, 2H), 7.32-7.48 (m, 2H) 7.04-7.10 (m, 1H), 6.76-6.84 (m, 1H), 6.36-6.44 (d, J=16 Hz, 1H), 2.20-2.30 (m, 1H), 1.60-1.85 (m, 5H), 1.16-1.40 (m, 5H). Mass Spectrum (LCMS, ESI pos.) Calcd. For $C_{22}H_{21}F_3N_2$: 371.2 (M+H). Found 371.2.

Step E: 2-(2-Cyclohexyl-vinyl)-5-(2-trifluoromethyl-phenyl)-1H-benzoimidazole hydrochloride A solution of 2-(2-cyclohexyl-vinyl)-5-(2-trifluoromethyl-phenyl)-1H-benzoimidazole (0.25 g, 0.66 mmol) in ethyl ether (5 ml) was treated with 2M HCl in ethyl ether (0.36 ml, 0.73 mmol). After five minutes the resulting solution was concentrated and dried in vacuo to yield the title compound.

$^1$H-NMR (400 MHz, DMSO $d_6$) δ (ppm): 7.86-7.90 (d, J=7.4 Hz, 1H), 7.74-7.84 (m, 2H), 7.64-7.70 (m, 2H), 7.42-7.50 (m, 2H), 7.32-7.38 (m, 1H), 6.56-6.62 (d, J=16 Hz, 1H), 2.36-2.45 (br.s., 1H), 1.62-1.88 (m, 5H), 1.18-1.40 (m, 5H). Calcd. For $C_{22}H_{21}F_3N_2$: 371.2 (M+H). Found 371.2.

BIOLOGICAL EXAMPLES

Example 14

In Vitro Canine TRPM8 Functional Assay

The functional activity of representative compounds of the formula (I) of the present invention were measured by measuring changes in intracellular calcium concentration using a $Ca^{2+}$-sensitive fluorescent dye. The changes in fluorescent signal were monitored by a fluorescence plate reader, either a FLIPR™ (Molecular Devices) or FDSS (Hamamatsu). Increases in intracellular $Ca^{2+}$ concentration were readily detected upon activation with icilin.

HEK293 cells stably expressing canine TRPM8 were routinely grown as monolayers in Dulbecco's minimum essential medium supplemented with 10% FBS, 2 mM L-glutamine, 100 units/mL penicillin, 100 ug/mL streptomycin and 400 μg/mL G418. Cells were maintained in 5% $CO_2$ at 37° C. At 24 hrs prior to assay, cells were seeded in black wall, clear-base poly-D-lysine coated 384-well plates (BD Biosciences, NJ, USA) at a density of 5,000 cells per well in culture medium and grown overnight in 5% $CO_2$ at 37° C. On assay day, growth media was removed and cells were loaded with Calcium 3 Dye (Molecular Devices) for 35 min at 37° C., under 5% $CO_2$ and then for 25 min at room temperature and atmosphere. Subsequently, cells were tested for agonist-induced increases in intracellular $Ca^{2+}$ levels using FLIPR™ or FDSS. Cells were challenged with compounds of the formula (I) (at varying concentrations) and intracellular $Ca^{2+}$ was measured for 5 min prior to the addition of icilin to all wells to achieve a final concentration that produces approximately an 80% maximal response. $EC_{50}$ or $IC_{50}$ values for compounds of the present invention were determined from eight-point dose-response studies and represent the concentration of compound required to elicit or inhibit 50% of the maximal response, respectively.

Maximal fluorescence intensity (FI) achieved upon addition of icilin was exported from the FLIPR or FDSS software and further analyzed using GraphPad Prism 3.02 (Graph Pad Software Inc., CA, U.S.A.). Basal FI was subtracted prior to normalizing data to percent of maximal response. Curves were generated using the average of quadruplicate wells for each data point, were analyzed using nonlinear regression of either sigmoidal dose response or sigmoidal dose response (variable slope). Finally, the $EC_{50}$ and $IC_{50}$ values were calculated with the best-fit dose curve determined by GraphPad Prism Representative compounds of the present invention were tested according to the procedures as described in Example 14 above, with results as listed in Table 4, below.

TABLE 4

| ID No. | % Inh @ 0.2 µM | $IC_{50}$ (nM) |
|---|---|---|
| 1 | 93 | 14 |
| 2 | 96 | 110 |
| 3 | 103 | 7.0 |
| 4 | 103 | 3.0 |
| 5 | 18 | |
| 6 | 103 | 12 |
| 7 | 103 | 34 |
| 8 | 97 | 41 |
| 9 | 101 | 11 |
| 10 | 101 | 6.0 |
| 11 | 102 | 32 |
| 12 | 92 | 39 |
| 13 | 96 | 3.5 |
| 14 | 95 | 2.0 |
| 15 | 102 | 28 |
| 16 | 102 | 14 |
| 17 | 102 | 17 |
| 18 | 101 | 32 |
| 19 | 86 | 34 |
| 20 | 85 | 53 |
| 21 | 86 | 35 |
| 22 | 101 | 31 |
| 24 | 85 | 97 |
| 25 | 102 | 13 |
| 26 | 100 | 33 |
| 27 | 100 | 47 |
| 28 | 95 | 42 |
| 29 | 77 | 170 |
| 30 | 102 | 3.0 |
| 31 | 102 | 6.0 |
| 32 | 101 | 5.2 |
| 33 | 101 | 9.0 |
| 34 | 101 | 5.0 |
| 35 | 100 | 4.0 |
| 36 | 100 | 16 |
| 37 | 100 | 8.0 |
| 38 | 101 | 3.5 |
| 39 | 101 | 9.0 |
| 40 | 101 | 2.0 |
| 41 | 100 | 6.0 |
| 42 | 101 | 3.0 |
| 43 | 100 | 2.0 |
| 44 | 101 | 3.0 |
| 45 | 101 | 7.0 |
| 46 | 99 | 4.0 |
| 47 | 99 | 6.3 |
| 48 | 99 | 6.0 |
| 49 | 99 | 3.0 |
| 50 | 101 | 17 |
| 51 | 95 | 31 |
| 52 | 91 | 70 |
| 53 | 102 | 8.0 |
| 54 | 1 | |
| 55 | 76 | 50 |
| 56 | 99 | 11 |
| 57 | 101 | 8.0 |
| 58 | 83 | 9.0 |
| 59 | 96 | 6.0 |
| 60 | 92 | 45 |
| 61 | 97 | 32 |
| 62 | 92 | 21 |
| 63 | 97 | 12 |
| 64 | 98 | 23 |
| 65 | 96 | 55 |
| 66 | 101 | 31 |
| 67 | 100 | 13 |
| 68 | 101 | 30 |
| 69 | 102 | 11 |
| 70 | 97 | 11 |
| 71 | 94 | 9.0 |

Example 15

Inhibition of Icilin-Induced Behaviors in Rodents

Icilin was initially developed as a "super-cooling" compound by Delmar Chemicals Ltd. Subsequently it was shown to be one of the most potent known agonists of TRPM8 (MCKEMY, D. D., et al "Identification of a cold receptor reveals a general role for TRP channels in thermosensation", *Nature*, pp 52-58, Vol. 416 (6876)), having an $EC_{50}$=0.2 µM in stimulating calcium ion influx into TRPM8 transfected cells (BEHRENDT, H-J., et al., "Characterization of the mouse cold menthol receptor TRPM8 and vaniloid receptor type-1 VR1 using a fluormetric imaging plate reader (FLIPR) assay", *Brit J Pharmacol,* 2004, pp 737-745, Vol. 141(4)). Initial in vivo testing of icilin showed it to cause "wet-dog" shakes in rats. Similar shaking or jumping behavior was also evident in mice, rabbits, cats, dogs and monkeys. In humans, icilin produced a sensation of coolness on contact with mucous membranes, cold prickling when 0.1 mg was dropped on the tongue and coldness in the mouth, pharynx and chest lasting 30-60 minutes when 5-10 mg was ingested orally (WEI, E. T., et al., "AG-3-5: a chemical producing sensations of cold", *J Pharm Pharmacol.,* 1983, pp 110-112, Vol. 35). The inhibition or reversal of icilin-induced shaking behaviors in rodents provides evidence for the utility of TRPM8 antagonists in treating or preventing a disease or condition in a mammal in which the disease or condition is affected by the modulation of TRPM8 receptors.

Example 15a

Inhibition of Icilin-Induced "Wet-Dog" Shakes in Rats

Male Sprague Dawley rats (2200-450 g, Charles River Labs, n=6-9/treatment) were used to evaluate the ability of test compounds to block icilin-induced "wet-dog" shakes (WDS). The test compound was administered in 10% hydroxypropyl-β-cyclodextrin (HP β CD), p.o., 60 minutes before icilin. Icilin was then administered in 10% solutol/$H_2O$, at 3.0 mg/kg, i.p. and spontaneous "wet-dog" shakes were counted over a 10 minute period, 10 minutes following the icilin injection. Results for representative compounds of the present invention are presented in Table 5 below as a percent inhibition of shakes, which was calculated as % Inhibition=[1−(test compound WDS count/vehicle WDS count)]×100.

TABLE 5

| Icilin-induced "wet-dog" shakes | | | |
|---|---|---|---|
| ID No. | Dose (mg/kg) | Admin. Route | % Inhibition |
| 1 | 30 | p.o | 48 |
| 30 | 10 | p.o | 98 |
| 50 | 10 | p.o. | 89 |
| 58 | 10 | p.o. | 30 |
| 59 | 10 | p.o. | 75 |
| 71 | 30 | p.o. | 90 |

Example 15b—Prophetic Example

Reversal of Icilin-Induced Behaviors in Rats

Male Sprague Dawley rats (225-450 g, Charles River Labs, n=4-6/treatment) are used to evaluate the ability of selected compounds of the formula (I) to reverse icilin-induced "wet-dog" shakes. Icilin is administered in PEG-400 or 10% solutol/H$_2$O, at 1.0 or 3.0 mg/kg, i.p. and spontaneous "wet-dog" shakes (WDS) are counted 10-20 minutes post-icilin. Animals that exhibited 10 or more shakes are randomized into treatment groups and immediately administered test compound in an appropriate vehicle, such as hydroxypropyl-β-cyclodextrin (HP β CD), methocellulose, 10% Solutol, or H$_2$O, or the like, and by the appropriate route, such as i.p. or p.o. Spontaneous "wet-dog" shakes are counted 60-70 minutes after compound administration. Results are presented as a percent inhibition of shakes, which was calculated as [1−(test compound WDS count/vehicle WDS count)]×100.

Example 16—Prophetic Example

In Vivo Model for of Chronic Inflammatory Pain

Complete Freund's Adjuvant (CFA)-Induced Hyperalgesia

Intraplantar injection of complete Freund's adjuvant (CFA) in rodents results in a long-lasting inflammatory reaction, characterized by a pronounced hypersensitivity to both thermal and mechanical stimuli. This hypersensitivity peaks between 24-72 hours following injection and can last for several weeks. To assess whether a test compound reverses established hypersensitivity, a 100 μL intraplantar injection of CFA (suspended in a 1:1 emulsion of saline and heat-killed *Mycobacterium tuberculosis* in mineral oil) are injected into a single hind paw of Sprague-Dawley rats (typically males ranging from 150-350 g). This paradigm also may be conducted with a multiple dosing or a prophylactic dosing regime designed to alter the course of hyperalgesia development. This test predicts the analgesic, anti-allodynic and antihyperalgesic effect of numerous effective clinical agents, including acetaminophen, NSAIDS such as aspirin and ibuprofen, and opioids, such as morphine.

Example 16a—Prophetic Example

CFA-Induced Paw Radiant Heat Hypersensitivity

Each rat is placed in a test chamber on a warm glass surface and allowed to acclimate for approximately 10 minutes. A radiant thermal stimulus (beam of light) is then focused through the glass onto the plantar surface of each hind paw in turn. The thermal stimulus is automatically shut off by a photoelectric relay when the paw is moved or when the cut-off time is reached (20 seconds for radiant heat at ~5 Amps). An initial (baseline) response latency to the thermal stimulus is recorded for each animal prior to the injection of CFA. Twenty-four hours following intraplantar CFA injection, the response latency of the animal to the thermal stimulus is re-evaluated and compared to the animal's baseline response time. Only rats that exhibit at least a 25% reduction in response latency (i.e. hyperalgesia) are included in further analysis. Immediately following the post-CFA latency assessment, test compound or vehicle (usually Solutol, hydroxypropyl methylcellulose, hydroxypropyl beta-cyclodextrin or PEG-400) is administered i.p. or p.o. to rats. Post-compound treatment withdrawal latencies are assessed at fixed time intervals, typically 30, 60 and 120 minutes. The percent reversal (% R) of hypersensitivity is calculated according to the following formula:

$$\% \text{ Reversal} = \frac{(\text{Treatment Response} - CFA \text{ Response})}{(\text{Baseline Response} - CFA \text{ Response})} \times 100$$

Example 16b—Prophetic Example

CFA-Induced Paw Cold Hypersensitivity

Prior to intraplantar CFA injection, mice or rats are placed individually in elevated observation chambers having wire mesh floors. Through the mesh floor a series of three applications of acetone (0.04-0.10 mL/application) is sprayed onto the bottom of the paw using a multidose syringe device. A positive response takes the form of an abrupt withdrawal and licking of the paw. The cumulative duration of licking is recorded for each of the three trials which are then averaged to give the individual's response. Twenty-four hours following CFA injection acetone licking durations are markedly elevated implying a hypersensitivity to cooling. A test compound is assessed for its ability to return acetone-evoked paw licking durations to pre-CFA levels (typically near zero) following systemic administration. Percent inhibition is calculated as % Inhibition=[1−(treatment licking duration/vehicle licking duration)]×100.

Example 17—Prophetic Example

Chemically-Induced Abdominal Irritant Models of Visceral Pain

A chemical irritant (such as acetic acid, kaolin, bradykinin, phenyl-p-(benzo)quinine, bromo-acetylcholine, or zymosan) is injected in mice intraperitoneally, causing a contraction of the abdominal musculature, which is characterized by an elongation of the body extending through to the hind limbs. The number of such responses is quantitated and is reduced by pre-treatment with analgesic agents, thus forming the basis for a screening test (COLLIER, H. O., et al. "The Abdominal Constriction Response and Its Suppression By Analgesic Drugs in the Mouse", *Br J Pharmacol Chemother,* 1968, pp 295-310, Vol 32(2)). This type of abdominal irritant test has been used to predict the analgesic effect of numerous clinically effective agents, the potency of which in the abdominal irritant test parallels the magnitude of the dose needed in the relief of clinical pain. Such agents include acetaminophen, NSAIDS such as aspirin and ibuprofen, opioids, such as morphine and codeine, and other centrally acting analgesics, such as tramadol.

One modification of the chemically-induced abdominal irritant model of visceral pain is to pre-treat animals with agents known to induce inflammatory responses following intraperitoneal injection (such as LPS, zymosan, or thioglycolate). A small intraperitoneal dose of such an inflammogen, administered hours or days before the acute chemical irritant challenge, has been shown to increase the number of abdominal contractions observed (RIBEIRO R. A., et al., "Involvement of resident macrophages and mast cells in the writhing nociceptive response induced by zymosan and acetic acid in mice", *Eur J Pharmacol,* 2000, pp 111-118, Vol 387(1)). While some analgesic agents are effective at mitigating acute viscerochemical nociception, others, particularly those dependent upon receptor induction are more effective at preventing or reversing the enhancement of behavioral responses caused by a preconditioning inflammatory stimulus. Because of the up-regulation of the TRPM8 receptor in inflammation, TRPM8 antagonists that are effective at reducing the mean number of contractions are predicted to provide analgesic action in human clinical use.

The ability of a test compound to mitigate chemical irritant-induced abdominal contractions following a pre-conditioning inflammatory stimulus is studied as follows. Thioglycolate (3%, w/v, 2-3 mL i.p.) is injected into male CD1 mice (20-40 g, Charles River Labs), at a maximum dosage volume of 80 mL/kg, to induce peritoneal inflammation. Following a twenty-four hour pre-inflammation period these mice are dosed orally with test compound (30 mg/kg; n=10) or vehicle (HPMC with 2% Tween80; n=9) and then one hour later subjected to an abdominal irritant challenge of acetic acid (1%, 10 mL/kg, i.p.). Immediately following injection of acetic acid, the mice are placed individually in glass bell jars (approximately 15 cm in diameter) for counting of abdominal contractions over the next 15 minutes. The total number of abdominal contractions is summed for each treatment group and employed in the following formula to calculate Percent Inhibition (% I) as % Inhibition=[1−(test compound contractions/vehicle contractions)]×100.

Example 18

In Vivo Models of Neuropathic Pain

The sciatic nerve is the major sensorimotor innervation of the (hind) leg and foot. Injury to the sciatic nerve or its constituent spinal nerves often results in pain-related behaviors. In rats and mice, tight ligation of the L5 spinal nerve with silk suture, partial tight ligation of the sciatic nerve with silk suture or loose ligation of the sciatic nerve with chromic gut suture each result in behaviors reminiscent of neuropathic pain in humans. These lesions (one per animal) are performed surgically in anesthetized rodents. Both the spinal nerve and sciatic nerve lesions result in allodynia, a painful response to normally innocuous stimuli, and hyperalgesia, an exaggerated response to normally noxious stimuli. It is important to note that both of these pain-related behaviors are evoked by the testing procedures and that normal use of the paw (e.g., walking) is relatively uncompromised, apart from occasional "guarding" of the paw. Subsequent to the surgery, the subjects' behaviors, such as grooming, feeding, and weight gain, are normal, except for hypersensitivity (as defined above) of the affected paw.

In addition to induction by nerve damage resulting from accidental trauma or surgical procedures, neuropathic pain can also be induced by diabetes (FOX, A., et al., "Critical evaluation of the streptozotocin model of painful diabetic neuropathy in the rat", Pain, 1999, pp 307-316, Vol 81) or by treatment with chemotherapeutic agents, such as paclitaxel or vincristine (YAKSH, T. L., et al., "Vincristine-induced allodynia in the rat", Pain, 2001, pp 69-76, Vol 93).

Agents that attenuate neuropathic pain in the clinic also are effective in rodent neuropathic pain models. These agents include the recently approved Cymbalta (Duloxetine) (IYENGAR, S., et al., "Efficacy of Duloxetine, a Potent and Balanced Serotonin-Norepinephrine Reuptake Inhibitor in Persistent Pain Models in Rats", JPET, 2004, pp 576-584, Vol 311), morphine (SUZUKI, R., et al., "The effectiveness of spinal and systemic morphine on rat dorsal horn neuronal responses in the spinal nerve ligation model of neuropathic pain", Pain, 1999, pp 215-228, Vol 80) and gabapentin (HUNTER, J. C., et al., "The effect of novel anti-epileptic drugs in rat experimental models of acute and chronic pain" Eur J Pharmacol 1997, pp 153-160, Vol 324). The dual TRPV1/TRPM8 receptor antagonist BCTC reduced mechanical hyperalgesia and tactile allodynia in the chronic constriction injury rodent neuropathic pain model (POMONIS, J. D., et al., "N-(4-Tertiarybutylphenyl)-4-(3-cholorphyridin-2-yl)tetrahydropyrazine-1(2H)-carbox-amide (BCTC), a Novel, Orally Effective Vanilloid Receptor 1 Antagonist with Analgesic Properties: II. In Vivo Characterization in Rat Models of Inflammatory and Neuropathic Pain", JPET, 2003, pp 387-393, Vol 306). Cold allodynia is a particularly debilitating symptom of neuropathic pain conditions (JORUM, E., et al., "Cold allodynia and hyperalgesia in neuropathic pain: the effect of N-methyl-D-aspartate (NMDA) receptor antagonist etamine—a double-blind, cross-over comparison with alfentanil and placebo", Pain, 2003, pp 229-235, Vol 101). The antiallodynic effect of test compounds in this rodent model is predictive of clinical effect for these novel agents.

Example 18a

Chronic Constriction Injury (CCI)-Induced Model of Neuropathic Pain—Acetone-Induced Hypersensitivity Male Sprague Dawley rats (225-450 g; n=5-8/treatment) were used to evaluate the ability of test compounds to reverse CCI-induced cold hypersensitivity. Four loose ligatures of 4-0 chromic gut were surgically placed around the left sciatic nerve under inhalation anesthesia as described by Bennett et al (BENNETT G. J. et al., "A Peripheral Mononeuropathy in Rat that Produces Disorders of Pain Sensation Like Those Seen in Man", Pain, 1988, pp. 87-107, Vol 33(1)). Fourteen to 35 days following CCI surgery, subjects were placed in elevated observation chambers containing wire mesh floors and five applications of acetone (0.05 mL/application separated by approximately 5 minutes) were spritzed onto the plantar surface of the paw using a multidose syringe. An abrupt withdrawal or lifting of the paw was considered a positive response. The number of positive responses was recorded for each rat over the five trials. Following baseline withdrawal determinations, test compounds were administered in 10% hydroxypropyl-β-cyclodextrin (HP β CD), p.o. The number of withdrawals was re-determined at 2, 3 and 4 hours after compound administration. Compound #71 was tested according to the above described procedure, administering at 10 mg/kg in 10% HP β CD, with results as listed in Table 6, below, presented as a percent inhibition of shakes, which was calculated for each subject as % Inhibition=[1−(test compound withdrawals/pre-test withdrawals)]×100 and then averaged by treatment.

TABLE 6

| Compound #71 | | |
|---|---|---|
| Dose (mg/kg) | Time | % Inhibition |
| 10 | 2 h | 91 |
| 10 | 3 h | 91 |
| 10 | 4 h | 77 |

Example 18b—Prophetic Example

Chronic Constriction Injury (CCI)-Induced Model of Neuropathic Pain—Cold Plate-Induced Hypersensitivity In male SD rats (175-325 g), four loose ligatures of 4-0 chromic gut are surgically placed around the left sciatic nerve under inhalation anesthesia as described by Bennet et al (BENNETT G. J. et al., "A Peripheral Mononeuropathy in Rat that Produces Disorders of Pain Sensation Like Those Seen in Man", *Pain,* 1988, pp. 87-107, Vol 33(1)). Seven to 21 days following sciatic chronic constriction injury (CCI) surgery, the subjects are placed onto a commercial cold plate device cooled by Peltier elements such that the surface temperature is held at 1° C. Each subject undergoes a 6 minute conditioning period followed by a 3 minute assessment period during which the total duration of hind paw lifting is recorded. This procedure is repeated at several intervals prior to and following drug administration. Test compounds are assessed for their ability to return duration of paw lifting back to pre-lesion levels. The duration of paw lifting during the 3 minute test period following administration of test compound is taken as a percentage of the duration of paw lifting during the 3 minute test period prior to test compound treatment.

Example 19—Prophetic Example

Inflammatory Agent-Induced Models of Pyresis/Antipyresis

Test compounds are tested in animal models of pyresis, according to previously documented and validated methods, such as those described by Kozak et al (KOZAK W. et al., "Non-Prostaglandin Eicosanoids in Fever and Anapyrexia", *Front Biosci,* 2004, pp. 3339-3355, Vol 9). Fever is a frequent accompaniment of inflammatory disease. Animal models make use of the pyretic properties of yeast and other inflammatory agents, injecting a yeast suspension or other agent subcutaneously (TOMAZETTI J. et al., "Baker yeast-induced fever in young rats: Characterization and validation of an animal model for antipyretics screening", *J Neurosci Methods,* 2005, pp. 29-35, Vol 147(1); VAN MIERT A. S, et al., "The Antipyretic Effect of Flurbiprofen", *Eur J Pharmacol,* 1977, pp. 197-204, Vol 44(3)). For example, Male Wistar rats (75-100 g) are housed in groups of four to a cage at controlled temperature (23±1° C.) with a 12 h light:12 h dark cycle (lights on at 07:00 h) and with standard lab chow and tap water ad libitum. All measured temperatures are taken between 08:00 and 19:00 h. Each animal is used in only one study. Rectal temperature (TR) are measured by inserting a lubricated thermistor probe (external diameter: 3 mm) 2.8 cm into the rectum of the animal. The probe is linked to a digital device, which displayed the temperature at the tip of the probe with a 0.1° C. precision and logs the values over time. Immediately after measuring the initial basal rectal temperature, the animals are injected with commercially available dried baker yeast (*Saccharomyces cerevisiae*) suspended in pyrogen-free 0.9% NaCl (0.05-0.25 g/kg, i.p.) or 0.9% NaCl (10 ml/kg). TR changes are recorded every hour up to 12 h, and expressed as the difference from the basal value. Since it has been previously been reported that handling and temperature measuring-related stress alter rectal temperature, these animals are habituated to the injection and measuring procedure for 2 days before experiments are carried out. In these sessions, the animals are subjected to the same temperature measuring procedure described above, and are injected intraperitoneally (i.p.) with 0.9% NaCl (10 ml/kg).

To assess the effect of potential antipyretic compounds on basal rectal temperature study animals have their TR measured for 4 h, and after the fourth TR measurement they are subcutaneously (s.c.) injected with vehicle (such as 10% Solutol in sterile water 5 ml/kg) or test compound prepared in vehicle. TR is then recorded every hour up to 8 h after the compound injections. To assess the effect of a test compound on baker yeast-induced hyperthermia, study animals have their basal TR measured and are then injected with a pyrogenic dose of baker yeast (for example, 0.135 g/kg). TR changes are recorded every hour up to 4 h, when potential antipyretics agents or test compounds are administered. Rectal temperature is monitored over the following 8 h. Basal rectal temperature and changes in rectal temperature are expressed as means±S.E.M. of the differences from TR at 07:00 h. Data is analyzed by two-way analysis of variance (ANOVA), with time of measures treated as within subject factor, depending on the experimental design. Post hoc analysis is carried out by the F-test for simple effect and the Student-Newman-Keuls test, when appropriate. A value of $P<0.05$ is considered statistically significant.

The modification of the subsequent pyretic response by therapeutic agents is monitored by rectal telemetry or other measurements of body temperature. Several clinically relevant agents such as acetaminophen, aspirin and ibuprofen, reduce fever in these models. The antipyretic effect of TRPM8 antagonists in these tests would also be predictive of their clinical effect.

Example 20—Prophetic Example

CFA-Induced Model of Rheumatoid Arthritis

Compounds of the formula (I) are tested in animal models of rheumatoid arthritis, according to previously documented and validated methods, such as those described by Nagakura et al (NAGAKURA, Y., "Allodynia and Hyperalgesia in Adjuvant-Induced Arthritic Rats: Time Course of Progression and Efficacy of Analgesics", *J Pharmacol Exp Ther,* 2003, pp 490-497, Vol 306(2)). For example, arthritis is induced by the CFA inoculation in the rats (Male Lewis rats 150-225 g; Charles River). Briefly, 100 mg of *Mycobacterium butyricum* (Difco, Detroit, Mich.) are thoroughly mixed with 20 mL of paraffin oil. Then the mixture is autoclaved for 20 min at 120° C. Each rat is injected in the right footpad (hind paw) with the mixture in a 0.1-mL volume under inhalation anesthesia. The rats serving as controls are injected with 0.1 mL of saline. Pain and other disease development parameters are measured in the CFA- or saline-treated rats just before inoculation and up to 28 days post-inoculation. The measurement for pain parameters are conducted for both mechanical and thermal (hot or cold) endpoints. The measurement of mechanical allodynia are performed using the von Frey hairs (Semmes-Weinstein Monofilaments, Stoelting Co., IL) wherein the rats are habituated to wire mesh bottom cages before the start of the experiment. Static allodynia is tested in the unrestrained rats by touching the plantar surface of the hind paw with von Frey hairs in ascending order of force (1.2, 1.5, 2.0, 3.6, 5.5, 8.5, 12, 15, 29, and 76 g) for up to 6 s or until a paw withdrawal response is elicited. The lowest amount of force required to elicit a response is recorded as the withdrawal threshold in log g. Thermal hyperalgesia is assessed using the radiant heat test wherein a mobile radiant heat source is located under a glass surface upon which the rat is placed. The beam of light is focused on the hind paw, and the paw withdrawal latencies are defined as the time taken by the rat to remove its hind paw from the heat source. The measurement of joint hyperalgesia is performed by a modification of the previously reported method (RUPNIAK, N. M. J., et al., "Effects of the bradykinin $B_1$ receptor des-$Arg^9$[$Leu^8$]bradykinin and genetic disruption of the $B_2$ receptor on nociception in rats and mice", *Pain* 1997, pp 89-97, Vol 71). The torso of each rat is held from the back with the left palm, and the bending and extension (one after the other and five times in each direction) of the ankle within its limits of range of motion are performed with the right fingers. The total number of vocalizations emitted after the manipulation (the bending and extension, five times in each direction) are recorded for each paw (the maximum score is 10 for each paw).

The scoring of mobility is performed by modifying the evaluation scale reported by Butler, et al. (BUTLER S. H., et al, "A limited arthritic model for chronic pain studies in the rat", *Pain* 1992, pp 73-81, Vol 48): score 6, walks normally; score 5, walks being protective toward the ipsilateral hind paw (touches the ipsilateral hind paw fully on the floor); score 4, walks being protective toward the ipsilateral hind paw (touches only the toe of the ipsilateral hind paw on the floor); score 3, walks being protective toward both hind paws (touches the contralateral hind paw fully on the floor); score 2, walks being protective toward both hind paws (touches only the toe of the contralateral hind paw on the floor); score 1, crawls only using the fore paws; and score 0, does not move. Paw volumes are measured by volume displacement of electrolyte solution in a commercially available plethysmometer device. The hind paw is immersed to the junction of the hairy skin, and the volumes are read on a digital display. The scoring of joint stiffness is performed as follows: the body of rats are held from the back with the left palm, and the bending and extension (once in each direction) of the ankle within its limits of range of motion are performed with the right fingers. It is confirmed beforehand that there is no restriction of ankle joint movement in the bending and extension manipulations in naive rats, and the scoring is performed according to the evaluation scale: score 2, there are restrictions of full range of movement of the ankle in both bending and extension; score 1, there is a restriction of full range of movement of the ankle in bending or extension; and score 0, no restriction. The measurements for paw volume and joint stiffness are conducted for both hind paws.

Test compounds are assessed for antihyperalgesic efficacy as follows: thirty-two rats (eight rats per dose and four doses per compound) to be treated with the CFA and another eight rats as naive controls are used for each drug evaluation. The analgesic effects is evaluated on post-inoculation day 9, when mechanical allodynia, thermal hyperalgesia, joint hyperalgesia, and joint stiffness in the ipsilateral paw reached almost the maximum, although those parameters in the contralateral paw changed only slightly and the systemic disturbance shown by the change of mobility score is small. On the day before evaluation, body weight, mechanical allodynia, thermal hyperalgesia, and joint hyperalgesia are measured for the 32 rats that are used for compound evaluation. The rats are allocated to four groups (eight rats per group) such that the differences in the averages of those parameters among the groups became small. All the analgesic effect evaluations and behavioral observations are carried out by the observer who is blind to the drug treatment.

Data is expressed as the mean+/−S.E.M. The time-course curves for mechanical allodynia, thermal hyperalgesia, joint hyperalgesia, body weight, and paw volume is subjected to two-way repeated measures analysis of variance with post hoc t test. In experiments for evaluation of test compound, the difference in scores between the vehicle-treated and naive control groups is analyzed by Student's t test to confirm significant changes in the pain parameters in the ipsilateral paw. The analgesic effects is analyzed by Dunnett's t test, and in each case the drug-treated groups is compared with the vehicle-treated group. In each statistical analysis, the comparison is conducted for paws on the corresponding side. $P<0.05$ is considered statistically significant. In this model, the centrally acting analgesics morphine and tramadol fully relieved pain, whereas the NSAIDs, indomethacin and diclofenac are partially effective, evidencing the model's clinical predictability. The analgesic effect of test compounds in this test would be predictive of their clinical usefulness in treating arthritis.

Example 21—Prophetic Example

Test compounds are tested in animal models of osteoarthritis, according to previously documented and validated methods, such as those described by Sluka et al (SLUKA K. A., et al., "Behavioral and immunohistochemical changes in an experimental arthritis model in rats", *Pain*, 1993, pp. 367-377, Vol 55(3)). For example, male Sprague-Dawley rats (Harlan, Indianapolis, Ind.) weighing 225 to 350 g are briefly anesthetized with vaporized halothane and then injected with a mixture of 3% carrageenan and 3% kaolin (100 μL in 0.9% sterile saline) into the joint cavity of one knee. After the injection, the animals are returned to their cages until the time of testing. For behavioral testing animals are placed in individual clear plastic cages on top of an elevated wire mesh surface that restricted movement. The animals are allowed to acclimate for approximately 1 hour before testing. Von Frey filaments, as described above, are used to test for enhanced responses to mechanical stimuli. The filaments are successively applied through the wire mesh perpendicularly to the plantar surface in between the pads of the third and fourth phalanges. The response threshold to mechanical stimuli are determined before inflammation of the knee joint; 4 hours after inflammation to confirm the development of hyperalgesia; immediately after the administration of test compound such as those of Formula (I) i.e. 5 hours after inflammation; and at 8, 12, and 24 hours after inflammation.

The Kruskal-Wallis test, a nonparametric test, is used to analyze the effects for frequency, intensity, and group for response to mechanical stimuli at baseline, 4 hours after inflammation, and after compound treatment (5 hours, 8 hours, 12 hours, and 24 hours after inflammation). Further post hoc testing between groups is executed by using the Mann-Whitney signed rank test. The data are presented as median with 25th and 75th percentiles. Significance is $P \leq 0.05$.

Additionally, the gait of the animal or other pain-related behavior are scored as the dependent measure of the painful effect of the arthritis on the animal's activity (HALLAS, B. et al., "Establishment of behavioral parameters for the evaluation of osteopathic treatment principles in a rat model of arthritis", *J Am Osteopath Assoc,* 1997, pp 207-214, Vol 97(4)). The effect of test drug on the animal's normal behavior is quantified from zero, meaning no response, to three for incapacitating impairment. Effective analgesic treatment includes the clinically used indomethacin (MOTTA, A. F., et al., "The antinociceptive effect of iontophoretic direct application of diclofenac to arthritic knee-joints of rats", *Life Sci,* 2003, pp 1995-2004, Vol 73(15)). Thus the benefit of test compounds in this model would predict their clinical relevance.

Example 22—Prophetic Example

Sarcoma Cell-Induced Models of Bone Cancer Pain

Test compounds are tested in animal models of bone cancer pain, according to previously documented and validated methods, such as those described in the scientific literature (EL MOUEDDEN, M. et al., "Evaluation of pain-related behavior, bone destruction and effectiveness of fentanyl, sufentanil, and morphine in a murine model of cancer pain", *Pharmacol Biochem Behav,* 2005, pp 109-119, Vol 82(1); GHILARDI, J. R., et al., "Selective Blockade of the Capsaicin Receptor TRPV1 Attenuates Bone Cancer Pain" *J Neurosci,* 2005, pp 3126-3131, Vol 25(12)). In preparation for cell inoculation and tumor induction, osteolytic murine sarcoma cells (NCTC 2472, American Type Culture Collection (ATCC), Rockville, Md., USA) are cultured in NCTC 135 medium (Invitrogen) containing 10% horse serum (Gibco) and passaged 2 times weekly according to ATCC guidelines. For their administration, cells are detached by scraping and then centrifuged at 1000×g. The pellet are suspended in fresh NCTC 135 medium ($2.5 \times 10^6$ cells/20 μL) and then used for intramedullary femur inoculation. Male $C_3H$/HeNCrI mice (25-30 g, Charles River Labs) are used in such experiments. After induction of general anesthesia with xylazine (10 mg/kg i.p.) and ketamine (100 mg/kg i.p.) the left hind paw is shaved and disinfected with povidone-iodine followed by 70% ethanol. A superficial incision of 1 cm is made over the knee overlaying the patella. The patellar ligament is then cut, exposing the condyles of the distal femur. A 23-gauge needle is inserted at the level of the intercondylar notch and the intramedullary canal of the femur to create a cavity for injection of the cells. Twenty microliters of media (sham animals) or media containing tumor cells (approximately $2.5 \times 10^6$ cells) are then injected into the bone cavity using a syringe. To prevent leakage of cells outside the bone, the injection site is sealed with dental acrylic and the wound closed with skin stitches.

Pain behaviors are evaluated in separate groups (n=6) of sham and bone tumor mice with confirmed hyperalgesia as assessed by spontaneous lifting behavior. Animals are behaviorally tested during a 3-week period prior to and after tumor inoculation. Body weight of the mice are recorded throughout the experimental period to help monitor general health status. To measure the spontaneous lifting, the animals are habituated in a transparent acrylic cylinder of 20 cm diameter put on an horizontal surface and thereafter observed during 4 min for spontaneous lifting behavior of the left hind paw. After spontaneous lifting behavior assessment, animals are immediately placed on a mouse rotarod (e.g. ENV-575M\, MedAssociates Inc., GA, USA) at a speed of 16 rpm for 2 min wherein limb-use during forced ambulation is scored: 4=normal; 3=limping; 2=partial non-use of left hind paw; 1=substantial non-use of left hind paw; 0=non-use of left hind paw. Assessment of cold allodynia are made by exposing the ipsilateral hind paw of the mouse to 5 repeated applications of acetone (20 μL) and quantifying the lift/licking frequency and/or duration. Post-mortem evaluation of bone destruction are assessed by ACT processing followed by scanning using a system such as the Skyscan 1076 microtomograph system for small animal imaging (Skyscan 1076\, Skyscan, Aartselaar, Belgium). Measured histomorphometry parameters of bone destruction are subsequently correlated with behavioral endpoints.

The antihyperalgesic, antiallodynic and disease modifying effects of test compounds are tested in this murine model of bone cancer pain in separate groups (n=6 per dose group). Animals with confirmed hyperalgesia, as assessed by spontaneous or acetone-evoked lifting, are behaviorally tested, for example, on days 15 and 22 after distal femur tumor inoculation before and 1 h after systemic administration of vehicle (e.g. 10% Solutol in sterile water) or test compound. The statistical analysis is performed by one-way ANOVA to compare behavioral measurements and bone parameters among the experimental groups. To compare behavioral measurements and bone parameters between sham and tumor-bearing animals, a Mann-Whitney U test is used. Results are considered statistically significant at $P<0.05$ (two-tailed). Data are expressed as mean+/−S.E.M.

Bone cancer causes intense pain in humans, mimicked in animal models of bone cancer pain in rodents such as that described above. Analgesic treatments that are effective in this model include COX-2 inhibitors (SABINO M. A., et al., "Simultaneous Reduction in Cancer Pain, Bone Destruction, and Tumor Growth by Selective Inhibition of Cyclooxygenase-2", *Cancer Res,* 2002, pp 7343734-9, Vol 62(24)) and high doses of morphine (LUGER, N. M., et al., "Efficacy of systemic morphine suggest a fundamental difference in the mechanisms that generate bone cancers vs. inflammatory pain", *Pain,* 2002, pp 397-406, Vol 99(3)), agents used clinically for pain relief in patients experiencing bone cancer pain. Because this model so closely mimics the human disease state, the finding that cold allodynia is a prominent symptom (LEE, S., et al. "Behavioral Characteristics of a mouse model of cancer pain", *Yonsei Med J,* 2005, pp. 252-259, Vol 46(2)) strongly supports the concept that TRPM8 antagonists will provide relief of pain associated with human bone cancer.

Example 23—Prophetic Example

Respiratory Irritant-Induced Models of Cough

Test compounds are tested in animal models of antitussive activity, according to previously documented and validated methods, such as those described by: TANAKA, M., et al., "Mechanisms of Capsaicin- and Citric-Acid-Induced Cough Reflexes in Guinea Pigs", *J Pharmacol. Sci,* 2005, pp 77-82, Vol 99(1); TREVISANI, M., et al., "Antitussive activity of iodo-resiniferatoxin in guinea pigs" *Thorax,* 2004, pp. 769-772, Vol 59(9); and HALL, E. et al., "Time-course of infection and responses in a coughing rat model of pertussis", *J Med Microbiol,* 1999, pp 95-98, Vol 48. Testing is conducted in transparent ventilated chambers with a constant airflow of 400 mL/min. The tussive agent (citric acid 0.25 M or capsaicin 30 mM) is nebulized via a miniultrasonic nebulizer with an output of 0.4 mL/min. The appearance of cough is detected by means of a tie clip microphone and confirmed by the characteristic posture of the animal. The cough sounds are recorded and digitally stored. A blinded observer subsequently counts the number of elicited cough efforts. In some cases, animals are sensitized by pre-exposure to certain agents such as ovalbumin. A test compound is administered to at the peak of irritant-induced cough to evaluate the antitussive effects of the compound. In addition, prophylactic or multiple dosing regimes are utilized to evaluate the test compound for modulation of the onset and duration of irritant-induced cough. Variations of these tests predict the antitussive effects of effective clinical agents, including NMDA antagonists such as dextrorphan and dextromethorphan, opioids such as codeine, beta 2 agonists such as salbutamol and antimuscarinics such as ipratropium (BOLSER, D. C. et al., "Pharmacological studies of allergic cough in the guinea pig", *Eur J Pharmacol,* 1995, pp 159-164, Vol 277(2-3); BRAGA, P. C. "Dextrorphan and Dextromethorphan: comparative antitussive effects on guinea pigs", *Drugs Exper Clin Res*, 1994, pp. 199-203, Vol 20). The antitussive action of menthol in both guinea pig and humans (ECCLES, R. "Menthol: Effects on Nasal Sensation of Airflow and the Drive to Breathe", *Curr Allergy Asthma Rep*, 2003, pp. 210-214, Vol 3(3); LAUDE E. A., et al. "The Antitussive Effects of Menthol, Camphor, and Cineole in Conscious Guinea Pigs", *Pulm Pharmacol*, 1994, pp 179-184, Vol 7(3); MORICE A. H., et al. "Effect of inhaled menthol on citric acid induced cough in normal subjects", *Thorax*, 1994, pp. 1024-1026, Vol 49(10)) is predictive of the clinical utility of test compounds as antitussive agents.

Example 24—Prophetic Example

Chemical Irritant-Induced Models of Itch, Contact Dermatitis, Eczema and Other Manifestations of Dermal Allergy, Hypersensitivity and/or Inflammation Test compounds are tested in animal models of contact dermatitis or itch, according to previously documented and validated methods, such as those described in the scientific literature (SAINT-MEZARD, P., et al. "Allergic contact dermatitis" *Eur J Dermatol*, 2004, pp. 284-295, Vol 14(5); THOMSEN, J. S., et al. "The effect of topically applied salicylic compounds on serotonin-induced scratching behavior in hairless rats", *J Exp Dermatol*, 2002, pp 370-375, Vol 11(4); WEISSHAAR, E, et al. "Effect of topical capsaicin on the cutaneous reactions and itching to histamine in atopic eczema compared to healthy skin", *Arch Dermatol Res*, 1998, pp 306-311, Vol 290(6); WILLE, J. J., et al. "cis-Urocanic Acid Induces Mast Cell Degranulation and Release of Preformed TNF-: A Possible Mechanism Linking UVB and cis-Urocanic Acid to Immunosuppression of Contact Hypersensitivity", *Skin Pharmacol Appl Skin Physiol*, 1999, pp 18-27, Vol 12(1-2)). Mice (or species such as guinea pig or rat) are sensitized with 25 mL of 0.5% dinitrofluorobenzene solution (DNFB diluted 4:1 in acetone:olive oil immediately before application or other haptens, such as 12-myristate-13 acetate, picryl chloride, oxazolone, capsaicin, arachidonic acid, lactic acid, trans-retinoic acid or sodium lauryl sulfate) painted to the shaved dorsal skin or untreated (controls). Five days later, 10 mL of 0.2% DNFB (a nonirritant dose) is applied onto both sides of the right ear and the same amount of solvent alone onto the left ear. Ear thickness is monitored daily using a caliper. Test compounds are administered at the peak of inflammation to evaluate the anti-allergy activity of compounds. In addition, prophylactic or multiple dosing regimes are utilized to evaluate the test compound for modulation of the onset and duration of anti-allergy activity. Variations of these tests can predict the anti-allergy and itch activity of effective clinical agents. The ability of these models to predict the therapeutic effect of compounds in human dermal conditions is supported by the cross-species ability of serotonin to induce itch (WEISSHAAR E., et al., "Systemic Drugs with Antipruritic Potency", *Skin Therapy Lett*, 2000, pp 1-25, Vol 5(5)). Additionally, the contact sensitizing property of commercially important drugs and the ability of ion channel modulators to prevent and treat skin sensitization in these models (KYDONIEUS, A., et al., "Elimination of Transdermal Drug-Induced Hypersensitivity by Topical Delivery of Ion Channel Modulating Agents", *Proceedings of the International Symposium on Controlled Release of Bioactive Materials*, 1997, 24th, pp 23-24) demonstrate the therapeutic utility of test compounds in dermal sensitization.

Example 25—Prophetic Example

Chemical Irritant-Induced Models of Rhinitis and Other Manifestations of Nasal Hypersensitivity and/or Inflammation Test compounds are tested in animal models of rhinitis, according to previously documented and validated methods, such as those described in the scientific literature (HIRAYAMA Y., et al., "Effect of FK3657, a non-peptide bradykinin B2 receptor antagonist, on allergic airway disease models", *Eur J Pharmacol*, 2003, pp 197-203, Vol 467(1-3); MAGYAR, T., et al., "Evaluation of vaccines for atrophic rhinitis—a comparison of three challenge models", *Vaccine*, 2002, pp 1797-1802, Vol 20(13-14); TINIAKOV R. L., et al. "Canine model of nasal congestion and allergic rhinitis", *J Appl Physiol*, 2003, pp 1821-1828, Vol 94(5)). Testing is conducted in mouse, guinea pig, dog or human in response to intranasal challenge with one or more irritants such as cold air, capsaicin, bradykinin, histamine, pollens, dextran sulfate, 2,4-tolylene diisocyanate, *Bordetella bronchiseptica*, *Pasteurella multodica* or acetic acid. In some cases, animals are sensitized by pre-exposure to certain agents including, but not limited to, ragweed or ovalbumin. Prior to or following irritant administration, the test subject receives, respectively, the prophylactic or therapeutic administration one or more times of a test compound, or vehicle control, by the enteral or parenteral route. Significant differences indicative of nasal rhinitis or sensitization for the test compound-treated subjects compared with vehicle-treated subjects are taken as evidence of anti-rhinitis activity. Independent variables include dose, frequency and route of administration, time interval between prophylactic or therapeutic test compound administration and irritant challenge as well as sex and non-sex genotype of the test subject. The intimate role of neurogenic inflammation in these hypersensitivity states demonstrates that the test compounds desensitize or block the sensitization underlying these disease states.

Example 26—Prophetic Example

Conflict-Induced Models of Anxiety, Panic Disorder and Other Non-Adaptive Stressful or Phobic Responses Test compounds are tested in animal models of anxiety, panic disorders and other non-adaptive responses, according to previously documented and validated methods, such as those described by Cryan and Holmes (CRYAN, J. F., et al., "Model organisms: The ascent of mouse: advances in modeling human depression and anxiety", *Nat. Rev. Drug Discov.*, 2005, 99 775-790, Vol 4(9)) or Braw et. al. (BRAW, et al. "Anxiety-like behaviors in pre-pubertal rats of the Flinders Sensitive Line (FSL) and Wistar-Kyoto (WKY) animal models of depression", *Behav Brain Res*, 2006, pp 261-269, Vol 167). Specifically, for studies in rats, the following apparatus may be utilized: an open-field arena (62 cm×62 cm) enclosed by opaque walls (30 cm high) and plus-maze consists of two open arms, 50 cm×10 cm, and two enclosed arms, 50 cm×10 cm×40 cm with an open roof, arranged such that the two arms of each type are opposite each other. The maze is elevated to a height of 70 cm. The walls of the enclosed arms are made from black Plexiglas, while the floors from white Plexiglas. Videotape recordings are analyzed using the 'Observer' system (Noldus Information Technology). A subject rat is removed from its home cage, weighed and placed gently in the center of the open-field arena. The rat is allowed to explore the open-field freely while its behavior is videotaped for 5 min. Afterwards, it is transferred to the plus-maze and placed at the center, facing a closed arm. The rat's behavior is videotaped for 5 min, after which it is returned to its home cage. The apparatus is cleaned using a 70% ethanol solution between rats.

Open-field and plus-maze measures are grouped into two behavioral classes, namely 'anxiety-like behaviors' and 'activity'. Open-field behavioral measures may include 1) Anxiety measures: % time in center square, % number of entries to center square (from total squares entered), % time freezing, latency to first freezing (freezing is scored when the subject is in an immobile state for at least 3 seconds; and 2) Activity measures: Total squares entered, number of rearings (standing on two hind legs), latency for first rearing. Plus-maze measures may include 1) Anxiety: % time in open arms, % number of entries to open arms (from total entries), number of unprotected head dips, latency to enter open arm; and 2) Activity: Total entries to all arms. Anxiety-like behaviors and activity are analyzed by one-way ANOVA's on each of the measures, for each the between-subject comparisons. Plus-maze analyses are conducted in a similar fashion.

Testing may also be conducted in mouse or rat in this fashion in order to measure avoidance of other aversive environmental stimuli such as Geller or Vogel anticonflict tests, the light/dark test and the hole-board test (see CRYAN, J. F., et al., "Model organisms: The ascent of mouse: advances in modeling human depression and anxiety", *Nat. Rev. Drug Discov.,* 2005, 99 775-790, Vol 4(9)). Prior to environmental exposure, the test subject receives the prophylactic administration one or more times of test compound, or vehicle control (e.g. 10% Solutol in sterile water), by the enteral or parenteral route. The cumulative time or number of times spent engaged in the aversive behavior is measured. Significant differences in one or more of these measures for the test compound-treated subjects compared with vehicle-treated subjects is taken as evidence of anxiolytic activity. Because these models are pharmacologically validated by the effectiveness of clinically useful anxiolytics (CRYAN, J. F., et al., "Model organisms: The ascent of mouse: advances in modeling human depression and anxiety", *Nat. Rev. Drug Discov.,* 2005, 99 775-790, Vol 4(9)), they are useful for the detection of anxiolytic compounds.

Example 27—Prophetic Example

Bladder Pressure- and Hypertrophy-Induced Models of Urinary Incontinence

Test compounds are tested in animal models of urinary incontinence according to previously documented and validated methods, such as those described by in the scientific literature (KAISER, S. et al., DE Patent 10215321 (EP1 359 158 A2,A3 (Equivalent)); MCMURRAY. G., et al., "Animal models in urological disease and sexual dysfunction", *Br J Pharmacol,* 2006: pp. S62-79, Vol 147, Suppl 2). TRPM8 is expressed in human prostate, testicle, seminiferous tubules, scrotal skin and inflamed bladder (STEIN, R. J., et al., "Cool (TRPM8) and hot (TRPV1) receptors in the bladder and male genital tract", *J Urol,* 2004): pp 1175-1178, Vol 172(3); MUKERJI, G. et al. "Pain during ice water test distinguishes clinical bladder hypersensitivity from overactivity disorders" *BMC Urology,* 2006, pg 6, Vol 6). Excitation of TRPM8 receptors through cooling or application of menthol causes contraction in the bladder and a decrease in micturation threshold volume (TSUKIMI, Y., et al. "Cold response of the bladder in guinea pig: involvement of transient receptor potential channel, TRPM8", *Urology,* 2005, pp 406-410, Vol 65(2)). To assess test compounds for potential urinary incontinence activity, Sprague-Dawley rats are surgically implanted with bladder catheters allowing for the delivery of fluid (typically saline) and the monitoring of pressure (using a pressure transducer). Cystometry recordings are monitored with a polygraph to evaluate voiding interval, threshold pressure, bladder capacity, bladder compliance, and the number of spontaneous bladder contractions. For example, the bladder catheter is connected to a Harvard infusion pump, and bladders perfused overnight with saline at 2 mL/h. The next morning the bladder catheter is attached (using a "T" connector) to a Statham pressure transducer (Model P23 Db) and to a Harvard infusion pump. A plastic beaker attached to a force displacement transducer (Grass FTO3) is placed under the rat's cage to collect and record urine volume. The cystometric evaluation of bladder function is started by infusing saline (20 mL/h) and after the first micturition the infusion is maintained for 20 min. Two hours after the first cystometry period, the rats are dosed orally with compounds of the formula (I) and a second cystometry is performed between 30 min and 4 h after administration of test compound. The appropriate vehicle (e.g. 10% Solutol in sterile water) is similarly administered to groups of rats that served as controls and the cystometry are performed at the same respective time points.

Test compounds are also be evaluated under conditions of bladder hypertrophy and instability. Under anesthesia, a silk ligature is tied around the proximal urethra of rodents producing a partial outlet obstruction and subsequent hypertrophied bladder development within 6-9 weeks (WOODS, M. et al., "Efficacy of the 3-adrenergic receptor agonist CL-316243 on experimental bladder hyperreflexia and detrusor instability in the rat", *J Urology,* 2001, pp 1142-1147, Vol 166). Cystometry recordings are evaluated as described above. Such preclinical procedures are sensitive to compounds having clinical utility for the treatment of urinary incontinence (SOULARD, C., et al., "Pharmacological Evaluation of JO 1870: Relation to the Potential Treatment of Urinary Bladder Incontinence", *J Pharmacol Exp Ther,* 1992, pp 1152-1158, Vol 260(3)), and the activity of test compounds in this model would be predictive of clinical utility.

Example 28—Prophetic Example

In Vivo Model for Cold-Enhanced Central Pain States

Injury to the brain or spinal cord, such as that caused by trauma, interrupted blood flow or neurodegenerative diseases, often precipitates a central pain condition. Examples of such injuries characterized, in part by, a hypersensitivity to cold stimuli include multiple sclerosis (MORIN, C., et al., "Disruption of Thermal Perception in a Multiple Sclerosis Patient With Central Pain", *Clin J Pain,* 2002, pp 191-195, Vol 18(3); SVENDSEN, K. B., et al. "Sensory function and quality of life in patients with multiple sclerosis and pain", *Pain,* 2005, pp 473-481, Vol 114(3)), stroke or cerebral ischemia (GREENSPAN, J. D., et al., "Allodynia in patients with post-stroke central pain (CPSP) studied by statistical quantitative sensory testing within individuals", *Pain,* 2004, pp 357-366, Vol 109(3)) and spinal cord injury (DEFRIN, R., et al., "Characterization of chronic pain and somatosensory function in spinal cord injury subjects", *Pain,* 2001, pp 253-263, Vol 89(2-3); DEFRIN, R., et al. "Sensory Determinants of Thermal Pain", *Brain,* 2002, pp 501-510, Vol 125(Pt 3); FINNERUP, N. B., et al., "Intravenous Lidocaine Relieves Spinal Cord Injury Pain: A Randomized Controlled Trial", *Anesthesiology,* 2005, pp 1023-1030, Vol. 102(5)). Each of these conditions may be readily modeled in animals for assessment of the ability of test compounds to mollify the hypersensitive state. For example, a spinal cord injury (SCI) is performed in adult Sprague-Dawley rats having a body weight of 150-200 g at time of surgery (ERICHSEN, et al., "Comparative actions of the opioid analgesics morphine, methadone and codeine in rat models of peripheral and central neuropathic pain", *Pain,* 2005, pp 347-358, Vol 116). The rats are anaesthetized with chloral hydrate (300 mg/kg, i.p. Sigma, USA) and a catheter is inserted into the jugular vein. A midline skin incision is made along the back to expose the T11-L2 vertebrae. The animals are positioned beneath a tunable argon ion laser (Innova model 70, Coherent Laser Products Division, CA, USA) operating at a wavelength of 514 nm with an average power of 0.17 W. The laser light is focused into a thin beam covering the single T13 vertebra, which is irradiated for 10 min. Immediately before the irradiation, erythrosin B (Aldrich, 32.5 mg/kg dissolved in 0.9% saline) is injected intravenously via the jugular catheter. Due to rapid metabolism of erythrosin B, the injection is repeated after 5 min in order to maintain adequate blood concentrations. During irradiation, the body core temperature is maintained at 37-38° C. by a heating pad. After irradiation the wound are closed in layers and the skin sutured together.

SCI rats are routinely tested for the presence of pain-like behaviors from 3-4 weeks after surgery. The fur of the animals are shaved at least a day prior to examination of the cutaneous pain threshold to avoid sensitization of the skin receptors. During testing, the rats are gently held in a standing position by the experimenter and the flank area and hind limbs are examined for hypersensitivity to sensory stimulation. On the day of drug testing, SCI rats are administered drug according to the experimental schedule and the time course of pain-like behaviors are measured. To test for the presence of cold allodynia, ethyl chloride or acetone are sprayed onto the skin of the animals, often that which has been previously determined to be sensitive to mechanical stimulation by von Fry filament testing. The subsequent response to cold stimulation is observed and classified according to the following scale: 0, no visible response; 1, localized response (skin twitch) without vocalization; 2, transient vocalization; 3, sustained vocalization. Kruskal Wallis ANOVA on ranks is used to analyze the overall effects of non-parametric data obtained in response to cold stimulation following pretreatment with either test compound or vehicle.

Example 29—Prophetic Example

In Vivo Model for Post-Anesthetic Shivering

Spontaneous post-anesthetic tremor that resembles shivering is common during recovery from anesthesia. Risks to postoperative patients include an increase in metabolic rate of up to 400%, hypoxemia, wound dehiscence, dental damage, and disruption of delicate surgical repairs. The etiology of spontaneous post-anesthetic tremor is most commonly attributed to normal thermoregulatory shivering in response to intraoperative hypothermia. In most operating and recovery rooms, shivering is controlled by the use of humidifiers, warming blankets, and inhalation of humidified heated oxygen. However, pharmacological control is an effective alternate treatment modality (BHATNAGAR, S., et al. "Tramadol for Postoperative Shivering: A Double Blind Comparison with Pethidine", *Anaesth Intensive Care,* 2001, pp 149-154, Vol 29(2); TSAI, Y. C., et al., "A Comparison of Tramadol, Amitriptyline, and Meperidine for Postepidural Anesthetic Shivering in Parturients", *Anesth Analg,* 2001, pp 1288-1292, Vol 93(5)). Test compounds may be assessed for their ability to mitigate post-anesthetic induced-shaking by using animal models such as that described by Nikki et al (NIKKI, P., et al., "Halothane-Induced Heat Loss and Shivering in Rats", *Acta Anaesthesiol Scand,* 1968, pp 125-134, Vol 12(3) and Grahn (GRAHN, D. A., et al. "Appropriate thermal manipulations eliminate tremors in rats recovering from halothane anesthesia", *J Applied Physiology,* 1996, pp 2547-2554, Vol 81). For example, Wistar rats (males, weighing 250-450 g;) are surgically implanted with an EEG/EMG recording array to assess post anesthetic tremor activity. The EEG electrodes are located bilaterally 2 mm off midline and adjacent to bregma and lamda. Following a one-week recovery period, frontal-occipital EEG, raw EMG, and integrated EMG activities, as well as three temperatures (skin, rectal, and water blanket temperatures during anesthesia), and ambient temperature post-anesthesia are monitored throughout the experiment using copper-constantin thermocouples. The EEG and EMG signals are recorded on polygraph paper (5 mm/s, Grass model 7E polygraph) and, during recovery from anesthesia, the EEG is computer scored in 10 second epochs as either synchronized: high amplitude (0.100 µV), low frequency (1-4 Hz dominated) activity characteristic of slow-wave sleep (SWS-like) or desynchronized: low amplitude (75 µV), high frequency (5-15 Hz dominated), characteristic of waking and rapid-eye-movement sleep (W-like). The EMG activity is quantified as the averaged summed voltage/time interval by processing the raw EMG signal through an integrator (Grass model 7P3, 0.5 s time constant). On the day of an experiment, the animal is placed in a small acrylic box (15×15×15 cm) and exposed to a halothane vapor-air mixture (4% halothane). Immediately after the induction of anesthesia, the animal is removed from the enclosure and subsequently anesthetized through a nose cone. Following cessation of anesthesia, two stages of recovery are judged: emergence from anesthesia and restoration of behavioral activity (behavioral recovery). Emergence from anesthesia is defined as an increase in tonic EMG activity and a change in the EEG from a SWS-like pattern to a W-like pattern. Behaviorally, recovery occurs when the animal rises from a prone position and initiates coordinated movements. The time intervals from termination of anesthesia to emergence and behavioral recovery are measured in all animals. Time interval data are subjected to a repeated measure analysis of variance, and the Scheffe's method are employed for testing differences between pairs of means.

Example 30—Prophetic Example

TRPM8 Patch Clamp Assays

For patch clamp experiments, HEK293 cells are stably transfected with canine TRPM8 and cultured in DMEM supplemented with 10% fetal bovine serum, 100 units/ml penicillin, 100 µg/ml streptomycin and 1 mg/ml G418. Cells are maintained at 37° C. and in 5% $CO_2$.

The extracellular solution contains (in mM): NaCl, 132; EGTA, 1; KCl, 5.4; $MgCl_2$, 0.8; HEPES, 10; glucose, 10; pH=7.4. Recordings are performed using the conventional whole-cell patch clamp technique, 1-2 days after plating cells onto glass coverslips at densities appropriate for single cell recording. Currents are amplified by a patch clamp amplifier and filtered at 2 kHz (Axopatch 200B, Molecular Devices, Union City, Calif.). Menthol (100 µM) is applied to the cell at 0.5 ml/min via a gravity-fed perfusion system. Recordings involving menthol activation are performed at 22° C.

In experiments where temperatures are varied, temperature ramps are generated by cooling the perfusate in an in-line cooler (Model SC-20, Warner Instruments, Hamden, Conn.) controlled by a temperature controller (Model CL-100, Warner Instruments). The temperature in the vicinity of the recorded cell is measured with a custom-made miniature thermo-microprobe connected to a monitoring thermometer (Model TH-8, Physitemp, Clifton, N.J.), and sampled using Digidata 1322A and pClamp 9.0 (Molecular Devices), as are the currents concurrently measured in the whole-cell patch clamp mode. The current is continuously sampled (at 100 Hz) at a holding potential of −60 mV.

Test compounds are diluted from 10 mM DMSO stocks (stored at −20° C.) into an extracellular solution either containing 100 µM menthol or subjected to cooling. Increasing concentrations of a test compound are applied to a cell in a cumulative manner and concentration-dependent responses are measured after steady-state activation is achieved by either 100 µM menthol or cooling to 10° C. A saturating concentration of a reference antagonist is applied at the end of an experiment (either in the presence of 100 µM menthol or 10° C. temperature) to establish the baseline from which all the other measurements are subtracted.

Percentage inhibition by a compound is calculated as 100× $(1-I_{comp}/I_0)$; where $I_{comp}$ and $I_0$ are steady-state current amplitudes in either the presence or absence of a concentration of compounds of the formula (I). Concentration-response data are fitted to a logistic function as $R=100/(1+c/IC_{50})^p$; where, R is the percentage inhibition, p is the Hill coefficient and c is the concentration of the test compound.

Example 31—Prophetic Example

In Vitro Rat and Human TRPM8 Functional Assay

For functional expression of TRPM8, the full-length cDNAs encoding human and rat TRPM8 are subcloned into pCI-NEO mammalian expression vectors. The expression constructs are transiently transfected into HEK293 cells according to the FuGENE 6 transfection Reagent® (ROCHE) instructions. HEK293 cells are routinely grown as monolayers in Dulbecco's minimum essential medium supplemented with 10% FBS, 1 mM L-glutamine, 100 units/mL penicillin and 100 ug/mL streptomycin. Cells are maintained in 5% $CO_2$ at 37° C. Within twenty-four hours, transiently transfected human and rat TRPM8 are seeded into clear-base poly-D-lysine coated 384-well plates (BD Biosciences, NJ, USA) at a density of 10,000 cells per well in culture medium and grown overnight. The following day, all medium is removed and the cells are incubated with 52 µL of 0.5× calcium 3 dye (Molecular Devices) prepared in complete assay buffer containing 20 mM HEPES, 0.1% BSA, and 2.5 mM probenecid at 37° C. for thirty five minutes. The cells are then incubated for an additional fifteen minutes at room temperature before initiating experiments. Following incubation, plates are inserted into a FDSS instrument, where cells are challenged with compounds of the formula (I) (at varying concentrations) and intracellular $Ca^{2+}$ is measured for 5 min prior to the addition of 100 nM icilin. $IC_{50}$ values for test compounds are determined from eight-point dose-response studies Maximal fluorescence intensity (FI) achieved upon addition of icilin is exported from the FDSS and further analyzed using GraphPad Prism 3.02 (Graph Pad Software Inc., CA, U.S.A.). Basal FI is subtracted prior to normalizing data to percent of maximal response. The dose response curves from the average of quadruplicate wells for each data point are analyzed by using nonlinear regression of either sigmoidal dose response or sigmoidal dose response (variable slope). Finally, the $IC_{50}$ values are calculated with the best-fit dose curve determined by Prism.

Example 32—Prophetic Example

Cold-Evoked Cardiovascular Pressor Responses

Test compounds are tested in animals and humans for their ability to mitigate cardiovascular pressor responses evoked by cold exposure. Seasonal environmental cooling is directly associated with elevated blood pressure and an increased incidence of coronary events in human populations worldwide (BARNETT, A. G., et al. "Cold periods and coronary events: an analysis of populations worldwide", *J Epidemiol Community Heath,* 2005, pp 551-557, Vol 59). The clinical cold pressor test assesses changes in blood pressure (BP) and cold pain perception during a 2-3 minute immersion of one hand into ice water. This test is utilized to characterize analgesic compounds (KOLTZENBERG, M., et al., "Differential sensitivity of three experimental pain models in detecting the analgesic effects of transdermal fentanyl and buprenorphine", *Pain,* 2006, pp 165-174, Vol 126(1-3)) and to assess cold hypersensitivity (DESMEULES, J. A., et al., "Neurophysiologic Evidence for a Central Sensitization in Patients With Fibromyalgia", *Arthritis Rheum,* 2003, pp 1420-1429, Vol 48(5)). Test compounds are studied in an anesthetized rat cold pressor paradigm to determine whether TRPM8 antagonism would interfere with the blood pressure pressor response to cold stimulation of the forepaws. Male Sprague-Dawley rats (300-450 g) are anesthetized with sodium pentobarbital and instrumented with a jugular catheter and an indwelling carotid artery pressure transducer. Vehicle (10% Solutol in water) or test compound is infused (1 mL/kg) over one minute through the intravenous catheter. Ten minutes later both forelimbs are packed in crushed ice for 5 minutes. Percent changes in mean arterial pressure in response to this cold stimulus are calculated for vehicle and test compound pretreatments. Percent inhibition attributed to treatment with test compound is then determined using the following formula: % Inhibition=[1−(cold evoked % change in BP post-test compound/cold evoked % change in BP post-vehicle)]×100.

Example 33—Prophetic Example

As a specific embodiment of an oral composition, 100 mg of the Compound #71, prepared as in Example 13, above is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

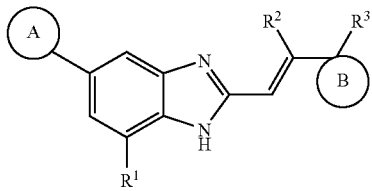

wherein $R^1$ is selected from the group consisting of hydrogen, halogen, lower alkyl and halogenated lower alkyl;

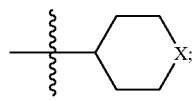

is selected from the group consisting of phenyl, pyridyl and thienyl; wherein the phenyl, pyridyl or thienyl is optionally substituted with one or more substituents independently selected from the group consisting of halogen, hydroxy, lower alkyl, hydroxy substituted lower alkyl, halogenated lower alkyl, lower alkoxy, halogenated lower alkoxy, cyano, —C(O)-(lower alkyl) and 2-(2-methyl-[1,3]dioxolanyl);

$R^2$ is selected from the group consisting of hydrogen and methyl;

$R^3$ is selected from the group consisting of hydrogen and methyl;

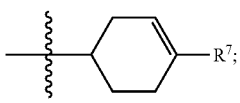

is a ring structure selected from the group consisting of (a)

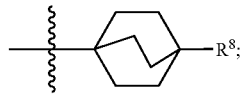

wherein X is selected from the group consisting of $CR^5R^6$, O and S; and wherein $R^5$ and $R^6$ are each independently selected from the group consisting of hydrogen, halogen and lower alkyl;

(b)

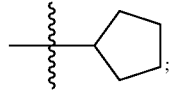

wherein $R^7$ is selected from the group consisting of hydrogen, halogen and lower alkyl;

(c)

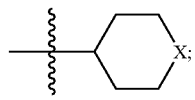

wherein $R^8$ is selected from the group consisting of hydrogen, halogen and lower alkyl; and (d)

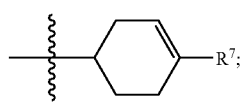

or a tautomer or pharmaceutically acceptable salt thereof.

2. A compound as in claim 1, wherein $R^1$ is selected from the group consisting of hydrogen, lower alkyl and fluorinated lower alkyl;

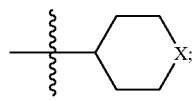

is selected from the group consisting of phenyl, pyridyl and thienyl;

wherein the phenyl, pyridyl or thienyl is optionally substituted with one to two substituents independently selected from the group consisting of halogen, hydroxy, lower alkyl, hydroxy substituted lower alkyl, fluorinated lower alkyl, lower alkoxy, fluorinated lower alkoxy, cyano, —C(O)-(lower alkyl) and 2-(2-methyl-[1,3]dioxolanyl);

$R^2$ is selected from the group consisting of hydrogen and methyl;

$R^3$ is selected from the group consisting of hydrogen and methyl;

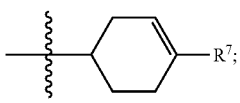

is a ring structure selected from the group consisting of (a)

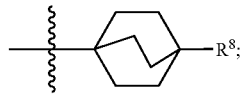

wherein X is selected from the group consisting of $CR^5R^6$, O and S; and wherein $R^5$ and $R^6$ are each independently selected from the group consisting of hydrogen, halogen and lower alkyl;

(b)

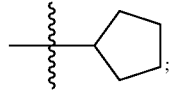

wherein R⁷ is selected from the group consisting of hydrogen and halogen;

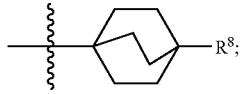
(c)

wherein R⁸ is selected from the group consisting of hydrogen and halogen; and

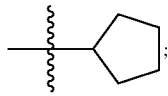
(d)

or a tautomer or pharmaceutically acceptable salt thereof.

3. A compound as in claim 2, wherein

R¹ is selected from the group consisting of hydrogen, C-2alkyl and fluorinated $C_{1-2}$alkyl;

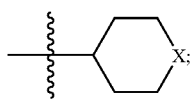

is selected from the group consisting of phenyl, pyridyl and thienyl;
wherein the phenyl, pyridyl or thienyl is optionally substituted with one to two substituents independently selected from the group consisting of halogen, hydroxy, cyano, $C_{1-2}$alkyl, $C_{1-2}$alkoxy, fluorinated $C_{1-2}$alkyl, fluorinated $C_{1-2}$alkoxy, hydroxy substituted $C_{1-2}$alkyl, —C(O)—$C_{1-2}$alkyl and 2-methyl-[1,3]dioxanyl;

R² is selected from the group consisting of hydrogen and methyl;

R³ is selected from the group consisting of hydrogen and methyl;

B is a ring structure selected from the group consisting of

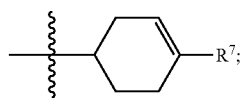
(a)

wherein X is selected from the group consisting of CR⁵R⁶, O and S; and wherein R⁵ and R⁶ are each independently selected from the group consisting of hydrogen, halogen and $C_{1-2}$alkyl;

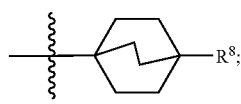
(b)

wherein R⁷ is selected from the group consisting of hydrogen and halogen;

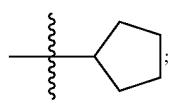
(c)

wherein R⁸ is selected from the group consisting of hydrogen and halogen; and (d)

or a tautomer or pharmaceutically acceptable salt thereof.

4. A compound as in claim 3, wherein

R¹ is selected from the group consisting of hydrogen, methyl and trifluoromethyl;

A is selected from the group consisting of phenyl, 2-fluorophenyl, 2-chlorophenyl, 3-hydroxyphenyl, 2-hydroxymethyl-phenyl, 2-methylphenyl, 2-(2,2,2-trifluoroethoxy)-phenyl, 2-trifluoromethoxyphenyl, 2-trifluoromethylphenyl, 2-cyanophenyl, 2,5-dichlorophenyl, 2,5-difluorophenyl, 2,6-difluorophenyl, 2,6-dimethyphenyl, 2,4-dimethoxyphenyl, 2,6-dimethoxyphenyl, 2-trifluoromethoxy-5-fluoro-phenyl, 2-trifluoromethoxy-6-fluoro-phenyl, 2-methoxy-4-fluoro-phenyl, 2-chloro-5-fluoro-phenyl, 2-chloro-6-fluoro-phenyl, 2-chloro-5-methoxy-phenyl, 3-chloro-6-methoxy-phenyl, 3-fluoro-6-methoxy-phenyl, 2-fluoro-6-methoxy-phenyl, 2-fluoro-6-trifluoromethyl-phenyl, 2-fluoro-6-trifluoromethoxy-phenyl, 2,6-di(trifluoromethyl)phenyl, 2-methylcarbonyl-phenyl, 2-(2-methyl-[1,3]dioxanyl)-phenyl, 2-(3-methyl-thienyl), 4-(3-trifluoromethyl-pyridyl), 3-(2-trifluoromethyl-pyridyl), 2-(3-trifluoromethyl-pyridyl) and 2-(6-trifluoromethyl-pyridyl);

R² is selected from the group consisting of hydrogen and methyl;

R³ is selected from the group consisting of hydrogen and methyl;

B is a selected from the group consisting of cyclopentyl, cyclohexyl, 1-(4,4-difluoro-cyclohexyl), 1-(4,4-dimethyl-cyclohexyl), 4-(1-fluoro-cyclohexenyl), 4-tetrahydropyranyl, 4-tetrahydrothiopyranyl and 4-(1-bromo-bicyclo[2,2]octanyl);

or a tautomer or pharmaceutically acceptable salt thereof.

5. A compound as in claim 4 selected from the group consisting of 2-(2-Cyclohexyl-vinyl)-5-(2-trifluoromethoxy-phenyl)-1H-benzimidazole;
2-(2-Cyclohexyl-vinyl)-5-phenyl-1H-benzimidazole;
2-(2-Cyclohexyl-vinyl)-5-o-tolyl-1H-benzimidazole;
2-(2-Cyclohexyl-vinyl)-5-[2-(2,2,2-trifluoro-ethoxy)-phenyl]-1H-benzimidazole;
3-[2-(2-Cyclohexyl-vinyl)-1H-benzimidazol-5-yl]-phenol;
2-[2-(2-Cyclohexyl-vinyl)-1H-benzimidazol-5-yl]-phenyl}-methanol;
2-(2-Cyclohexyl-vinyl)-5-[2-(2-methyl-[1,3]dioxolan-2-yl)-phenyl]-1H-benzimidazole;
1-{2-[2-(2-Cyclohexyl-vinyl)-1H-benzimidazol-5-yl]-phenyl}-ethanone;
5-(2-Chloro-5-fluoro-phenyl)-2-(2-cyclohexyl-vinyl)-1H-benzimidazole;
5-(2-Chloro-6-fluoro-phenyl)-2-(2-cyclohexyl-vinyl)-1H-benzimidazole;
2-(2-Cyclohexyl-vinyl)-5-(2-fluoro-6-methoxy-phenyl)-1H-benzimidazole;
2-(2-Cyclohexyl-vinyl)-5-(4-fluoro-2-methoxy-phenyl)-1H-benzimidazole;
2-(2-Cyclohexyl-vinyl)-5-(5-fluoro-2-methoxy-phenyl)-1H-benzimidazole;
2-(2-Cyclohexyl-vinyl)-5-(2,6-dimethoxy-phenyl)-1H-benzimidazole;
2-(2-Cyclohexyl-vinyl)-5-(2,6-difluoro-phenyl)-1H-benzimidazole;
2-(2-Cyclohexyl-vinyl)-5-(2-fluoro-phenyl)-1H-benzimidazole;
2-(2-Cyclohexyl-vinyl)-5-(3-methyl-thiophen-2-yl)-1H-benzimidazole;
5-(2-Chloro-5-methoxy-phenyl)-2-(2-cyclohexyl-vinyl)-1H-benzimidazole;
2-(2-Cyclohexyl-vinyl)-5-(2,5-dichloro-phenyl)-1H-benzimidazole;
5-(5-Chloro-2-methoxy-phenyl)-2-(2-cyclohexyl-vinyl)-1H-benzimidazole;
2-(2-Cyclohexyl-vinyl)-5-(2,5-dimethoxy-phenyl)-1H-benzimidazole;
2-(2-Cyclohexyl-vinyl)-5-(2,5-difluoro-phenyl)-1H-benzimidazole;
2-(2-Cyclopentyl-vinyl)-5-(2-fluoro-phenyl)-1H-benzimidazole;
2-(2-Cyclopentyl-vinyl)-5-(3-methyl-thiophen-2-yl)-1H-benzimidazole;
2-(2-Cyclopentyl-vinyl)-5-(2-trifluoromethoxy-phenyl)-1H-benzimidazole;
2-[2-(2-Cyclopentyl-vinyl)-1H-benzimidazol-5-yl]-benzonitrile;
{2-[2-(2-Cyclopentyl-vinyl)-1H-benzimidazol-5-yl]-phenyl}-methanol;
1-{2-[2-(2-Cyclopentyl-vinyl)-1H-benzimidazol-5-yl]-phenyl}-ethanone;
2-[2-(4,4-Difluoro-cyclohexyl)-vinyl]-5-(2-trifluoromethyl-phenyl)-1H-benzimidazole;
2-[2-(4,4-Difluoro-cyclohexyl)-vinyl]-5-(2-fluoro-6-trifluoromethyl-phenyl)-1H-benzimidazole;
2-[2-(4-Fluoro-cyclohex-3-enyl)-vinyl]-5-(2-trifluoromethyl-phenyl)-1H-benzimidazole;
2-[2-(4-Fluoro-cyclohex-3-enyl)-vinyl]-5-(2-trifluoromethoxy-phenyl)-1H-benzoimidazole;
2-[2-(4-Fluoro-cyclohex-3-enyl)-vinyl]-5-(5-fluoro-2-methoxy-phenyl)-1H-benzoimidazole;
5-(2-Chloro-phenyl)-2-[2-(4-fluoro-cyclohex-3-enyl)-vinyl]-1H-benzoimidazole;
5-(2,6-Dimethyl-phenyl)-2-[2-(4-fluoro-cyclohex-3-enyl)-vinyl]-1H-benzoimidazole;
2-[2-(4-Fluoro-cyclohex-3-enyl)-vinyl]-5-(2-fluoro-phenyl)-1H-benzoimidazole;
2-[2-(4,4-Difluoro-cyclohexyl)-vinyl]-5-(2-trifluoromethoxy-phenyl)-1H-benzoimidazole;
5-(2-Chloro-phenyl)-2-[2-(4,4-difluoro-cyclohexyl)-vinyl]-1H-benzoimidazole;
2-[2-(4,4-Difluoro-cyclohexyl)-vinyl]-5-(2-fluoro-phenyl)-1H-benzoimidazole;
5-(2,6-Dimethoxy-phenyl)-2-[2-(4-fluoro-cyclohex-3-enyl)-vinyl]-1H-benzoimidazole;
2-[2-(4-Fluoro-cyclohex-3-enyl)-vinyl]-5-(2-fluoro-6-methoxy-phenyl)-1H-benzoimidazole;
2-[2-(4,4-Difluoro-cyclohexyl)-vinyl]-5-(2-fluoro-6-trifluoromethyl-phenyl)-1H-benzoimidazole;
2-[2-(4,4-Difluoro-cyclohexyl)-vinyl]-5-(2,6-dimethoxy-phenyl)-1H-benzoimidazole;
2-[2-(4,4-Difluoro-cyclohexyl)-vinyl]-5-(2-fluoro-6-methoxy-phenyl)-1H-benzoimidazole;
2-[2-(4,4-Difluoro-cyclohexyl)-vinyl]-5-(5-fluoro-2-methoxy-phenyl)-1H-benzoimidazole;
2-[2-(4-Fluoro-cyclohex-3-enyl)-vinyl]-7-trifluoromethyl-5-(2-trifluoromethyl-phenyl)-1H-benzoimidazole;
2-[2-(4,4-Difluoro-cyclohexyl)-vinyl]-7-trifluoromethyl-5-(2-trifluoromethyl-phenyl)-1H-benzoimidazole;
2-(2-Cyclohexyl-vinyl)-7-methyl-5-(2-trifluoromethoxy-phenyl)-1H-benzoimidazole;
2-(2-Cyclohexyl-vinyl)-7-methyl-5-(2-trifluoromethyl-phenyl)-1H-benzoimidazole;
(E)-2-[2-(Tetrahydro-pyran-4-yl)-vinyl]-5-(2-trifluoromethyl-phenyl)-1H-benzimidazole;
(E)-2-[2-(Tetrahydro-thiopyran-4-yl)-vinyl]-5-(2-trifluoromethyl-phenyl)-1H-benzimidazole;
(E)-5-(2-Fluoro-phenyl)-2-[2-(tetrahydro-pyran-4-yl)-vinyl]-1H-benzimidazole;
(E)-7-Methyl-2-[2-(tetrahydro-pyran-4-yl)-vinyl]-5-(2-trifluoromethyl-phenyl)-1H-benzimidazole;
(E)-2-[2-(Tetrahydro-pyran-4-yl)-vinyl]-5-(2-trifluoromethyl-pyridin-4-yl)-1H-benzimidazole;
(E)-2-(2-Cyclohexyl-vinyl)-5-(2-trifluoromethyl-pyridin-4-yl)-1H-benzimidazole;
(E)-2-(2-Cyclohexyl-vinyl)-5-(2-trifluoromethyl-pyridin-3-yl)-1H-benzimidazole;
(E)-2-(2-Cyclohexyl-vinyl)-5-(2-fluoro-6-trifluoromethyl-phenyl)-1H-benzimidazole;
(E)-5-(2,6-Bis-trifluoromethyl-phenyl)-2-(2-cyclohexyl-vinyl)-1H-benzimidazole;
(E)-2-(2-Cyclohexyl-vinyl)-5-(2-fluoro-6-trifluoromethoxy-phenyl)-1H-benzimidazole;
(E)-2-(2-Cyclohexyl-vinyl)-5-(3-trifluoromethyl-pyridin-2-yl)-1H-benzimidazole;
(E)-5-(2,6-Difluoro-phenyl)-2-[2-(tetrahydro-pyran-4-yl)-vinyl]-1H-benzimidazole;
(E)-2-[2-(Tetrahydro-pyran-4-yl)-vinyl]-5-(3-trifluoromethyl-pyridin-2-yl)-1H-benzimidazole;
(E)-2-[2-(4,4-Dimethyl-cyclohexyl)-vinyl]-7-methyl-5-(2-trifluoromethyl-phenyl)-1H-benzoimidazole;
(E)-2-[2-(4,4-Dimethyl-cyclohexyl)-vinyl]-5-(2-trifluoromethyl-phenyl)-1H-benzoimidazole;

(E)-5-(2,6-Difluoro-phenyl)-2-[2-(4,4-dimethyl-cyclo-hexyl)-vinyl]-1H-benzoimidazole;
(E)-2-[2-(4-Methyl-tetrahydro-pyran-4-yl)-vinyl]-5-(2-trifluoromethyl-phenyl)-1H-benzimidazole;
(E)-5-(2,6-Bis-trifluoromethyl-phenyl)-2-[2-(4-methyl-tetrahydro-pyran-4-yl)-vinyl]-1H-benzimidazole;
(E)-2-(2-Cyclohexyl-propenyl)-5-(2-trifluoromethyl-phenyl)-1H-benzimidazole;
(E)-2-(2-Cyclohexyl-propenyl)-5-(2-trifluoromethyl-phenyl)-1H-benzimidazole;
(E)-2-[2-(4-Bromo-bicyclo[2.2.2]oct-1-yl)-vinyl]-5-(2-trifluoromethyl-phenyl)-1H-benzimidazole;
2-(2-Cyclohexyl-vinyl)-5-(2-trifluoromethyl-phenyl)-1H-benzoimidazole;
and tautomers and pharmaceutically acceptable salts thereof.

6. A compound as in claim 4, wherein
$R^1$ is selected from the group consisting of hydrogen, methyl and trifluoromethyl;

(A)

is selected from the group consisting of 2-fluorophenyl, 2-chlorophenyl, 2-hydroxymethyl-phenyl, 2-methylphenyl, 2-(2,2,2-trifluoroethoxy)phenyl, 2-trifluoromethoxyphenyl, 2-trifluoromethylphenyl, 2,6-dimethyphenyl, 2,6-dimethoxyphenyl, 2-trifluoromethoxy-5-fluoro-phenyl, 2-chloro-5-fluoro-phenyl, 2-chloro-6-fluoro-phenyl, 3-fluoro-6-methoxy-phenyl, 2-fluoro-6-methoxy-phenyl, 2-fluoro-6-trifluoromethyl-phenyl, 2-fluoro-6-trifluoromethoxy-phenyl, 2,6-di(trifluoromethyl)phenyl, 2-(3-methyl-thienyl), 3-(2-trifluoromethyl-pyridyl) and 2-(3-trifluoromethyl-pyridyl);
$R^2$ is selected from the group consisting of hydrogen and methyl;
$R^3$ is selected from the group consisting of hydrogen and methyl;

(B)

is a selected from the group consisting of cyclopentyl, cyclohexyl, 1-(4,4-difluoro-cyclohexyl), 1-(4,4-dimethyl-cyclohexyl), 4-(1-fluoro-cyclohexenyl), 4-tetrahydropyranyl and 4-(1-bromo-bicyclo[2,2]octanyl);
or a tautomer or pharmaceutically acceptable salt thereof.

7. A compound as in claim 4, wherein
$R^1$ is selected from the group consisting of hydrogen, methyl and trifluoromethyl;

(A)

is selected from the group consisting of 2-fluorophenyl, 2-chlorophenyl, 2-methylphenyl, 2-(2,2,2-trifluoroethoxy)-phenyl, 2-trifluoromethoxyphenyl, 2-trifluoromethylphenyl, 2,6-dimethyphenyl, 2,6-dimethoxyphenyl, 2-trifluoromethoxy-5-fluoro-phenyl, 2-chloro-6-fluoro-phenyl, 3-fluoro-6-methoxy-phenyl, 2-fluoro-6-methoxy-phenyl, 2-fluoro-6-trifluoromethyl-phenyl and 2-fluoro-6-trifluoromethoxy-phenyl;
$R^2$ is hydrogen;
$R^3$ is hydrogen;

(B)

is a selected from the group consisting of cyclohexyl, 1-(4,4-difluoro-cyclohexyl), 4-(1-fluoro-cyclohexenyl) and 4-tetrahydropyranyl;
or a tautomer or pharmaceutically acceptable salt thereof.

8. A compound as in claim 4, wherein
$R^1$ is hydrogen;

(A)

is selected from the group consisting of 2-trifluoromethylphenyl, 2,6-di(trifluoromethyl)-phenyl and 2-fluoro-6-trifluoromethyl-phenyl;
$R^2$ is hydrogen;
$R^3$ is hydrogen;

(B)

is a selected from the group consisting of cyclohexyl, 1-(4,4-difluoro-cyclohexyl) and 4-tetrahydropyranyl;
and tautomers and pharmaceutically acceptable salts thereof.

9. A compound as in claim 4, selected from the group consisting of
2-(2-Cyclohexyl-vinyl)-5-(2-trifluoromethoxy-phenyl)-1H-benzimidazole;
2-[2-(4,4-Difluoro-cyclohexyl)-vinyl]-5-(2-trifluoromethyl-phenyl)-1H-benzimidazole;
(E)-2-[2-(Tetrahydro-pyran-4-yl)-vinyl]-5-(2-trifluoromethyl-phenyl)-1H-benzimidazole;
(E)-5-(2,6-Bis-trifluoromethyl-phenyl)-2-(2-cyclohexyl-vinyl)-1H-benzimidazole;
(E)-2-(2-Cyclohexyl-vinyl)-5-(2-fluoro-6-trifluoromethoxy-phenyl)-1H-benzimidazole;
2-(2-Cyclohexyl-vinyl)-5-(2-trifluoromethyl-phenyl)-1H-benzoimidazole;
and tautomers and pharmaceutically acceptable salts thereof.

10. A pharmaceutical composition comprising a pharmaceutically acceptable carrier and a compound of claim 1.

11. A pharmaceutical composition made by mixing a compound of claim 1 and a pharmaceutically acceptable carrier.

12. A process for making a pharmaceutical composition comprising mixing a compound of claim 1 and a pharmaceutically acceptable carrier.

* * * * *